United States Patent
Rühter et al.

(10) Patent No.: US 9,242,937 B2
(45) Date of Patent: Jan. 26, 2016

(54) PHARMACEUTICALLY ACTIVE DISUBSTITUTED PYRIDINE DERIVATIVES

(75) Inventors: Gerd Rühter, Hamburg (DE); Peter Nussbaumer, Dortmund (DE); Axel Choidas, Herdecke (DE); Carsten Schulz-Fademrecht, Dortmund (DE); Bert Klebl, Dortmund (DE); Jan Eickhoff, Herdecke (DE)

(73) Assignees: Bayer Intellectual Property GmbH, Monheim (DE); LEAD DISCOVERY CENTER GMBH, Dortmund (DE)

(*) Notice: Subject to any disclaimer, the term of this patent is extended or adjusted under 35 U.S.C. 154(b) by 0 days.

(21) Appl. No.: 14/002,731

(22) PCT Filed: Mar. 1, 2012

(86) PCT No.: PCT/EP2012/053517
§ 371 (c)(1),
(2), (4) Date: Feb. 7, 2014

(87) PCT Pub. No.: WO2012/117059
PCT Pub. Date: Sep. 7, 2012

(65) Prior Publication Data
US 2014/0296304 A1 Oct. 2, 2014

(30) Foreign Application Priority Data
Mar. 2, 2011 (EP) .................................. 11075038

(51) Int. Cl.
| | | |
|---|---|---|
| *C07D 211/72* | (2006.01) | |
| *C07D 213/74* | (2006.01) | |
| *A61K 31/4418* | (2006.01) | |
| *A61K 45/06* | (2006.01) | |

(52) U.S. Cl.
CPC .......... *C07D 213/74* (2013.01); *A61K 31/4418* (2013.01); *A61K 45/06* (2013.01)

(58) Field of Classification Search
CPC .................................................... C07D 213/74
USPC ....................................................... 546/312
See application file for complete search history.

(56) References Cited

U.S. PATENT DOCUMENTS

2010/0048597 A1* 2/2010 Beckwith et al. ............. 514/275
2011/0028492 A1 2/2011 Barsanti et al.

FOREIGN PATENT DOCUMENTS

| | | |
|---|---|---|
| JP | 2006512314 A | 4/2006 |
| JP | 2006522143 A | 9/2006 |
| JP | 2008542219 A | 11/2008 |
| JP | 2009530288 A | 8/2009 |
| JP | 2010525025 A | 7/2010 |
| JP | 2010534677 A | 11/2010 |
| JP | 2011502956 A | 1/2011 |
| WO | 01/25220 A1 | 4/2001 |
| WO | 2004/009562 A1 | 1/2004 |
| WO | 2004/072063 A1 | 8/2004 |
| WO | 2008065155 A1 | 6/2008 |
| WO | 2008132138 A1 | 6/2008 |
| WO | 2008/079933 A2 | 7/2008 |
| WO | 2008109943 A1 | 9/2008 |
| WO | 2009/076140 A1 | 6/2009 |
| WO | 2010/009155 A2 | 1/2010 |
| WO | 2010/022055 A2 | 2/2010 |
| WO | 2011103196 A1 | 8/2011 |

OTHER PUBLICATIONS

Venkatesh et al., J. Pharm. Sci. 89, 145-54 (2000).*
West (Solid-State Chemistry and Its Applications, 1984, John Wiley & Sons).*
Wolff, Burger's medicinal Chemistry and Drug Discovery, vol. 1, Principles and Practice, John Wiley & sons, New York, 1997.*
Brasier 2008, Cell Cycle 7:17, 2661-2666.
Hargreaves et al. 2009, Cell 138, 129-145.
Osuga 2000, PNAS 97 (18): 10254-10259.
Wang 2009, Trends in Pharmacological Sciences 29:6, 302-313.
Kohoutek 2009, Cell Division 4:19.
Uehling 2002, J. Med. Chem. 45, 567-583.
Related copending U.S. Appl. No. 14/002,730, filed Feb. 7, 2015, Examiner: McDowell, Brian E.

* cited by examiner

*Primary Examiner* — Nizal Chandrakumar

(57) ABSTRACT

The present invention relates to disubstituted pyridine derivatives and/or pharmaceutically acceptable salts thereof, the use of these derivatives as pharmaceutically active agents, especially for the prophylaxis and/or treatment of infectious diseases, including opportunistic diseases, immunological diseases, autoimmune diseases, cardiovascular diseases, cell proliferative diseases, inflammation, erectile dysfunction and stroke, and pharmaceutical compositions containing at least one of said disubstituted pyridine derivatives and/or pharmaceutically acceptable salts thereof. Furthermore, the present invention relates to the use of said disubstituted pyridine derivatives as inhibitors for a protein kinase.

7 Claims, No Drawings

PHARMACEUTICALLY ACTIVE DISUBSTITUTED PYRIDINE DERIVATIVES

The present invention relates to disubstituted pyridine derivatives and/or pharmaceutically acceptable salts thereof, the use of these derivatives as pharmaceutically active agents, especially for the prophylaxis and/or treatment of cell proliferative diseases, inflammatory and immunological diseases, cardiovascular diseases and infectious diseases. Furthermore, the present invention is directed towards pharmaceutical composition containing at least one of the disubstituted pyridine derivatives and/or pharmaceutically acceptable salts thereof.

Cyclin-dependent kinase (CDK) family members that trigger passage through the cell cycle are being considered as attractive therapeutic targets, especially for cancer. CDK family members that control other processes such as transcription and RNA processing have caught less attention so far, although experimental evidence for their involvement in different pathological processes is emerging. As a general regulator of transcription, CDK9 is a therapeutic target for treatment of diseases like inflammation, virus replication such as HIV, EBV, and HCV, cancer and cardiac hypertrophy.

CDK9 regulates transcription by phosphorylation of RNA polymerase II as well as additional regulatory factors, thereby enabling productive elongation of transcription. Certain subgroups of genes, especially genes encoding RNAs or proteins with fast turnover like immediate early genes of the inflammatory response, NF-kappaB activated genes (Brasier 2008, Cell Cycle 7:17, 2661-2666, Hargreaves et al. (2009) Cell 138, 129-145); and antiapoptotic genes such as MCL-1 and Bcl-2 family members appear to be especially sensitive to CDK9 inhibition.

In addition, it has been reported that hypertrophic growth of cardiomyocytes is related to CDK9 activation. Furthermore, viruses like the human immune deficiency virus recruit CDK9 actively to nascent RNA transcripts, facilitating their replicating. The dependency of the expression of antiapoptotic genes on CDK9 activity makes it an attractive therapeutic target for various forms of leukaemia such as chronic lymphocytic leukaemia (CLL), acute myelogenous leukaemia (AML) and acute lymphoblastic leukaemia, and solid tumours like prostate, lung, colon, breast and pancreas cancer. In addition, CDK9 inhibitors have been active in models of stroke (Osuga 2000, PNAS 97 (18): 10254-10259).

For reviews, see Wang, 2009 (Trends in Pharmacological Sciences 29:6, 302-313), and Kohoutek, 2009 (Cell Division 2009, 4:19).

BACKGROUND OF THE INVENTION

The present literature discloses several attempts to provide compounds for the use of modulating the activity of protein kinases. The invention of US 2011/028492 A1, filed on Jul. 26, 2010, by Barsanti et al., provides bipyridyl compounds and derivatives as such and for use as pharmaceutical compounds in medicine. The disclosed structures comprise pyridyl-, pyrazinyl- and triazinyl-pyridines:

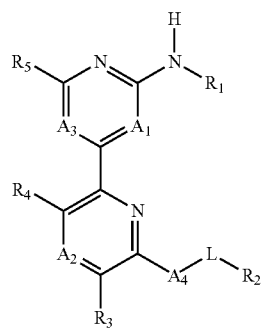

wherein $A_1$-$A_3$ represent independently of each other: N or C—R;

On the other hand the invention of WO 2008/079933 A2, filed on Dec. 20, 2007, by NOVARTIS AG, also provides bipyridyl compounds and derivatives as such and for use as pharmaceutical compounds in medicine. The disclosed structures comprise pyridyl-, pyrazinyl- and triazinyl-pyridines:

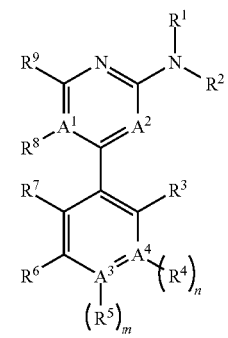

wherein $A^1$-$A^4$ represent independently of each other: N or C—R;

Due to the fact that the focus of US 2011/028492 A1 and WO 2008/079933 A2 is directed to pyridyl-pyridines, pyrazinyl-pyridines and triazinyl-pyridines both state of the art documents relate to structurally different compounds containing nitrogen heterocyclic groups than disclosed in the present invention so that the compounds disclosed in US 2011/028492 A1 and WO 2008/079933 A2 do not challenge novelty or inventiveness of the compounds disclosed herein.

It is object of the present invention to provide compounds and/or pharmaceutically acceptable salts thereof which can be used as pharmaceutically active agents, especially for prophylaxis and/or treatment of cell proliferative diseases, inflammatory diseases, immunological diseases, cardiovascular diseases and infectious diseases, as well as compositions comprising at least one of those compounds and/or pharmaceutically acceptable salts thereof as pharmaceutically active ingredients.

This object is solved by the compounds and/or their pharmaceutically acceptable salts according to independent claim 1, the compounds of the present invention for use as pharmaceutically active agents, the use of the compounds of the present invention for the preparation of a pharmaceutical composition for the prophylaxis and/or treatment of infectious diseases, including opportunistic diseases, immunological diseases, autoimmune diseases, cardiovascular diseases, cell proliferative diseases, inflammation, erectile dysfunction and stroke according to independent claim 6, the use of compounds according to the present invention as inhibitors for the protein kinase CDK9.

Further advantageous features, aspects and details of the invention are evident from the dependent claims, the description, the examples and the drawings.

The novel disubstituted pyridine compounds according to the present invention are defined by the general formula (I)

Formula (I)

wherein
$R^1$ is

L is a bond or —$CR^5R^6$—, —$CR^5R^6$—$CR^7R^8$—, —$CR^5R^6$—$CR^7R^8$—$CR^9R^{10}$—, —$CR^5R^6$—$CR^7R^8$—$CR^9R^{10}$—$CR^{11}R^{12}$;
$R^5$–$R^{12}$ represent independently of each other —H, —$CH_3$, —$C_2H_5$, —$C_3H_7$, —F, —Cl, —Br, —I;
$R^3$ is selected from —H, —$NO_2$, —$NH_2$, —CN, —F, —Cl, —Br, —I, —$CH_3$, —$C_2H_5$, —$C_3H_7$, —$CH(CH_3)_2$, —$C_4H_9$, —$CH_2$—$CH(CH_3)_2$, —$CH(CH_3)$—$C_2H_5$, —$C(CH_3)_3$, —O—$CH_3$, —O—$C_2H_5$, —O—$C_3H_7$, —O—$CH(CH_3)_2$, —O—$C_4H_9$, —O—$CH_2$—$CH(CH_3)_2$, —O—$CH(CH_3)$—$C_2H_5$, —O—$C(CH_3)_3$, —$CR^{13}R^{14}R^{21}$, —$CR^{13}R^{14}$—$CR^{15}R^{16}R^{21}$, —O—$CR^{13}R^{14}R^{21}$, —$CR^{13}R^{14}$—$CR^{15}R^{16}$—$CR^{17}R^{18}R^{21}$, —$CR^{13}R^{14}$—$CR^{15}R^{16}$—$CR^{17}R^{18}$—$CR^{19}R^{20}R^{21}$, —O—$CR^{13}R^{14}$—$CR^{15}R^{16}R^{21}$, —O—$CR^{13}R^{14}$—$CR^{15}R^{16}$—$CR^{17}R^{18}R^{21}$, —$SO_2R^{22}$, —$CONR^{23}R^{24}$, —$NR^{25}COR^{22}$, —O—$CR^{13}R^{14}$—$CR^{15}R^{16}$—$CR^{17}R^{18}$—$CR^{19}R^{20}R^{21}$, —$NR^{25}SO_2NR^{23}R^{24}$, —$NR^{25}SO_2R^{22}$, —$NR^{25}CONR^{23}R^{24}$, —$SO_2NR^{23}R^{24}$, —$SO(NR^{26})R^{22}$, —$NR^{23}R^{24}$;
$R^{13}$–$R^{21}$ and $R^{29}$–$R^{32}$ represent independently of each other —H, —$CH_3$, —$C_2H_5$, —$C_3H_7$, —$C_4H_9$, —F, —Cl, —Br, —I;
$R^{26}$ is —H, —$CH_3$, —$C_2H_5$, —$C_3H_7$, —$CH(CH_3)_2$, —$C_4H_9$, —$CH_2$—$CH(CH_3)_2$, —$CH(CH_3)$—$C_2H_5$, —$C(CH_3)_3$, —$C_5H_{11}$, —$CH(CH_3)$—$C_3H_7$, —$CH_2$—$CH(CH_3)$—$C_2H_5$, —$CH(CH_3)$—$CH(CH_3)_2$, —$C(CH_3)_2$—$C_2H_5$, —$CH_2$—$C(CH_3)_3$, —$CH(C_2H_5)_2$, —$C_2H_4$—$CH(CH_3)_2$, —$C_6H_{13}$, —$C_3H_6$—$CH(CH_3)_2$, —$C_2H_4$—$CH(CH_3)$—$C_2H_5$, —$CH(CH_3)$—$C_4H_9$, —$CH_2$—$CH(CH_3)$—$C_3H_7$, —$CH(CH_3)$—$CH_2$—$CH(CH_3)_2$, —$CH(CH_3)$—$CH(CH_3)$—$C_2H_5$, —$CH_2$—$CH(CH_3)$—$CH(CH_3)_2$, —$CH_2$—$C(CH_3)_2$—$C_2H_5$, —$C(CH_3)_2$—$C_3H_7$, —$C(CH_3)_2$—$CH(CH_3)_2$, —$C_2H_4$—$C(CH_3)_3$, —$CH(CH_3)$—$C(CH_3)_3$, —$CR^{13}R^{14}R^{21}$, —$COR^{28}$, —$CR^{13}R^{14}$—$CR^{15}R^{16}R^{21}$, —$CR^{13}R^{14}$—$CR^{15}R^{16}$—$CR^{17}R^{18}$—$CR^{19}R^{20}R^{21}$, —$CR^{13}R^{14}$—$CR^{15}R^{16}$—$CR^{17}R^{18}R^{21}$, —$CR^{13}R^{14}$—$CR^{15}R^{16}$—$CR^{17}R^{18}$—$CR^{19}R^{20}R^{21}$, —$CR^{13}R^{14}$—$CR^{15}R^{16}$—$CR^{17}R^{18}$—$CR^{19}R^{20}$—$CR^{29}R^{30}$—$CR^{31}R^{32}R^{21}$, —$COOR^{28}$, —$R^{27}$, $R^{22}$, and $R^{28}$ are independently selected from —$R^{27'}$, —$CR^{13}R^{14}R^{21}$, —$CH_3$, —$C_2H_5$, —$C_3H_7$, —$CR^{13}R^{14}$—$CR^{15}R^{16}R^{21}$, —$CR^{13}R^{14}$—$CR^{15}R^{16}$—$CR^{17}R^{18}$—$CR^{19}R^{20}$—$CR^{29}R^{30}R^{21}$, —$CR^{13}R^{14}$—$CR^{15}R^{16}$—$CR^{17}R^{18}R^{21}$, —$CR^{13}R^{14}$—$CR^{15}R^{16}$—$CR^{17}R^{18}$—$CR^{19}R^{20}R^{21}$, —$CR^{13}R^{14}$—$CR^{15}R^{16}$—$CR^{17}R^{18}$—$CR^{19}R^{20}$—$CR^{29}R^{30}$—$CR^{31}R^{32}R^{21}$, —$CH_2Ph$; —$CH_2Ph$ the phenyl group of which may further be substituted by one, two, three, four or five substituents selected from the group consisting of —$CH_3$, —$C_2H_5$, —$C_3H_7$, —F, —Cl, —Br and —I;
$R^{27}$, $R^{27'}$ and $R^{27''}$ are independently selected from these $C_3$-$C_{10}$-cycloalkyl groups may further be substituted by one, two, three, four, five or more substituents selected from the group consisting of —F, —Cl, —Br and —I;
$R^{23}$, $R^{24}$, $R^{77}$ and $R^{78}$ are independently selected from —H, —$CH_3$, —$CR^{13}R^{14}R^{21}$, —$C_2H_5$, —$C_3H_7$, —$CR^{13}R^{14}$—$CR^{15}R^{16}R^{21}$, —$CR^{13}R^{14}$—$CR^{15}R^{16}$—$CR^{17}R^{18}R^{21}$, —$CR^{13}R^{14}$—$CR^{15}R^{16}$—$CR^{17}R^{18}$—$CR^{19}R^{20}$—$CR^{29}R^{30}R^{21}$, —$CR^{13}R^{14}$—$CR^{15}R^{16}$—$CR^{17}R^{18}R^{21}$, —$CR^{13}R^{14}$—$CR^{15}R^{16}$—$CR^{17}R^{18}$—$CR^{19}R^{20}R^{21}$, —$CR^{13}R^{14}$—$CR^{15}R^{16}$—$CR^{17}R^{18}$—$CR^{19}R^{20}$—$CR^{29}R^{30}$—$CR^{31}R^{32}R^{21}$, —$CR^{13}R^{14}$—$CR^{15}R^{16}$—O—$R^{33}$, —$CR^{13}R^{14}$—$CR^{15}R^{16}$—$NR^{33}R^{34}$, —$CR^{13}R^{14}$—$CR^{15}R^{16}$—$CR^{17}R^{18}$—$NR^{33}R^{34}$, —$CR^{13}R^{14}$—$CR^{15}R^{16}$—$CR^{17}R^{18}$—$CR^{19}R^{20}$—$NR^{33}R^{34}$, —$CR^{13}R^{14}$—$CR^{15}R^{16}$—$CR^{17}R^{18}$—O—$R^{33}$, —$CR^{13}R^{14}$—$CR^{15}R^{16}$—$CR^{17}R^{18}$—$CR^{19}R^{20}$—$CR^{29}R^{30}$—$NR^{33}R^{34}$, -Ph, —$CH_2Ph$, phenyl group which may further be substituted by one, two, three, four or five substituents selected from the group consisting of —$CH_3$, —$C_2H_5$, —$C_3H_7$, —F, —Cl, —Br and —I;
—$CH_2Ph$ the phenyl group of which may further be substituted by one, two, three, four or five substituents selected from the group consisting of —$CH_3$, —$C_2H_5$, —$C_3H_7$, —F, —Cl, —Br and —I; or
both residues $R^{23}$ and $R^{24}$ together form with the nitrogen atom to which they are attached a azetidine, pyrrolidine, piperidine, piperazine, azepane, or morpholine ring;
$R^{33}$ and $R^{34}$ represent independently of each other —H, —$CH_3$, —$C_2H_5$, —$C_3H_7$, —$C_4H_9$, —$CH_2Ph$, —$COOC(CH_3)_3$, —$COOCH_3$, —$COOCH_2CH_3$, —$COOCH_2CH_2CH_3$, —$COOCH(CH_3)_2$, —$COOCH_2Ph$, —$COCH_3$;

and $R^{25}$ is selected from —H, —$CH_3$, —$C_2H_5$, —$C_3H_7$, —$CH(CH_3)_2$, —$C_4H_9$, —$CH_2$—$CH(CH_3)_2$, —$CH(CH_3)$—$C_2H_5$ or —$C(CH_3)_3$;

$R^4$ is selected from —H, —$NO_2$, —CN, —F, —Cl, —Br, —I, —$CR^{35}R^{36}R^{37}$, —$CR^{35}R^{36}$—$CR^{38}R^{39}$—$CR^{40}R^{41}$—$CR^{42}R^{43}R^{37}$, —O—$CR^{35}R^{36}$—$CR^{38}R^{39}R^{37}$, —O—$CR^{35}R^{36}$—$CR^{38}R^{39}$—$CR^{40}R^{41}R^{37}$, —$CR^{35}R^{36}$—$CR^{38}R^{39}$—$CR^{40}R^{41}R^{37}$, —O—$CR^{35}R^{36}$—$CR^{38}R^{39}$—$CR^{40}R^{41}$—$CR^{42}R^{43}R^{37}$, —$CR^{35}R^{36}$—$CR^{38}R^{39}R^{37}$, —O—$CR^{35}R^{36}$—$CR^{38}R^{39}$—$CR^{40}R^{41}$—$CR^{42}R^{43}$—$CR^{44}R^{45}R^{37}$, —O—$CR^{35}R^{36}R^{37}$, —O—$CR^{35}R^{36}$—$CR^{38}R^{39}$—$CR^{40}R^{41}$—$CR^{42}R^{43}$—$CR^{44}R^{45}$—$CR^{46}R^{47}R^{37}$, —$CR^{35}R^{36}$—$CR^{38}R^{39}$—$CR^{40}R^{41}$—$CR^{42}R^{43}$—$CR^{44}R^{45}R^{37}$, —$CR^{35}R^{36}$—$CR^{38}R^{39}$—$CR^{40}R^{41}$—$CR^{42}R^{43}$—$CR^{44}R^{45}$—$CR^{46}R^{47}R^{37}$, —$OCH_2Ph$, —$R^{27''}$, —O—$R^{27''}$, $R^{35}$—$R^{47}$ and $R^{62}$—$R^{74}$ represent independently of each other —H, —$CR^{48}R^{49}R^{50}$, —$CR^{48}R^{49}$—$CR^{51}R^{52}R^{50}$, —$CR^{48}R^{49}$—$CR^{51}R^{52}$—$CR^{53}R^{54}R^{50}$, —$CR^{48}R^{49}$—$CR^{51}R^{52}$—$CR^{53}R^{54}$—$CR^{55}R^{56}R^{50}$, —F, —Cl, —Br, —I;

$R^{48}$—$R^{56}$ represent independently of each other —H, —F, —Cl, —Br, —I;

$R^4$ together with $R^{22}$ or $R^{23}$ or $R^{24}$ or $R^{25}$ may form a group —$CH_2CH_2$— or —$CH_2CH_2CH_2$— if $R^4$ is attached ortho to -L-$R^3$;

$R^2$ is

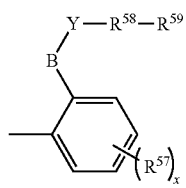

$R^{57}$ is selected from —H, —OH, —$NO_2$, —CN, —F, —Cl, —Br, —I, —$NR^{60}R^{61}$, -D-$R^{64}$, -D-$NR^{60}R^{61}$, —O-D-$R^{64}$, —CHO, —$CH_2OH$, —CO—$R^{60}$, —$CH_2OR^{60}$;

D, D' and D'' represent independently of each other —$CR^{62}R^{63}$—, —$CR^{62}R^{63}$—$CR^{65}R^{66}$—, —$CR^{62}R^{63}$—$CR^{65}R^{66}$—$CR^{67}R^{68}$—, $CR^{62}R^{63}$—$CR^{65}R^{66}$—$CR^{67}R^{68}$—$CR^{69}R^{70}$—;

$R^{60}$, $R^{61}$, $R^{75}$ and $R^{76}$ represent independently of each other —H, —$CH_3$, —$C_2H_5$, —$C_3H_7$, —$CH(CH_3)_2$, —$C_4H_9$, —$CH_2$—$CH(CH_3)_2$, —$CH(CH_3)$—$C_2H_5$, —$C(CH_3)_3$; -(cyclo-$C_3H_5$);

x is 0, 1, 2 or 3;

B is a bond, -D'-, -E-;

E and E' represent independently of each other —$CR^{62}R^{63}$—$CR^{65}R^{66}$—$CR^{67}R^{68}$—$CR^{69}R^{70}$—$CR^{71}R^{72}$—, —$CR^{62}R^{63}$—$CR^{65}R^{66}$—$CR^{67}R^{68}$—$CR^{69}R^{70}$—$CR^{71}R^{72}$—$CR^{73}R^{74}$—;

Y is a bond, —O—, —S—, —SO—, —$SO_2$—, —$SO_2NH$—, —$NHSO_2$—, —CO—, —COO—, —OOC—, —CONH—, —NHCO—, —NH—, —N($CH_3$)—, —NH—CO—NH—, —O—CO—NH—, —NH—CO—O—;

$R^{58}$ is selected from a bond, -D''-, -E'-;

$R^{59}$ is selected from (i) —H, —OH, —$OCH_3$, —$OC_2H_5$, —$OC_3H_7$, —O-cyclo-$C_3H_5$, —$OCH(CH_3)_2$, —$OC(CH_3)_3$, —$OC_4H_9$, -Ph, —OPh, —$OCH_2$-Ph, —$OCPh_3$, —SH, —$SCH_3$, —$SC_2H_5$, —$SC_3H_7$, —S-cyclo-$C_3H_5$, —$SCH(CH_3)_2$, —$SC(CH_3)_3$, —$SC_4H_9$, —$NO_2$, —F, —Cl, —Br, —I, —$P(O)(OH)_2$, —$P(O)(OCH_3)_2$, —$P(O)(OC_2H_5)_2$, —$P(O)(OCH(CH_3)_2)_2$, —$Si(CH_3)_2(C(CH_3)_3)$, —$Si(C_2H_5)_3$, —$Si(CH_3)_3$, —CN, —CHO, —$COCH_3$, —$COC_2H_5$, —$COC_3H_7$, —CO-cyclo-$C_3H_5$, —$COCH(CH_3)_2$, —$COC(CH_3)_3$, —$COC_4H_9$, —COOH, —$COOCH_3$, —$COOC_2H_5$, —$COOC_3H_7$, —$COOC_4H_9$, —COO-cyclo-$C_3H_5$, —$COOCH(CH_3)_2$, —$COOC(CH_3)_3$, —OOC—$CH_3$, —OOC—$C_2H_5$, —OOC—$C_3H_7$, —OOC—$C_4H_9$, —OOC-cyclo-$C_3H_5$, —OOC—$CH(CH_3)_2$, —OOC—$C(CH_3)_3$, —$CONR^{75}R^{76}$, —$NHCOCH_3$, —$NHCOC_2H_5$, —$NHCOC_3H_7$, —NHCO-cyclo-$C_3H_5$, —NHCO—$CH(CH_3)_2$, —$NHCOC_4H_9$, —NHCO—$C(CH_3)_3$, —NHCO—$OCH_3$, —NHCO—$OC_2H_5$, —NHCO—$OC_3H_7$, —NHCO—O-cyclo-$C_3H_5$, —NHCO—$OC_4H_9$, —NHCO—$OCH(CH_3)_2$, —NHCO—$OC(CH_3)_3$, —NHCO—$OCH_2Ph$, —$NR^{77}R^{78}$, —$SOCH_3$, —$SOC_2H_5$, —$SOC_3H_7$, —SO-cyclo-$C_3H_5$, —$SOCH(CH_3)_2$, —$SOC(CH_3)_3$, —$SO_2CH_3$, —$SO_2C_2H_5$, —$SO_2C_3H_7$, —$SO_2$-cyclo-$C_3H_5$, —$SO_2CH(CH_3)_2$, —$SO_2C_4H_9$, —$SO_2C(CH_3)_3$, —$SO_3H$, —$SO_2NR^{75}R^{76}$, —$OCF_3$, —$OC_2F_5$, —O—$COOCH_3$, —O—$COOC_2H_5$, —O—$COOC_3H_7$, —O—COO-cyclo-$C_3H_5$, —O—$COOC_4H_9$, —O—$COOCH(CH_3)_2$, —O—$COOCH_2Ph$, —O—$COOC(CH_3)_3$, —NH—CO—$NH_2$, —NH—CO—$NHCH_3$, —NH—CO—$NHC_2H_5$, —NH—CO—$NHC_3H_7$, —NH—CO—$NHC_4H_9$, —NH—CO—NH-cyclo-$C_3H_5$, —NH—CO—NH[$CH(CH_3)_2$], —NH—CO—NH[$C(CH_3)_3$], —NH—CO—N($CH_3$)$_2$, —NH—CO—N($C_2H_5$)$_2$, —NH—CO—N($C_3H_7$)$_2$, —NH—CO—N($C_4H_9$)$_2$, —NH—CO—N(cyclo-$C_3H_5$)$_2$, —NH—CO—N[$CH(CH_3)_2$]$_2$, —NH—CO—N[$C(CH_3)_3$]$_2$, —NH—C(=NH)—$NH_2$, —NH—C(=NH)—$NHCH_3$, —NH—C(=NH)—$NHC_2H_5$, —NH—C(=NH)—$NHC_3H_7$, —NH—C(=NH)—$NHC_4H_9$, —NH—C(=NH)—NH-cyclo-$C_3H_5$, —NH—C(=NH)—NH[$CH(CH_3)_2$], —NH—C(=NH)—NH[$C(CH_3)_3$], —NH—C(=NH)—N($CH_3$)$_2$, —NH—C(=NH)—N($C_2H_5$)$_2$, —NH—C(=NH)—N($C_3H_7$)$_2$, —NH—C(=NH)—N(cyclo-$C_3H_5$)$_2$, —NH—C(=NH)—N($C_4H_9$)$_2$, —NH—C(=NH)—N[$CH(CH_3)_2$]$_2$, —NH—C(=NH)—N[$C(CH_3)_3$]$_2$, —O—CO—$NH_2$, —O—CO—$NHCH_3$, —O—CO—$NHC_2H_5$, —O—CO—$NHC_3H_7$, —O—CO—$NHC_4H_9$, —O—CO—NH-cyclo-$C_3H_5$, —O—CO—NH[$CH(CH_3)_2$], —O—CO—NH[$C(CH_3)_3$], —O—CO—N($CH_3$)$_2$, —O—CO—N($C_2H_5$)$_2$, —O—CO—N($C_3H_7$)$_2$, —O—CO—N($C_4H_9$)$_2$, —O—CO—N(cyclo-$C_3H_5$)$_2$, —O—CO—N[$CH(CH_3)_2$]$_2$, —O—CO—N[$C(CH_3)_3$]$_2$, (ii) an aromatic or heteroaromatic mono- or bicyclic ring selected from 2-thienyl, 3-thienyl, 2-furanyl, 3-furanyl, 2-oxazolyl, 3-oxazolyl, 4-oxazolyl, 2-thiazolyl, 3-thiazolyl, 4-thiazolyl, 1-pyrazolyl, 3-pyrazolyl, 4-pyrazolyl, 5-pyrazolyl, 1-imidazolyl, 2-imidazolyl, 4-imidazolyl, 5-imidazolyl, phenyl, 1-naphthyl, 2-naphthyl, 2-pyridyl, 3-pyridyl, 4-pyridyl, 2-pyrimidinyl, 4-pyrimidinyl, 5-pyrimidinyl, 2-pyrazinyl, 3-pyridazinyl, 4-pyridazinyl, 1,3,5-triazin-2-yl,

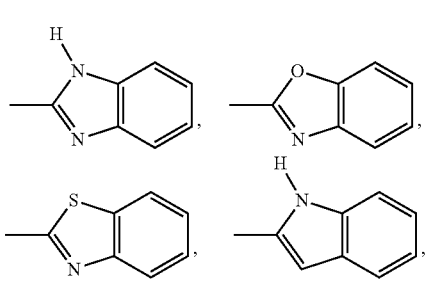

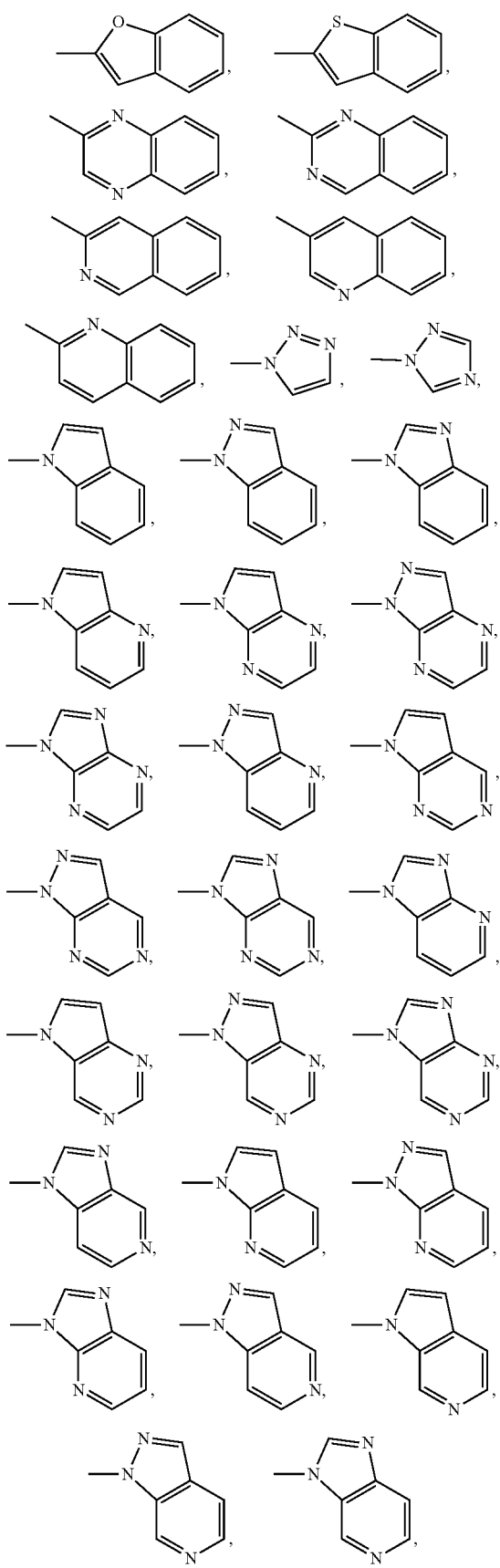

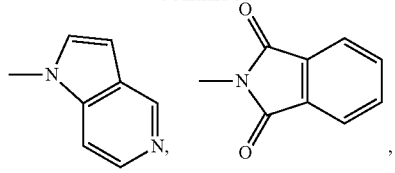

which optionally may be substituted by one or two substituents selected from —F, —Cl, —Br, —I, —OCH$_3$, —CH$_3$, —NO$_2$, —CN, —CF$_3$;

(iii) a saturated ring selected from

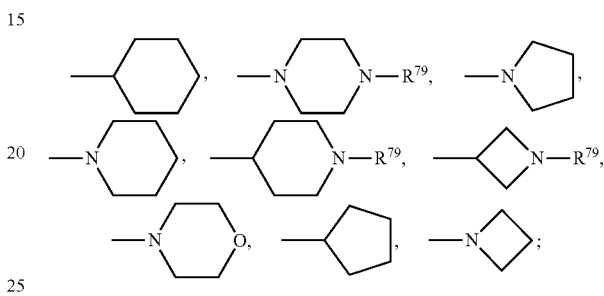

R$^{79}$ represents —H, —CH$_3$, —CH$_2$Ph, —COOC(CH$_3$)$_3$, —COOCH$_3$, —COOCH$_2$CH$_3$, —COOCH$_2$CH$_2$CH$_3$, —COOCH(CH$_3$)$_2$, —COOCH$_2$Ph, —COCH$_3$;

the group —B—Y—R$^{58}$—R$^{59}$ together with one substituent R$^{57}$ may form a group —OCH$_2$O—, if R$^{57}$ is attached in position ortho to —B—Y—R$^{58}$—R$^{59}$;

with the proviso that R$^{59}$ is not —H, if B, Y and R$^{58}$ are bonds;

and enantiomers, stereoisomeric forms, mixtures of enantiomers, diastereomers, mixtures of diastereomers, prodrugs, hydrates, solvates, acid salt forms, tautomers, and racemates of the above mentioned compounds and pharmaceutically acceptable salts thereof.

The expression prodrug is defined as a substance, which is applied in an inactive or significantly less active form. Once applied and incorporated, the prodrug is metabolized in the body in vivo into the active compound.

The expression tautomer is defined as an organic compound that is interconvertible by a chemical reaction called tautomerization. Tautomerization can be catalyzed preferably by bases or acids or other suitable compounds.

Preferred are compounds having the general formula (I):

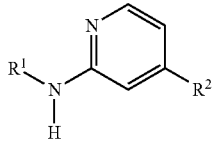

Formula (I)

wherein
R$^1$ represents

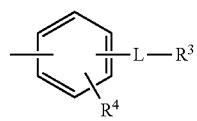

in which
L is a bond, —CH$_2$—, —CH$_2$CH$_2$—, or —CF$_2$—, particularly preferred —CH$_2$—;
R$^3$ is —SO$_2$NH$_2$, —SO$_2$NH(CH$_3$), —SO$_2$N(CH$_3$)$_2$, —SO$_2$NH(CH$_2$CH$_2$OCH$_3$), —NHSO$_2$CH$_3$, —NHSO$_2$CH$_2$CH$_3$, —NHSO$_2$CH$_2$CH$_3$, —NHSO$_2$CF$_3$, —SO$_2$CH$_3$, —NHSO$_2$NH$_2$, —SO(NH)CH$_3$, —NH$_2$, particularly preferred —SO$_2$NH$_2$;
R$^4$ is —H, —CH$_3$, —F, —Cl, or —CF$_3$, particularly preferred —H;
R$^2$ is

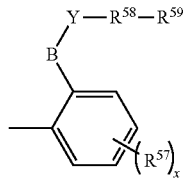

in which the group —B—Y—R$^{58}$—R$^{59}$ is —OCH$_3$, —OCH$_2$CH$_3$, —OCH$_2$CH$_2$CH$_3$, —OCH$_2$CH$_2$CH$_2$CH$_3$, —OCH(CH$_3$)$_2$, —OPh, —OCH$_2$Ph, —OCH$_2$(4-pyridyl), particularly preferred —OCH$_3$;
R$^{57}$ is —H, —F, or —Cl;
x is 0, 1, or 2.

In a further aspect of the present invention, the novel compounds according to the general formula (I) represent chiral compounds. The novel compounds according to the general formula (I) represent a racemate, or a S or a R enantiomer or a mixture of isomers.

Preferably R$^3$ represents —NO$_2$, —NH$_2$, —CN, —F, —Cl, —Br, —I, —SO$_2$R$^{22}$, —CONR$^{23}$R$^{24}$, —NR$^{25}$COR$^{22}$, —NR$^{25}$SO$_2$NR$^{23}$R$^{24}$, —NR$^{25}$SO$_2$R$^{22}$, —NR$^{25}$CONR$^{23}$R$^{24}$, —SO$_2$NR$^{23}$R$^{24}$, —SO(NR$^{26}$)R$^{22}$, or —NR$^{23}$R$^{24}$. More preferably R$^3$ represents —NO$_2$, —NH$_2$, —SO$_2$R$^{22}$, —CONR$^{23}$R$^{24}$, —NR$^{25}$COR$^{22}$, —NR$^{25}$SO$_2$NR$^{23}$R$^{24}$, —NR$^{25}$SO$_2$R$^{22}$, —NR$^{25}$CONR$^{23}$R$^{24}$, —SO$_2$NR$^{23}$R$^{24}$, —SO(NR$^{26}$)R$^{22}$, or —NR$^{23}$R$^{24}$. Most preferably R$^3$ represents —NO$_2$, —NH$_2$, —SO$_2$R$^{22}$, —NR$^{25}$COR$^{22}$, —NR$^{25}$SO$_2$R$^{22}$, or —SO$_2$NR$^{23}$R$^{24}$.

It is also preferred if L represents a bond, —CH$_2$—, —CH$_2$CH$_2$—, or —CF$_2$—. More preferably L represents a bond, —CH$_2$—, or —CH$_2$CH$_2$—.

The residue-L-R$^3$ represents preferably —NO$_2$, —NH$_2$, —SO$_2$R$^{22}$, —CONR$^{23}$R$^{24}$, —NR$^{25}$COR$^{22}$, —NR$^{25}$SO$_2$NR$^{23}$R$^{24}$, —NR$^{25}$SO$_2$R$^{22}$, —NR$^{25}$CONR$^{23}$R$^{24}$, —SO$_2$NR$^{23}$R$^{24}$, —SO(NR$^{26}$)R$^{22}$, —NR$^{23}$R$^{24}$, —CH$_2$—NO$_2$, —CH$_2$—NH$_2$, —CH$_2$—SO$_2$R$^{22}$, —CH$_2$—CONR$^{23}$R$^{24}$, —CH$_2$—NR$^{25}$COR$^{22}$, —CH$_2$—NR$^{25}$SO$_2$NR$^{23}$R$^{24}$, —CH$_2$—NR$^{25}$SO$_2$R$^{22}$, —CH$_2$—NR$^{25}$CONR$^{23}$R$^{24}$, —CH$_2$—SO$_2$NR$^{23}$R$^{24}$, —CH$_2$—SO(NR$^{26}$)R$^{22}$, —CH$_2$—NR$^{23}$R$^{24}$, —CH$_2$CH$_2$—NO$_2$, —CH$_2$CH$_2$—NH$_2$, —CH$_2$CH$_2$—SO$_2$R$^{22}$, —CH$_2$CH$_2$—CONR$^{23}$R$^{24}$, —CH$_2$CH$_2$—NR$^{25}$COR$^{22}$, —CH$_2$CH$_2$—NR$^{25}$SO$_2$NR$^{23}$R$^{24}$, —CH$_2$CH$_2$—NR$^{25}$SO$_2$R$^{22}$, —CH$_2$CH$_2$—NR$^{25}$CONR$^{23}$R$^{24}$, —CH$_2$CH$_2$—SO$_2$NR$^{23}$R$^{24}$, —CH$_2$CH$_2$—SO(NR$^{26}$)R$^{22}$, or —CH$_2$CH$_2$—NR$^{23}$R$^{24}$. More preferably the residue-L-R$^3$ represents preferably —NO$_2$, —NH$_2$, —SO$_2$R$^{22}$, —NR$^{25}$COR$^{22}$, —NR$^{25}$SO$_2$R$^{22}$, —SO$_2$NR$^{23}$R$^{24}$, —CH$_2$—NO$_2$, —CH$_2$—NH$_2$, —CH$_2$—SO$_2$R$^{22}$, —CH$_2$—NR$^{25}$COR$^{22}$, —CH$_2$—NR$^{25}$SO$_2$R$^{22}$, —CH$_2$—SO$_2$NR$^{23}$R$^{24}$, —CH$_2$CH$_2$—NO$_2$, —CH$_2$CH$_2$—NH$_2$, —CH$_2$CH$_2$—SO$_2$R$^{22}$, —CH$_2$CH$_2$—NR$^{25}$COR$^{22}$, —CH$_2$CH$_2$—NR$^{25}$SO$_2$R$^{22}$, or —CH$_2$CH$_2$—SO$_2$NR$^{23}$R$^{24}$.

The following general formula are also especially preferred:

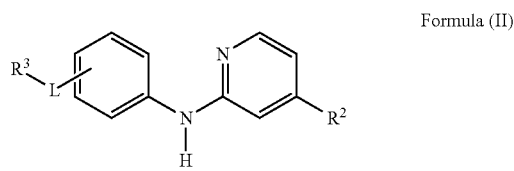

Formula (II)

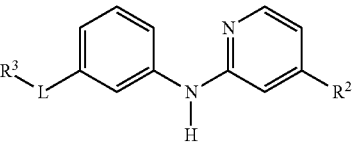

Formula (III)

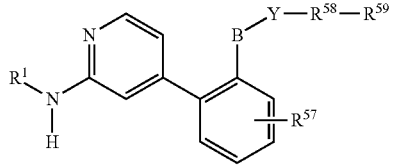

Formula (IV)

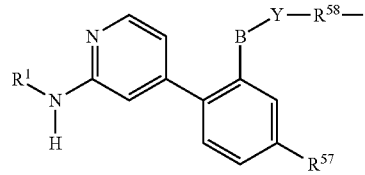

Formula (V)

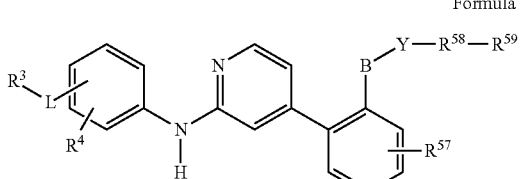

Formula (VI)

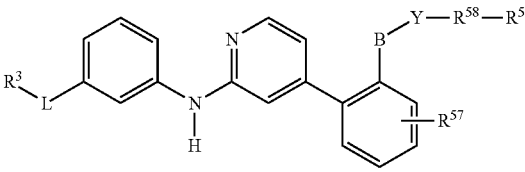

Formula (VII)

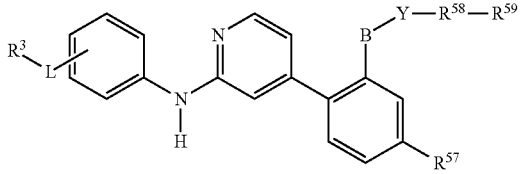

Formula (VIII)

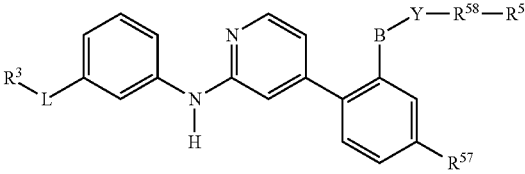

Formula (IX)

wherein -L-R$^3$, —R$^4$, —B—Y—R$^{58}$—R$^{59}$ and —R$^{57}$ have the meanings as defined herein.

Moreover in all general formulas disclosed herein the residue-L-R³ represents more preferably —NO₂, —NH₂, —SO₂R²², —CONHR²³, —CON(R²³)₂, —NHCOR²², —NHSO₂NHR²³, —NHSO₂N(R²³)₂, —NHSO₂R²², —NHCONHR²³, —NHCON(R²³)₂, —SO₂NHR²³, —SO₂N(R²³)₂, —SO(NH)R²², —NHR²³, —N(R²³)₂, —CH₂—NO₂, —CH₂—NH₂, —CH₂—SO₂R²², —CH₂—CONHR²³, —CH₂—CON(R²³)₂, —CH₂—NHCOR²², —CH₂—NHSO₂NHR²³, —CH₂—NHSO₂N(R²³)₂, —CH₂—NHSO₂R²², —CH₂—NHCONHR²³, —CH₂—NHCON(R²³)₂, —CH₂—SO₂NHR²³, —CH₂—SO₂N(R²³)₂, —CH₂—SO(NH)R²², —CH₂—NHR²³, —CH₂—N(R²³)₂, —CH₂CH₂—NO₂, —CH₂CH₂—NH₂, —CH₂—CH₂—SO₂R²², —CH₂—CH₂—NHSO₂NHR²³, —CH₂—CH₂—NHSO₂N(R²³)₂, —CH₂—CH₂—NHSO₂R²², —CH₂—CH₂—NHCONHR²³, —CH₂—CH₂—NHCON(R²³)₂, —CH₂—CH₂—SO₂NHR²³, —CH₂—CH₂—SO₂N(R²³)₂, —CH₂—CH₂—SO(NH)R²², —CH₂—CH₂—NHR²³, —CH₂—CH₂—N(R²³)₂, —CH₂—CH₂—CONHR²³, —CH₂—CH₂—CON(R²³)₂, or —CH₂—CH₂—NHCOR²². In addition it is preferred if the residue-L-R³ is attached in meta-position of the aniline moiety of the general formulas (I), (II), (IV), (V), (VI) and (VIII).

Still more preferably are the compounds of general formula (III)

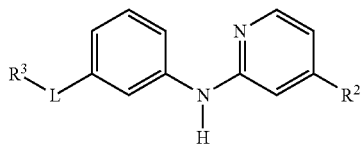

wherein
-L-R³ represents —NO₂, —NH₂, —NH(CH₃), —NH(C₂H₅), —NH(C₃H₇), —N(CH₃)₂, —N(C₂H₅)₂, —N(C₃H₇)₂, —SO₂CH₃, —SO₂C₂H₅, —SO₂C₃H₇, —CONH₂, —CONH(CH₃), —CONH(C₂H₅), —CONH(C₃H₇), —CON(CH₃)₂, —CON(C₂H₅)₂, —CON(C₃H₇)₂, —NHCOCH₃, —NHCOC₂H₅, —NHCOC₃H₇, —NHSO₂NH₂, —NHSO₂NH(CH₃), —NHSO₂NH(C₂H₅), —NHSO₂NH(C₃H₇), —NHSO₂N(CH₃)₂, —NHSO₂N(C₂H₅)₂, —NHSO₂N(C₃H₇)₂, —NHSO₂CH₃, —NHSO₂C₂H₅, —NHSO₂C₃H₇, —NHCONH₂, —NHCONH(CH₃), —NHCONH(C₂H₅), —NHCONH(C₃H₇), —NHCON(CH₃)₂, —NHCON(C₂H₅)₂, —NHCON(C₃H₇)₂, —SO₂NH₂, —SO₂NH(CH₃), —SO₂NH(C₂H₅), —SO₂NH(C₃H₇), —SO₂N(CH₃)₂, —SO₂N(C₂H₅)₂, —SO₂N(C₃H₇)₂, —SO(NH)CH₃, —SO(NH)C₂H₅, —SO(NH)C₃H₇, —CH₂—NO₂, —CH₂—NH₂, —CH₂—NH(CH₃), —CH₂—NH(C₂H₅), —CH₂—NH(C₃H₇), —CH₂—N(CH₃)₂, —CH₂—N(C₂H₅)₂, —CH₂—N(C₃H₇)₂, —CH₂—SO₂CH₃, —CH₂—SO₂C₂H₅, —CH₂—SO₂C₃H₇, —CH₂—CONH₂, —CH₂—CONH(CH₃), —CH₂—CONH(C₂H₅), —CH₂—CONH(C₃H₇), —CH₂—CON(CH₃)₂, —CH₂—CON(C₂H₅)₂, —CH₂—CON(C₃H₇)₂, —CH₂—NHCOCH₃, —CH₂—NHCOC₂H₅, —CH₂—NHCOC₃H₇, —CH₂—NHSO₂NH₂, —CH₂—NHSO₂NH(CH₃), —CH₂—NHSO₂NH(C₂H₅), —CH₂—NHSO₂NH(C₃H₇), —CH₂—NHSO₂N(CH₃)₂, —CH₂—NHSO₂N(C₂H₅)₂, —CH₂—NHSO₂N(C₃H₇)₂, —CH₂—NHSO₂CH₃, —CH₂—NHSO₂C₂H₅, —CH₂—NHSO₂C₃H₇, —CH₂—NHCONH₂, —CH₂—NHCONH(CH₃), —CH₂—NHCONH(C₂H₅), —CH₂—NHCONH(C₃H₇), —CH₂—NHCON(CH₃)₂, —CH₂—NHCON(C₂H₅)₂, —CH₂—NHCON(C₃H₇)₂, —CH₂—SO₂NH₂, —CH₂—SO₂NH(CH₃), —CH₂—SO₂NH(C₂H₅), —CH₂—SO₂NH(C₃H₇)₂, —CH₂—SO₂N(CH₃)₂, —CH₂—SO(NH)CH₃, —CH₂—SO(NH)C₂H₅, —CH₂—SO(NH)C₃H₇, —CH₂CH₂—NO₂, —CH₂CH₂—NH₂, —CH₂—CH₂—NH(CH₃), —CH₂—CH₂—NH(C₂H₅), —CH₂—CH₂—NH(C₃H₇), —CH₂—CH₂—N(CH₃)₂, —CH₂—CH₂—N(C₂H₅)₂, —CH₂—CH₂—N(C₃H₇)₂, —CH₂—CH₂—SO₂CH₃, —CH₂—CH₂—SO₂C₂H₅, —CH₂—CH₂—SO₂C₃H₇, —CH₂—CH₂—CONH₂, —CH₂—CH₂—CONH(CH₃), —CH₂—CH₂—CONH(C₂H₅), —CH₂—CH₂—CONH(C₃H₇), —CH₂—CH₂—CON(CH₃)₂, —CH₂—CH₂—CON(C₂H₅)₂, —CH₂—CH₂—CON(C₃H₇)₂, —CH₂—CH₂—NHCOCH₃, —CH₂—CH₂—NHCO₂H₅, —CH₂—CH₂—NHCO₃H₇, —CH₂—CH₂—NHSO₂NH₂, —CH₂—CH₂—NHSO₂NH(CH₃), —CH₂—CH₂—NHSO₂NH(C₂H₅), —CH₂—CH₂—NHSO₂NH(C₃H₇), —CH₂—CH₂—NHSO₂N(CH₃)₂, —CH₂—CH₂—NHSO₂N(C₂H₅)₂, —CH₂—CH₂—NHSO₂N(C₃H₇)₂, —CH₂—CH₂—NHSO₂CH₃, —CH₂—CH₂—NHSO₂C₂H₅, —CH₂—CH₂—NHSO₂C₃H₇, —CH₂—CH₂—NHCONH₂, —CH₂—CH₂—NHCONH(CH₃), —CH₂—CH₂—NHCONH(C₂H₅), —CH₂—CH₂—NHCONH(C₃H₇), —CH₂—CH₂—NHCON(CH₃)₂, —CH₂—CH₂—NHCON(C₂H₅)₂, —CH₂—CH₂—NHCON(C₃H₇)₂, —CH₂—CH₂—SO₂NH₂, —CH₂—CH₂—SO₂NH(CH₃), —CH₂—CH₂—SO₂NH(C₂H₅), —CH₂—CH₂—SO₂NH(C₃H₇)₂, —CH₂—CH₂—SO₂N(CH₃)₂, —CH₂—CH₂—SO₂N(C₂H₅)₂, —CH₂—CH₂—SO₂N(C₃H₇)₂, —CH₂—CH₂—SO(NH)CH₃, —CH₂—CH₂—SO(NH)C₂H₅, —CH₂—CH₂—SO(NH)C₃H₇, and wherein R² has the meanings as defined herein.

In general formulas (I), (IV), (V) and (VI) it is preferred that R⁴ represents hydrogen.

Moreover it is especially preferred if the substituent-L-R³ represents —NO₂, —NH₂, —SO₂NH₂, —SO₂—NH—C(CH₃)₃, —SO₂CH₃, —CH₂—SO₂NH₂, —CH₂—SO₂—N(CH₃)₂, —CH₂—CH₂—SO₂NH₂, —NHSO₂CH₃, —NHCOCH₃, or —CH₂—SO₂—NH(CH₂CH₂CH₃).

Furthermore it is preferred if R⁵⁷ represents —NO₂, —CN, —F, —Cl, —Br, and it is more preferred if R⁵⁷ represents —NO₂, —F, —Cl, and it is especially preferred if R⁵⁷ represents —F. Moreover in general formulas (I), (II), (III), (IV), (VI) and (VII) it is preferred if R⁵⁷ is attached in position 4 of the phenyl residue R² or in para position to the linkage of the phenyl residue R² to the pyridyl ring or in meta position to the substituent —B—Y—R⁵⁸—R⁵⁹.

The residue —B—Y—R⁵⁸—R⁵⁹ is most preferably an alkoxy group with 1 to 4 carbon atoms and more preferably —OCH₃, —OC₂H₅, —OC₃H₇ or —OC₄H₉ and most preferably —OCH₃.

R² is preferably 2-methoxyphenyl, 4-fluoro-2-methoxyphenyl, or 6-fluoro-2-methoxyphenyl.

In yet another preferred embodiment of the present invention, the compound according to the general formula (I) is selected from the group of compounds depicted in the following Table 1.

TABLE 1

| Compound No. | Structure | Nomenclature |
| --- | --- | --- |
| B1 | 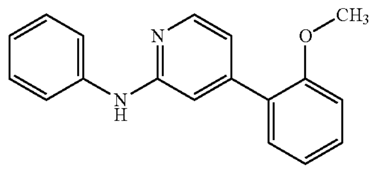 [SMILES: COc1ccccc1-c1ccnc(Nc2ccccc2)c1] | 4-(2-Methoxyphenyl)-N-phenylpyridin-2-amine |
| C1 | 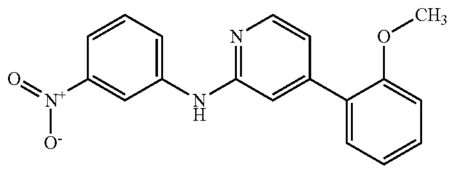 [SMILES: COc1ccccc1-c1ccnc(Nc2cccc([N+](=O)[O-])c2)c1] | 4-(2-Methoxyphenyl)-N-(3-nitrophenyl)pyridin-2-amine |
| C2 | 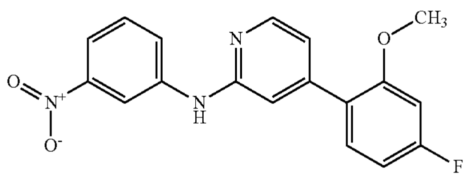 [SMILES: COc1cc(F)ccc1-c1ccnc(Nc2cccc([N+](=O)[O-])c2)c1] | 4-(4-Fluoro-2-methoxyphenyl)-N-(3-nitrophenyl)pyridin-2-amine |
| D1 | 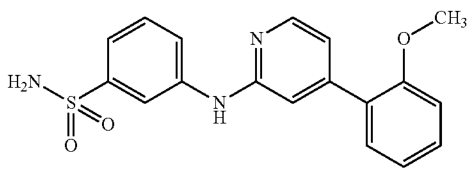 | 3-[(4-(2-Methoxyphenyl)pyridin-2-yl)amino]benzenesulfonamide |
| D2 | 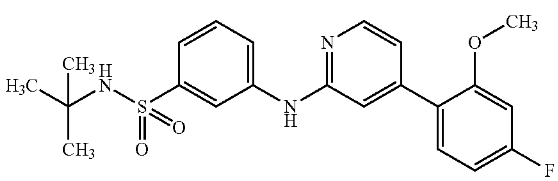 [SMILES: COc1cc(F)ccc1-c1ccnc(Nc2cccc(S(=O)(=O)NC(C)(C)C)c2)c1] | N-(tert-Butyl)-3-[(4-(4-fluoro-2-methoxyphenyl)pyridin-2-yl)amino]benzenesulfonamide |
| E1 | 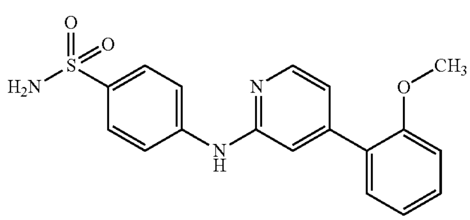 [SMILES: COc1ccccc1-c1ccnc(Nc2ccc(S(N)(=O)=O)cc2)c1] | 4-[(4-(2-Methoxyphenyl)pyridin-2-yl)amino]benzenesulfonamide |
| F1 | 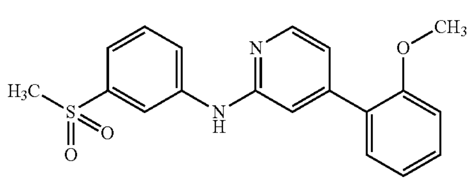 | 4-(2-Methoxyphenyl)-N-(3-(methylsulfonyl)phenyl)-pyridin-2-amine |
| G1 | 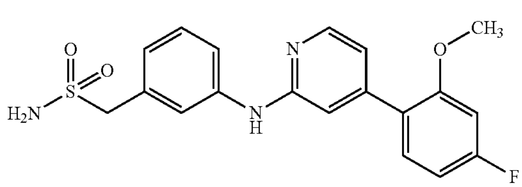 [SMILES: COc1cc(F)ccc1-c1ccnc(Nc2cccc(CS(N)(=O)=O)c2)c1] | 3-((4-(4-Fluoro-2-methoxyphenyl)pyridin-2-yl)amino)phenylmethanesulfonamide |

TABLE 1-continued

| Compound No. | Structure | Nomenclature |
|---|---|---|
| G2 | 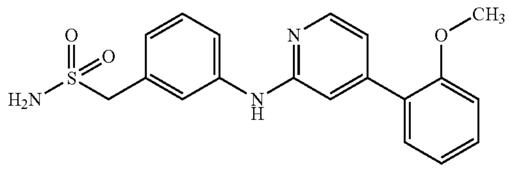 [SMILES: COc1ccccc1-c1ccnc(Nc2cccc(CS(N)(=O)=O)c2)c1] | [3-((4-(2-Methoxyphenyl)pyridin-2-yl)amino)phenyl]methanesulfonamide |
| G3 | 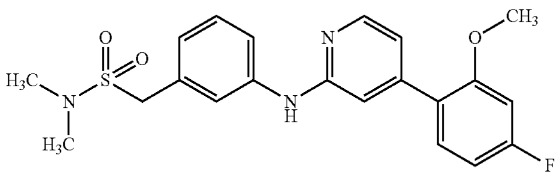 [SMILES: COc1cc(F)ccc1-c1ccnc(Nc2cccc(CS(=O)(=O)N(C)C)c2)c1] | 1-[3-((4-(4-Fluoro-2-methoxyphenyl)pyridin-2-yl)amino)phenyl]-N,N-dimethylmethanesulfonamide |
| H1 | 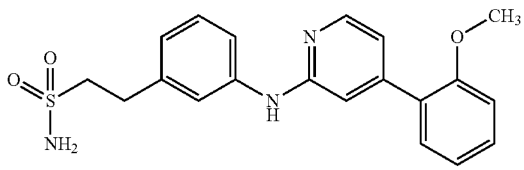 [SMILES: COc1ccccc1-c1ccnc(Nc2cccc(CCS(N)(=O)=O)c2)c1] | 2-[3-((4-(2-Methoxyphenyl)pyridin-2-yl)amino)phenylethanesulfonamide |
| I1 | 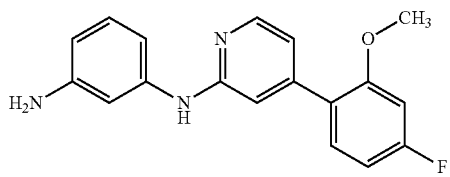 [SMILES: COc1cc(F)ccc1-c1ccnc(Nc2cccc(N)c2)c1] | $N^1$-(4-(4-Fluoro-2-methoxyphenyl)pyridin-2-yl)benzene-1,3-diamine |
| J1 | 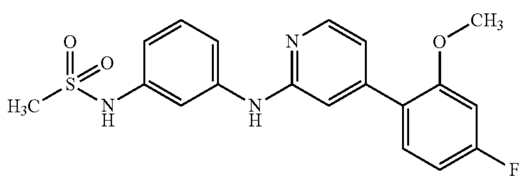 [SMILES: COc1cc(F)ccc1-c1ccnc(Nc2cccc(NS(C)(=O)=O)c2)c1] | N-[3-((4-(4-Fluoro-2-methoxyphenyl)pyridin-2-yl)amino)phenyl]methanesulfonamide |
| J2 | 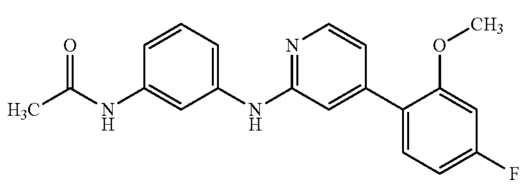 [SMILES: COc1cc(F)ccc1-c1ccnc(Nc2cccc(NC(C)=O)c2)c1] | N-[3-((4-(4-Fluoro-2-methoxyphenyl)pyridin-2-yl)amino)phenyl]acetamide |
| K1 | 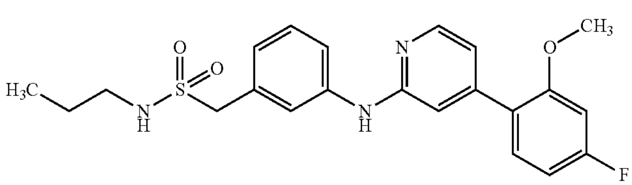 [SMILES: CCCNS(=O)(=O)Cc1cccc(Nc2cc(-c3ccc(F)cc3OC)ccn2)c1] | 1-[3-((4-(4-Fluoro-2-methoxyphenyl)pyridin-2-yl)amino)phenyl]-N-propylmethanesulfonamide |

The compounds of the present invention may form salts with organic or inorganic acids or bases. Examples of suitable acids for such acid addition salt formation are hydrochloric acid, hydrobromic acid, sulfuric acid, phosphoric acid, acetic acid, citric acid, oxalic acid, malonic acid, salicylic acid, p-aminosalicylic acid, malic acid, fumaric acid, succinic acid, ascorbic acid, maleic acid, sulfonic acid, phosphonic acid, perchloric acid, nitric acid, formic acid, propionic acid, gluconic acid, lactic acid, tartaric acid, hydroxymaleic acid, pyruvic acid, phenylacetic acid, benzoic acid, p-aminobenzoic acid, p-hydroxybenzoic acid, methanesulfonic acid, ethanesulfonic acid, nitrous acid, hydroxyethanesulfonic acid, ethylenesulfonic acid, p-toluenesulfonic acid, naphthylsulfonic acid, sulfanilic acid, camphorsulfonic acid, china acid, mandelic acid, o-methylmandelic acid, hydrogen-benzenesulfonic acid, picric acid, adipic acid, d-o-tolyltartaric acid, tartronic acid, (o, m, p)-toluic acid, naphthylamine sulfonic acid, trifluoroacetic acid, and other mineral or carboxylic acids well known to those skilled in the art. The salts are prepared by contacting the free base form with a sufficient amount of the desired acid to produce a salt in the conventional manner.

In the case the inventive compounds bear acidic groups, salts could also be formed with inorganic or organic bases. Examples for suitable inorganic or organic bases are, for example, NaOH, KOH, NH$_4$OH, tetraalkylammonium hydroxide, lysine or arginine and the like. Salts may be prepared in a conventional manner using methods well known in the art, for example by treatment of a solution of the compound of the general formula (I) with a solution of an acid, selected out of the group mentioned above.

Syntheses of Compounds

The synthesis of the inventive disubstituted pyridines according to the present invention is preferably carried out according to the general synthetic sequences, shown in Schemes 1 and 2.

with water and ethanol, and in the presence of a base like sodium bicarbonate, sodium carbonate, potassium carbonate, or K$_3$PO$_4$. Preferred methods use Pd(PPh$_3$)$_4$ in a mixture of DME and water in the presence of potassium carbonate, Pd(PPh$_3$)$_2$Cl$_2$ in a mixture of DME and water in the presence of potassium carbonate, or Pd(dppf)Cl$_2$ in a mixture of dioxane and water in the presence of K$_3$PO$_4$. Heating may be carried out by a microwave oven.

The intermediates (III) may also be prepared by coupling of boronic acid derivatives (RO)$_2$B—R$^2$ with 4-halopyridines (IV), preferred with 4-bromopyridine or 4-chloropyridine, followed by N-oxidation of the resulting 4-arylpyridine intermediate (V). Various methods to oxidize pyridines to its corresponding N-oxides are known to those skilled in the art. Preferred methods use m-chloroperbenzoic acid (MCPBA) in dichloromethane or hydrogenperoxide in the presence of Scheme 1

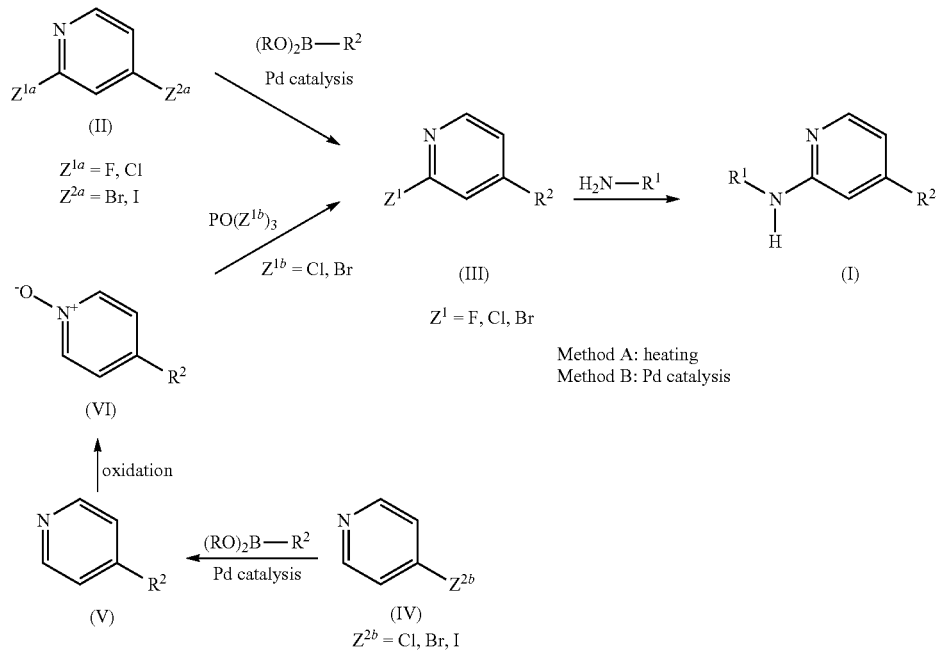

Method A: heating
Method B: Pd catalysis

In a first step a 2,4-dihalo-pyridine (II) is reacted with a boronic acid derivative (RO)$_2$B—R$^2$ to give 2-halo-pyridine intermediates (III). Preferred intermediates (II) are 4-bromo-2-chloro-pyridine or 2-fluoro-4-iodo-pyridine. The boronic acid derivative may be a boronic acid (R=—H) or an ester of the boronic acid, e.g. its isopropyl ester (R=—CH(CH$_3$)$_2$), preferably an ester derived from pinacol in which the boronic acid intermediate forms a 2-aryl-4,4,5,5-tetramethyl-1,3,2-dioxaborolane (R—R=—C(CH$_3$)$_2$—C(CH$_3$)$_2$—).

The coupling reaction is catalyzed by Pd catalysts, e.g. by Pd(0) catalysts like tetrakis(triphenylphosphine)palladium (0) [Pd(PPh$_3$)$_4$], tris(dibenzylideneacetone)-dipalladium(0) [Pd$_2$(dba)$_3$], or by Pd(II) catalysts like dichlorobis(triphenylphosphine)-palladium(II) [Pd(PPh$_3$)$_2$Cl$_2$], palladium(II) acetate in the presence of triphenylphosphine or [1,1'-bis (diphenylphosphino)ferrocene]palladium dichloride [Pd(dppf)Cl$_2$].

The reaction is preferably carried out by heating in a solvent like dioxane, DMF (dimethylformamide), DME (1,2-dimethoxyethane), THF (tetrahydrofuran), or isopropanol, more preferred in a mixture of such a solvent with water or methyltrioxorhenium(VII) as a catalyst. The resulting pyridine-N-oxide (VI) is heated with POCl$_3$ or POBr$_3$ to give the 2-chloro-pyridine or 2-bromopyridine intermediates (III), respectively.

Disubstituted pyridines of Formula (I) are prepared by reaction of 2-halopyridines (III) with an aniline H$_2$N—R$^1$. The reaction may be carried out without a catalyst (Method A) or in the presence of a transition metal catalyst, preferably in the presence of a Pd or Cu catalyst, e.g. CuI, more preferred in the presence of a Pd catalyst (Method B).

Reactions of Method A are preferably carried out with 2-fluoropyridines (Z$^1$=F) or with 2-chloropyridines (Z$^1$=Cl). Both reactants, the 2-halopyridine (III) and the aniline H$_2$N—R$^1$ are heated at temperature above 80° C., preferably at a temperature of about 150° C. The reaction may be carried out in an inert solvent like dioxane, DME, DMF, toluene, or xylene, optionally in the presence of an additional base like sodium carbonate, potassium carbonate, cesium carbonate, sodium hydride, triethylamine, N,N-diisopropylethylamine, NaOC(CH$_3$)$_3$, KOC(CH$_3$)$_3$, or KN(Si(CH$_3$)$_3$)$_2$. Preferably it is carried out by heating in a microwave oven at a temperature of about 150° C., either neat without a solvent and without an additional base or in DMF in the presence of cesium carbonate.

Reactions according to Method B are preferably carried out with 2-chloropyridines ($Z^1$=Cl) or with 2-bromopyridines ($Z^1$=Br). Pd catalysts are selected from Pd(0) catalysts like tetrakis(triphenylphosphine)palladium(0) [Pd(PPh$_3$)$_4$], tris(dibenzylideneacetone)dipalladium(0) [Pd$_2$(dba)$_3$], or from Pd(II) catalysts like dichlorobis(triphenylphosphine)palladium(II) [Pd(PPh$_3$)$_2$Cl$_2$], palladium(II) chloride, palladium(II)acetate, or dichlorobis(acetonitrile)palladium(II) [PdCl$_2$(CH$_3$CN)$_2$], preferably in the presence of an additional phosphine ligand. The reaction is carried out in an inert solvent like DMF, toluene, xylene, dioxane, or DME and in the presence of a base like sodium hydride, sodium carbonate, cesium carbonate, NaOC(CH$_3$)$_3$, or KOC(CH$_3$)$_3$. Preferred methods which employ Pd$_2$(dba)$_3$ as a catalyst use heating in xylene, toluene, DMF, or dioxane in the presence of ligands like ([1,1'-biphenyl]-2-yl)dicyclohexylphosphine, 2,8,9-triisobutyl-2,5,8,9-tetraaza-1-phosphabicyclo[3.3.3]undecane, dicyclohexyl-[2'-(dimethylamino)biphenyl-2-yl]phosphine, or 1,1'-bis(diphenylphosphino)ferrocene and a base like NaOC(CH$_3$)$_3$; which employ palladium(II) acetate use heating in toluene, xylene, or DMF in the presence of 2,2'-bis(diphenylphosphino)biphenyl or [1,1'-binaphthalene]-2,2'-diyl-bis(diphenylphosphine) [BINAP] and a base like NaOC(CH$_3$)$_3$; which employ palladium(II)chloride use heating in toluene or xylene in the presence of 4,5-bis(diphenylphosphino)-9,9-dimethylxanthene [Xantphos] and a base like NaOC(CH$_3$)$_3$; which employ PdCl$_2$(CH$_3$CN)$_2$ use heating in DMF in the presence of a ligand like 4,5-bis(diphenylphosphino)-9,9-dimethylxanthene [Xantphos], [1,1'-binaphthalene]-2,2'-diyl-bis(3,5-xylyl-phosphine) [(R)-3,5-xylyl-BINAP], 2-(dicyclohexylphosphino)-2',6'-di-isopropoxy-1,1'-biphenyl [Ruphos], or 2-(dicyclohexylphosphino)-2',4',6'-triisopropyl-1,1'-biphenyl [Xphos] and a base like NaOC(CH$_3$)$_3$. In a more preferred method the coupling reaction is carried out by heating in DMF with PdCl$_2$(CH$_3$CN)$_2$ and Xantphos in the presence of NaOC(CH$_3$)$_3$.

The synthesis of pyridines of Formula (I) may be carried out in the inverse order of the reaction steps compared to Scheme 1, in such a manner that in a first step a 2,4-dihalopyridine (II) is reacted with an aniline H$_2$N—R$^1$ followed in a second step by the reaction of the intermediate pyridine (VII) with a boronic acid derivative (RO)$_2$B—R$^2$. The sequence may be carried out without isolation of the intermediate pyridine (VII).

Several compounds of Formula (I) may be prepared by converting substituents which are attached to the aromatic rings R$^1$ and/or R$^2$ to other substituents using standard reactions which are known to the person skilled in the art. For example, a nitro group can be reduced to an amino group, such an amino group can be converted to a sulfonamide by reaction with a sulfonyl chloride, to a carboxamide by reaction with a carbonyl chloride or another activated derivative of a carboxylic acid, to an urea by reaction with an isocyanate. Carbamate substituents may be cleaved to amino groups, in particular tert-butyl carbamates by reaction with acids like trifluoroacetic acid or hydrochloric acid. Formyl groups may be converted to aminomethyl groups by reaction with primary amines under conditions of a reductive amination. Benzylic N,N-dialkyl- or N-monoalkyl-sulfonamides may be prepared by reaction of a corresponding N-substituted sulfonamide, preferably of a N,N-dimethyl-, a N,N-diphenyl-, or a N-methyl-N-phenyl-sulfonamide, with a primary or secondary amine, respectively.

In a further aspect of the present invention, the novel compounds according to the general formula (I) are used as pharmaceutically active agent.

Pharmaceutical Compositions and Drug Combinations

Another aspect of the present invention relates to drug combinations and pharmaceutical compositions comprising at least one compound of general formula (I) as active ingredient together with at least one pharmaceutically acceptable carrier, excipient and/or diluent and optionally together with one or more other anti-tumor agents or with one or more anti-retroviral drugs. As used herein the term "drug combination" refers to a combination of at least to pharmaceutically active agents or therapeutic agents with or without further ingredients, carrier, diluents and/or solvents. As used herein the term "pharmaceutical composition" refers to a galenic formulation of at least one pharmaceutically active agent together with at least one further ingredient, carrier, diluent and/or solvent.

Compounds of formula (I) may be administered as the sole pharmaceutical agent or in combination with one or more additional therapeutic agents, wherein the drug combination causes no unacceptable adverse effects. This combination therapy includes administration of a single pharmaceutical dosage formulation, which contains a compound of formula (I) and one or more additional therapeutic agents in form of a single pharmaceutical composition, as well as administration of the compound of formula (I) and each additional therapeutic agent in its own separate pharmaceutical dosage formulation, i.e. in its own separate pharmaceutical composition. For example, a compound of formula (I) and a therapeutic agent may be administered to the patient together in a single oral dosage composition such as a tablet or capsule, or each agent may be administered in separate pharmaceutical compositions.

Where separate pharmaceutical compositions are used, the compound of formula (I) and one or more additional therapeutic agents may be administered at essentially the same time (e.g., concurrently) or at separately staggered times (e.g., sequentially).

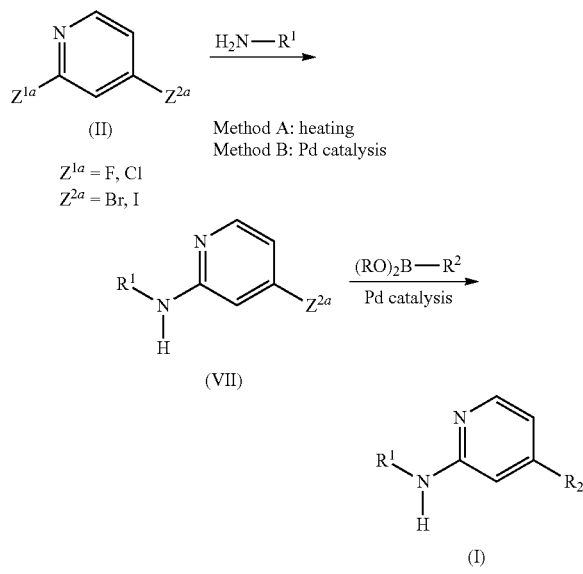

Scheme 2

In particular, the compounds of the present invention may be used in fixed or separate pharmaceutical compositions with other anti-tumor agents such as alkylating agents, anti-metabolites, plant-derived anti-tumor agents, hormonal therapy agents, topoisomerase inhibitors, camptothecin derivatives, kinase inhibitors, targeted drugs, antibodies, interferons and/or biological response modifiers, anti-angiogenic compounds, and other anti-tumor drugs. In this regard, the following is a non-limiting list of examples of secondary agents that may be used in combination with the compounds of the present invention:

Alkylating agents include, but are not limited to, nitrogen mustard N-oxide, cyclophosphamide, ifosfamide, thiotepa, ranimustine, nimustine, temozolomide, altretamine, apaziquone, brostallicin, bendamustine, carmustine, estramustine, fotemustine, glufosfamide, mafosfamide, and mitolactol; platinum-coordinated alkylating compounds include, but are not limited to, cisplatin, carboplatin, eptaplatin, lobaplatin, nedaplatin, oxaliplatin, and satraplatin;

Anti-metabolites include, but are not limited to, methotrexate, 6-mercaptopurine riboside, mercaptopurine, 5-fluorouracil alone or in combination with leucovorin, tegafur, doxifluridine, carmofur, cytarabine, cytarabine ocfosfate, enocitabine, gemcitabine, fludarabin, 5-azacitidine, capecitabine, cladribine, clofarabine, decitabine, eflornithine, ethynylcytidine, cytosine arabinoside, hydroxyurea, melphalan, nelarabine, nolatrexed, ocfosfite, disodium premetrexed, pentostatin, peliterxol, raltitrexed, triapine, trimetrexate, vidarabine, vincristine, and vinorelbine;

Hormonal therapy agents include, but are not limited to, exemestane, Lupron, anastrozole, doxercalciferol, fadrozole, formestane, 11-beta hydroxysteroid dehydrogenase 1 inhibitors, 17-alpha hydroxylase/17,20 lyase inhibitors such as abiraterone acetate, 5-alpha reductase inhibitors such as finasteride and episteride, anti-estrogens such as tamoxifen citrate and fulvestrant, Trelstar, toremifene, raloxifene, lasofoxifene, letrozole, anti-androgens such as bicalutamide, flutamide, mifepristone, nilutamide, Casodex, and anti-progesterones and combinations thereof;

Plant-derived anti-tumor substances include, e.g., those selected from mitotic inhibitors, for example epothilones such as sagopilone, ixabepilone and epothilone B, vinblastine, vinflunine, docetaxel, and paclitaxel;

Cytotoxic topoisomerase inhibiting agents include, but are not limited to, aclarubicin, doxorubicin, amonafide, belotecan, camptothecin, 10-hydroxycam ptothecin, 9-aminocam ptothecin, diflomotecan, irinotecan, topotecan, edotecarin, epimbicin, etoposide, exatecan, gimatecan, lurtotecan, mitoxantrone, pirambicin, pixantrone, rubitecan, sobuzoxane, tafluposide, and combinations thereof;

Immunologicals include interferons such as interferon alpha, interferon alpha-2a, interferon alpha-2b, interferon beta, interferon gamma-1a and interferon gamma-n1, and other immune enhancing agents such as L19-IL2 and other IL2 derivatives, filgrastim, lentinan, sizofilan, TheraCys, ubenimex, aldesleukin, alemtuzumab, BAM-002, dacarbazine, daclizumab, denileukin, gemtuzumab, ozogamicin, ibritumomab, imiquimod, lenograstim, lentinan, melanoma vaccine (Corixa), molgramostim, sargramostim, tasonermin, tecleukin, thymalasin, tositumomab, Vimlizin, epratuzumab, mitumomab, oregovomab, pemtumomab, and Provenge; Merial melanoma vaccine;

Biological response modifiers are agents that modify defense mechanisms of living organisms or biological responses such as survival, growth or differentiation of tissue cells to direct them to have anti-tumor activity; such agents include, e.g., krestin, lentinan, sizofiran, picibanil, ProMune, and ubenimex;

Anti-angiogenic compounds include, but are not limited to, acitretin, aflibercept, angiostatin, aplidine, asentar, axitinib, recentin, bevacizumab, brivanib alaninat, cilengtide, combretastatin, DAST, endostatin, fenretinide, halofuginone, pazopanib, ranibizumab, rebimastat, removab, revlimid, sorafenib, vatalanib, squalamine, sunitinib, telatinib, thalidomide, ukrain, and vitaxin;

Antibodies include, but are not limited to, trastuzumab, cetuximab, bevacizumab, rituximab, ticilimumab, ipilimumab, lumiliximab, catumaxomab, atacicept, oregovomab, and alemtuzumab;

VEGF inhibitors such as, e.g., sorafenib, DAST, bevacizumab, sunitinib, recentin, axitinib, aflibercept, telatinib, brivanib alaninate, vatalanib, pazopanib, and ranibizumab; Palladia EGFR (HER1) inhibitors such as, e.g., cetuximab, panitumumab, vectibix, gefitinib, erlotinib, and Zactima;

HER2 inhibitors such as, e.g., lapatinib, tratuzumab, and pertuzumab;

mTOR inhibitors such as, e.g., temsirolimus, sirolimus/Rapamycin, and everolimus;

c-Met inhibitors;

PI3K and AKT inhibitors;

CDK inhibitors such as roscovitine and flavopiridol;

Spindle assembly checkpoints inhibitors and targeted antimitotic agents such as PLK inhibitors, Aurora inhibitors (e.g. Hesperadin), checkpoint kinase inhibitors, and KSP inhibitors;

HDAC inhibitors such as, e.g., panobinostat, vorinostat, MS275, belinostat, and LBH589;

HSP90 and HSP70 inhibitors;

Proteasome inhibitors such as bortezomib and carfilzomib;

Serine/threonine kinase inhibitors including MEK inhibitors (such as e.g. RDEA 119) and Raf inhibitors such as sorafenib;

Farnesyl transferase inhibitors such as, e.g., tipifarnib;

Tyrosine kinase inhibitors including, e.g., dasatinib, nilotibib, DAST, bosutinib, sorafenib, bevacizumab, sunitinib, AZD2171, axitinib, aflibercept, telatinib, imatinib mesylate, brivanib alaninate, pazopanib, ranibizumab, vatalanib, cetuximab, panitumumab, vectibix, gefitinib, erlotinib, lapatinib, tratuzumab, pertuzumab, and c-Kit inhibitors; Palladia, masitinib Vitamin D receptor agonists;

Bcl-2 protein inhibitors such as obatoclax, oblimersen sodium, and gossypol;

Cluster of differentiation 20 receptor antagonists such as, e.g., rituximab;

Ribonucleotide reductase inhibitors such as, e.g., gemcitabine;

Tumor necrosis apoptosis inducing ligand receptor 1 agonists such as, e.g., mapatumumab;

5-Hydroxytryptamine receptor antagonists such as, e.g., rEV598, xaliprode, palonosetron hydrochloride, granisetron, Zindol, and AB-1001;

Integrin inhibitors including alpha5-beta1 integrin inhibitors such as, e.g., E7820, JSM 6425, voloximab, and endostatin;

Androgen receptor antagonists including, e.g., nandrolone decanoate, fluoxymesterone, Android, Prost-aid, andromustine, bicalutamide, flutamide, apo-cyproterone, apo-flutamide, chlormadinone acetate, Androcur, Tabi, cyproterone acetate, and nilutamide;

Aromatase inhibitors such as, e.g., anastrozole, letrozole, testolactone, exemestane, aminoglutethimide, and formestane;

Matrix metalloproteinase inhibitors;

Other anti-cancer agents including, e.g., alitretinoin, ampligen, atrasentan bexarotene, bortezomib, bosentan, calcitriol, exisulind, fotemustine, ibandronic acid, miltefosine, mitoxantrone, I-asparaginase, procarbazine, dacarbazine, hydroxycarbamide, pegaspargase, pentostatin, tazaroten, velcade, gallium nitrate, canfosfamide, darinaparsin, and tretinoin.

The compounds of the present invention may also be employed in cancer treatment in conjunction with radiation therapy and/or surgical intervention.

Further aspects of the present invention relate to the use of the compounds of general formula (I) for the preparation of a pharmaceutical composition useful for prophylaxis and/or treatment of infectious diseases including opportunistic diseases, immunological diseases, autoimmune diseases, cardiovascular diseases, cell proliferative diseases, inflammation, erectile dysfunction and stroke.

Another preferred embodiment of the invention refers to a compound according to the general formula (I) for the preparation of a pharmaceutical composition for the prophylaxis and/or treatment of infectious diseases, including opportunistic diseases, immunological diseases, autoimmune diseases, cardiovascular diseases, cell proliferative diseases, inflammation, erectile dysfunction and stroke.

Infectious Diseases Including Opportunistic Infections

In yet another aspect of the present invention, the compounds according to the general formula (I) are for the preparation of a pharmaceutical composition for the prophylaxis and/or treatment of infectious diseases, including opportunistic diseases and opportunistic infections. The term infectious diseases comprises infections caused by viruses, bacteria, prions, fungi, and/or parasites.

Especially, virally induced infectious diseases, including opportunistic diseases are addressed. In a preferred embodiment of this aspect, the virally induced infectious diseases, including opportunistic diseases, are caused by retroviruses, human endogenous retroviruses (HERVs), hepadnaviruses, herpesviruses, flaviviridae, and/or adenoviruses. Preferably, the retroviruses are selected from lentiviruses or oncoretroviruses, wherein the lentivirus is preferably selected from the group comprising: HIV-1, HIV-2, feline immunodeficiency virus (FIV), bovine immunodeficiency virus (BIV), sivian immunodeficiency viruses (SIVs), chimeras of HIV and SIV (SHIV), caprine arthritis encephalitis virus (CAEV), visna/maedi virus (VMV) or equine infectious anemia virus (EIAV), preferably HIV-1 and HIV-2, and the oncoretrovirus is preferably selected from HTLV-I, HTLV-II or bovine leukemia virus (BLV), preferably HTLV-I and HTLV-II.

The hepadnavirus is preferably selected from HBV, ground squirrel hepatitis virus (GSHV) or woodchuck hepatitis virus (WHV), preferably HBV, the herpesvirus is selected from the group comprising: Herpes simplex virus I (HSV I), herpes simplex virus II (HSV II), Epstein-Barr virus (EBV), varicella zoster virus (VZV), human cytomegalovirus (HCMV) or human herpesvirus 8 (HHV-8), preferably HCMV, and the flaviviridae is selected from HCV, West nile or Yellow Fever.

It is to be understood, that all the viruses mentioned above, also comprise drug resistant virus strains.

Examples of infective diseases are AIDS, Alveolar Hydatid Disease (AHD, Echinococcosis), Amebiasis (*Entamoeba histolytica* Infection), *Angiostrongylus* Infection, Anisakiasis, Anthrax, Babesiosis (*Babesia* Infection), *Balantidium* Infection (Balantidiasis), *Baylisascaris* Infection (Raccoon Roundworm), *Bilharzia* (Schistosomiasis), *Blastocystis hominis* Infection (Blastomycosis), Boreliosis, Botulism, Brainerd Diarrhea, Brucellosis, BSE (Bovine Spongiform Encephalopathy), Candidiasis, Capillariasis (*Capillaria* Infection), CFS (Chronic Fatigue Syndrome), Chagas Disease (American Trypanosomiasis), Chickenpox (Varicella-Zoster virus), *Chlamydia pneumoniae* Infection, Cholera, Chronic Fatigue Syndrome, CJD (Creutzfeldt-Jakob Disease), Clonorchiasis (*Clonorchis* Infection), CLM (Cutaneous Larva Migrans, Hookworm Infection), Coccidioidomycosis, Conjunctivitis, Coxsackievirus A16 (Hand, Foot and Mouth Disease), Cryptococcosis, *Cryptosporidium* Infection (Cryptosporidiosis), *Culex* mosquito (Vector of West Nile Virus), Cutaneous Larva Migrans (CLM), Cyclosporiasis (*Cyclospora* Infection), Cysticercosis (Neurocysticercosis), Cytomegalovirus Infection, Dengue/Dengue Fever, *Dipylidium* Infection (Dog and Cat Flea Tapeworm), Ebola Virus Hemorrhagic Fever, Echinococcosis (Alveolar Hydatid Disease), Encephalitis, *Entomoeba coli* Infection, *Entomoeba dispar* Infection, *Entomoeba hartmanni* Infection, *Entomoeba histolytica* Infection (Amebiasis), *Entomoeba polecki* Infection, Enterobiasis (Pinworm Infection), Enterovirus Infection (Non-Polio), Epstein-Barr Virus Infection, *Escherichia coli* Infection, Foodborne Infection, Foot and mouth Disease, Fungal Dermatitis, Gastroenteritis, Group A streptococcal Disease, Group B streptococcal Disease, Hansen's Disease (Leprosy), Hantavirus Pulmonary Syndrome, Head Lice Infestation (Pediculosis), *Helicobacter pylori* Infection, Hematologic Disease, Hendra Virus Infection, Hepatitis (HCV, HBV), Herpes Zoster (Shingles), HIV Infection, Human Ehrlichiosis, Human Parainfluenza Virus Infection, Influenza, Isosporiasis (*Isospora* Infection), Lassa Fever, Leishmaniasis, Kala-azar (Kala-azar, *Leishmania* Infection), Leprosy, Lice (Body lice, Head lice, Pubic lice), Lyme Disease, Malaria, Marburg Hemorrhagic Fever, Measles, Meningitis, Mosquito-borne Diseases, *Mycobacterium avium* Complex (MAC) Infection, *Naegleria* Infection, Nosocomial Infections, Nonpathogenic Intestinal Amebae Infection, Onchocerciasis (River Blindness), Opisthorciasis (*Opisthorcis* Infection), Parvovirus Infection, Plague, PCP (*Pneumocystis carinii* Pneumonia), Polio, Q Fever, Rabies, Respiratory Syncytial Virus (RSV) Infection, Rheumatic Fever, Rift Valley Fever, River Blindness (Onchocerciasis), Rotavirus Infection, Roundworms Infection, Salmonellosis, *Salmonella Enteritidis*, Scabies, Shigellosis, Shingles, Sleeping Sickness, Smallpox, Streptococcal Infection, Tapeworm Infection (*Taenia* Infection), Tetanus, Toxic Shock Syndrome, Tuberculosis, Ulcers (Peptic Ulcer Disease), Valley Fever, *Vibrio parahaemolyticus* Infection, *Vibrio vulnificus* Infection, Viral Hemorrhagic Fever, Warts, Waterborne infectious Diseases, West Nile Virus Infection (West Nile Encephalitis), Whooping Cough, Yellow Fever.

Immunological Diseases

Another aspect of the present invention is directed to the use of at least one compound of the general formula (I) and/or pharmaceutically acceptable salts thereof for prophylaxis and/or treatment of immunological diseases, neuroimmunological diseases, and autoimmune diseases.

Immunological diseases are, for instance, asthma and diabetes, rheumatic and autoimmune diseases, AIDS, rejection of transplanted organs and tissues (cf. below), rhinitis, chronic obstructive pulmonary diseases, osteoporisis, ulcerative colitis, sinusitis, lupus erythematosus, recurrent infections, atopic dermatitis/eczema and occupational allergies, food allergies, drug allergies, severe anaphylactic reactions, anaphylaxis, and other manifestations of allergic disease, as well as uncommon problems such as primary immunodeficiencies, including antibody deficiency states, cell mediated immunodeficiencies (e.g., severe combined immunodeficiency, DiGeorge syndrome, Hyper-IgE syndrome, Wiskott-Aldrich syndrome, ataxia-telangiectasia), immune mediated cancers, and white cell defects.

In autoimmune diseases, such as systemic lupus erythematosus, rheumatoid arthritis (RA), multiple sclerosis (MS), immune-mediated or type 1 diabetes mellitus, immune mediated glomerulonephritis, scleroderma, pernicious anemia, alopecia, pemphigus, pemphigus vulgaris, myasthenia gravis, inflammatory bowel diseases, Crohn's disease, psoriasis, autoimmune thyroid diseases, and Hashimoto's disease, dermatomyositis, goodpastture syndrome, myasthenia gravis pseudoparalytica, ophtalmia sympatica, phakogene uveitis, chronical agressivce hepatitis, primary billiary cirrhosis, autoimunehemolytic anemy, Werlof disease, specific cells uncontrollably attack the body's own tissues and organs (autoimmunity), producing inflammatory reactions and other serious symptoms and diseases.

Hashimoto's thyroiditis is one of the most common autoimmune diseases. "Autoimmune disease" refers to a category of more than 80 chronic illnesses, each very different in nature, that can affect everything from the endocrine glands (like the thyroid) to organs like the kidneys, as well as to the digestive system.

There are many different autoimmune diseases, and they can each affect the body in different ways. For example, the autoimmune reaction is directed against the brain in multiple sclerosis and the gut in Crohn's disease. In other autoimmune diseases such as systemic lupus erythematosus (lupus), affected tissues and organs may vary among individuals with the same disease. One person with lupus may have affected skin and joints whereas another may have affected skin, kidney, and lungs. Ultimately, damage to certain tissues by the immune system may be permanent, as with destruction of insulin-producing cells of the pancreas in Type 1 diabetes mellitus.

Cardiovascular Diseases

The inventive compounds are also useful for prophylaxis and/or treatment of cardiovascular diseases such as cardiac hypertrophy, adult congenital heart disease, aneurysm, stable angina, unstable angina, angina pectoris, angioneurotic edema, aortic valve stenosis, aortic aneurysm, arrhythmia, arrhythmogenic right ventricular dysplasia, arteriosclerosis, arteriovenous malformations, atrial fibrillation, Behcet syndrome, bradycardia, cardiac tamponade, cardiomegaly, congestive cardiomyopathy, hypertrophic cardiomyopathy, restrictive cardiomyopathy, cardiovascular disease prevention, carotid stenosis, cerebral hemorrhage, Churg-Strauss syndrome, diabetes, Ebstein's Anomaly, Eisenmenger complex, cholesterol embolism, bacterial endocarditis, fibromuscular dysplasia, congenital heart defects, heart diseases, congestive heart failure, heart valve diseases, heart attack, epidural hematoma, hematoma, subdural, Hippel-Lindau disease, hyperemia, hypertension, pulmonary hypertension, hypertrophic growth, left ventricular hypertrophy, right ventricular hypertrophy, hypoplastic left heart syndrome, hypotension, intermittent claudication, ischemic heart disease, Klippel-Trenaunay-Weber syndrome, lateral medullary syndrome, long QT syndrome mitral valve prolapse, moyamoya disease, mucocutaneous lymph node syndrome, myocardial infarction, myocardial ischemia, myocarditis, pericarditis, peripheral vascular diseases, phlebitis, polyarteritis nodosa, pulmonary atresia, Raynaud disease, restenosis, Sneddon syndrome, stenosis, superior vena cava syndrome, syndrome X, tachycardia, Takayasu's arteritis, hereditary hemorrhagic telangiectasia, telangiectasis, temporal arteritis, tetralogy of fallot, thromboangiitis obliterans, thrombosis, thromboembolism, tricuspid atresia, varicose veins, vascular diseases, vasculitis, vasospasm, ventricular fibrillation, Williams syndrome, peripheral vascular disease, varicose veins and leg ulcers, deep vein thrombosis, Wolff-Parkinson-White syndrome.

Preferred are cardiac hypertrophy, adult congenital heart disease, aneurysms, angina, angina pectoris, arrhythmias, cardiovascular disease prevention, cardiomyopathies, congestive heart failure, myocardial infarction, pulmonary hypertension, hypertrophic growth, restenosis, stenosis, thrombosis and arteriosclerosis.

Proliferative Disease

In yet another preferred embodiment, the cell proliferative disease is cancer, which is preferably selected from the group comprising or consisting of:

The proliferation disorders and cancers are preferably selected from the group comprising or consisting of adenocarcinoma, choroidal melanoma, acute leukemia, acoustic neurinoma, ampullary carcinoma, anal carcinoma, astrocytoma, basal cell carcinoma, pancreatic cancer, desmoid tumor, bladder cancer, bronchial carcinoma, breast cancer, Burkitt's lymphoma, corpus cancer, CUP-syndrome (carcinoma of unknown primary), colorectal cancer, small intestine cancer, small intestinal tumors, ovarian cancer, endometrial carcinoma, ependymoma, epithelial cancer types, Ewing's tumors, gastrointestinal tumors, gastric cancer, gallbladder cancer, gall bladder carcinomas, uterine cancer, cervical cancer, cervix, glioblastomas, gynecologic tumors, ear, nose and throat tumors, hematologic neoplasias, hairy cell leukemia, urethral cancer, skin cancer, skin testis cancer, brain tumors (gliomas), brain metastases, testicle cancer, hypophysis tumor, carcinoids, Kaposi's sarcoma, laryngeal cancer, germ cell tumor, bone cancer, colorectal carcinoma, head and neck tumors (tumors of the ear, nose and throat area), colon carcinoma, craniopharyngiomas, oral cancer (cancer in the mouth area and on lips), cancer of the central nervous system, liver cancer, liver metastases, leukemia, eyelid tumor, lung cancer, lymph node cancer (Hodgkin's/Non-Hodgkin's lymphomas), lymphomas, stomach cancer, malignant melanoma, malignant neoplasia, malignant tumors gastrointestinal tract, breast carcinoma, rectal cancer, medulloblastomas, melanoma, meningiomas, Hodgkin's disease, mycosis fungoides, nasal cancer, neurinoma, neuroblastoma, kidney cancer, renal cell carcinomas, non-Hodgkin's lymphomas, oligodendroglioma, esophageal carcinoma, osteolytic carcinomas and osteoplastic carcinomas, osteosarcomas, ovarial carcinoma, pancreatic carcinoma, penile cancer, plasmocytoma, prostate cancer, pharyngeal cancer, rectal carcinoma, retinoblastoma, vaginal cancer, thyroid carcinoma, Schneeberger disease, esophageal cancer, spinaliomas, T-cell lymphoma (mycosis fungoides), thymoma, tube carcinoma, eye tumors, urethral cancer, urologic tumors, urothelial carcinoma, vulva cancer, wart appearance, soft tissue tumors, soft tissue sarcoma, Wilm's tumor, cervical carcinoma, tongue cancer, invasive ductal carcinoma, invasive lobular carcinoma, ductal carcinoma in situ, lobular carcinoma in situ, small-cell lung carcinoma, non-small-cell lung carcinoma, bronchial adenoma, pleuropulmonary blastoma, mesothelioma, brain stem glioma, hypophtalmic glioma, cerebellar astrocytoma, cerebral astrocytoma, neuroectodermal tumours, pineal tumors, sarcoma of the uterus, salivary gland cancers, anal gland adenocarcinomas, mast cell tumors, pelvis tumours, ureter tumours, hereditary papillary renal cancers, sporadic papillary renal cancers, intraocular melanoma, hepatocellular carcinoma (liver cell carcinomas with or without fibrolamellar variant), cholangiocarcinoma (intrahepatic bile duct carcinoma), mixed hepatocellular cholangiocarcinoma, squamous cell carcinoma, malignant melanoma, Merkel cell skin cancer, non-melanoma skin cancer, hypopharyngeal cancer, nasopharyngeal cancer, oropharyngeal cancer, oral cavity cancer, squamous cell cancer, oral melanoma, AIDS-related lymphoma, cutaneous T-cell lymphoma, lymphoma of the central nervous system, malignant fibrous histiocytoma, lymphosarcoma, rhabdomyosarcoma, malignant histiocytosis, fibrosarcoma, hemangiosarcoma, hemangiopericytoma, leiomyosarcoma, canine mammary carcinoma, and feline mammary carcinoma.

Preferred are the following cancer types: Leukemias including but not limited to chronic lymphocytic leukemia, chronic myelogenous leukemia, acute lymphoblastic leukemia, acute myeloid leukemia, mixed lineage leukemia, bladder cancer, breast cancer, breast carcinoma, cancer of the central nervous system, colon carcinoma, gastric cancer, lung cancer, kidney cancer, melanoma, head and neck tumors (tumors of the ear, nose and throat area), ovarian cancer, ovarial carcinoma, cervical cancer, cervix, cervical carcinoma, glioblastomas, pancreatic cancer, pancreatic carcinoma, prostate cancer, stomach cancer, skin cancer, skin testis cancer, Hodgkin's lymphoma, liver cancer, liver metastases and renal cell carcinomas.

Inflammation

In yet another preferred embodiment, said inflammation is mediated preferably by the cytokines TNF-α, IL-1β, GM-CSF, IL-6 and/or IL-8.

As described above, the compounds according to general formula (I) are pharmaceutically active agents for prophylaxis and/or treatment of inflammatory diseases. Thus, these compounds are used for the manufacture of a pharmaceutical formulation for prophylaxis and/or treatment of inflammations and inflammatory diseases in mammals, including humans.

Inflammatory diseases can emanate from infectious and non-infectious inflammatory conditions which may result from infection by an invading organism or from irritative, traumatic, metabolic, allergic, autoimmune, or idiopathic causes as shown in the following list.

I. Acute infections

| A. Viral | B. Bacterial |
|---|---|

II. Noninfectious causes
III. Chronic (granulomatous) diseases

| A. Bacterial | B. Spirochetal |
|---|---|
| C. Mycotic (Fungal) | D. Idiopathic |

IV. Allergic, immune, and idiopathic disorders
   A. Hypersensitivity reactions
   B. Immune and idiopathic disorders
V. Miscellaneous inflammatory conditions
   A. Parasitic infections
   B. Inhalation causes: —Acute (thermal) injury
      —Pollution and inhalant allergy
      —Carcinogens
   C. Radiation injury: —Radionecrosis Thus, the compounds disclosed herein can be used for prophylaxis and/or treatment of inflammations caused by invading organisms such as viruses, bacteria, prions, and parasites as well as for prophylaxis and/or treatment of inflammations caused by irritative, traumatic, metabolic, allergic, autoimmune, or idiopathic reasons.

Consequently, the disclosed compounds are useful for prophylaxis and/or treatment of inflammatory diseases which are initiated or caused by viruses, parasites, and bacteria which are connected to or involved in inflammations.

The following bacteria are known to cause inflammatory diseases: mycoplasma pulmonis (causes e.g. chronic lung diseases (CLD), murine chronic respiratory disease), *ureaplasma urealyticum* (causes pneumonia in newborns), *mycoplasma pneumoniae* and *chlamydia pneumoniae* (cause chronic asthma), *C. pneumoniae* (causes atherosclerosis, pharyngitis to pneumonia with empyema, human coronary heart disease), *Helicobacter pylori* (human coronary heart disease, stomach ulcers). The following viruses are known to cause inflammatory diseases: herpesviruses especially cytomegalovirus (causes human coronary heart disease).

The compounds disclosed herein are useful for prophylaxis and/or treatment of inflammatory diseases caused and/or induced and/or initiated and/or enhanced by the afore-mentioned bacteria or viruses.

Furthermore, the compounds of formula (I) are useful for prophylaxis and/or treatment of inflammatory diseases of the central nervous system (CNS), inflammatory rheumatic diseases, inflammatory diseases of blood vessels, inflammatory diseases of the middle ear, inflammatory bowel diseases, inflammatory diseases of the skin, inflammatory disease uveitis, inflammatory diseases of the larynx.

Examples for inflammatory diseases of the central nervous system (CNS) are algal disorders, protothecosis, bacterial disorders, abscessation, bacterial meningitis, idiopathic inflammatory disorders, eosinophilic meningoencephalitis, feline polioencephalomyelitis, granulomatous meningoencephalomyelitis, meningitis, steroid responsive meningitis-arteritis, miscellaneous meningitis/meningoencephalitis, meningoencephalitis in greyhounds, necrotizing encephalitis, pyogranulomatous meningoencephalomyelitis, shaker dog disease, mycotic diseases of the CNS, parasitic encephalomyelitis, prion protein induced diseases, feline spongiform encephalopathy, protozoal encephalitis-encephalomyelitis, toxoplasmosis, neosporosis, sarcocystosis, encephalitozoonosis, trypanosomiasis, acanthamebiasis, babesiosis, leishmaniasis, rickettsial disorders, rocky mountain spotted fever, canine ehrlichiosis, salmon poisoning, viral disorders, aujeszky's disease, borna disease, canine herpes virus encephalomyelitis, canine distemper encephalomyelitis, canine distemper encephalomyelitis in immature animals, chronic relapsing encephalomyelitis, post-vaccinal canine distemper encephalitis, feline immunodeficiency virus, feline infectious peritonitis, feline leukemia virus, infectious canine hepatitis, La Crosse virus encephalitis, parvovirus encephalitis, rabies, post-vaccinal rabies.

Examples for inflammatory rheumatic diseases are rheumatoid arthritis, scleroderma, lupus, polymyositis, dermatomyositis, psoriatic arthritis, ankylosing spondylitis, Reiters's syndrome, juvenile rheumatoid arthritis, bursitis, tendinitis (tendonitis), and fibromyositis.

Examples for inflammatory diseases of blood vessels are vasculitis, autoantibodies in vasculitis, microscopic polyangiitis, giant cell arteritis, Takayasu's arteritis, vasculitis of the central nervous system, thromboangiitis obliterans (Buerger's Disease), vasculitis secondary to bacterial, fungal, and parasitic infection, vasculitis and rheumatoid arthritis, vasculitis in systemic lupus erythematosus, vasculitis in the idiopathic inflammatory myopathies, relapsing polychondritis, systemic vasculitis in sarcoidosis, vasculitis and malignancy, and drug-induced vasculitis.

Examples for inflammatory diseases of the middle ear are acute suppurative otitis media, bullous myringitis, granular myringitis, and chronic suppurative otitis media, which can manifest as mucosal disease, cholesteatoma, or both.

Examples for inflammatory bowel diseases are ulcerative colitis, Crohn's disease.

Examples for inflammatory diseases of the skin are acute inflammatory dermatoses, urticaria (hives), spongiotic dermatitis, allergic contact dermatitis, irritant contact dermatitis, atopic dermatitis, erythemal multiforme (EM minor), Stevens-Johnson syndrome (SJS, EM major), toxic epidermal necrolysis (TEN), chronic inflammatory dermatoses, psoriasis, lichen planus, discoid lupus erythematosus, and acne vulgaris.

Uveitis are inflammations located in and/or on the eye and may be associated with inflammation elsewhere in the body. In most circumstances, patients who have uveitis as part of a disease elsewhere in the body are aware of that illness. The majority of patients with uveitis do not have an apparent associated systemic illness. Causes of uveitis can be infectious causes, masquerade syndromes, suspected immune-mediated diseases, and/or syndromes confined primarily to the eye.

The following viruses are associated with inflammations: human immunodeficiency virus-I, herpes simplex virus, herpes zoster virus, and cytomegalovirus.

Bacterial or spirochetal caused, induced, initiated and/or enhanced inflammations are tuberculosis, leprosy, proprionobacterium, syphilis, Whipple's disease, leptospirosis, brucellosis, and lyme disease.

Parasitic (protozoan or helminthic) caused, induced, initiated and/or enhanced inflammations are toxoplasmosis, acanthameba, toxocariasis, cysticercosis, onchocerciasis.

Examples of inflammatory diseases caused, induced, initiated and/or enhanced by fungi are histoplasmosis, coccidioidomycosis, candidiasis, aspergillosis, sporotrichosis, blastomycosis, and cryptococcosis.

Masquerade syndromes are, for instance, leukemia, lymphoma, retinitis pigmentosa, and retinoblastoma.

Suspected immune-mediated diseases can be selected from the group comprising ankylosing spondylitis, Behcet's disease, Crohn's disease, drug or hypersensitivity reaction, interstitial nephritis, juvenile rheumatoid arthritis, Kawasaki's disease, multiple sclerosis, psoriatic arthritis, Reiter's syndrome, relapsing polychondritis, sarcoidosis, Sjogren's syndrome, systemic lupus erythematosus, ulcerative colitis, vasculitis, vitiligo, Vogt Koyanagi Harada syndrome.

Syndromes confined primarily to the eye are, for instance, acute multifocal placoid pigmentary epitheliopathy, acute retinal necrosis, birdshot choroidopathy, Fuch's heterochromic cyclitis, glaucomatocyclitic crisis, lens-induced uveitis, multifocal choroiditis, pars planitis, serpiginous choroiditis, sympathetic ophthalmia, and trauma.

Examples for inflammatory diseases of the larynx are gastroesophageal (laryngopharyngeal) reflux disease, pediatric laryngitis, acute laryngeal infections of adults, chronic (granulomatous) diseases, allergic, immune, and idiopathic disorders and miscellaneous inflammatory conditions.

Pediatric laryngitis is known as acute (viral or bacterial) infection such as laryngotracheitis (croup), supraglottitis (epiglottitis), diphtheria, and noninfectious causes are for example spasmodic croup and traumatic laryngitis.

Acute laryngeal infections of adults are, for instance, viral laryngitis, common upper respiratory infection, laryngotracheitis, herpes simplex, bacterial laryngitis, supraglottitis, laryngeal abscess, and gonorrhea.

Chronic (granulomatous) diseases can be selected from the group comprising bacterial diseases, tuberculosis, leprosy, scleroma, actinomycosis, tularemia, glanders, spirochetal (syphilis) diseases, mycotic (fungal) diseases, candidiasis, blastomycosis, histoplasmosis, coccidiomycosis, aspergillosis, idiopathic diseases, sarcoidosis, and Wegener's granulomatosis.

Allergic, immune, and idiopathic disorders are, for example, hypersensitivity reactions, angioedema, Stevens-Johnson syndrome, immune and idiopathic disorders, infections of the immunocompromised host, rheuatoid arthritis, systeic lupus erythematosus, cicatricial pemphigoid, relapsing polychondritis, Sjogren's syndrome, and amyloidosis.

Miscellaneous inflammatory conditions are, for instance, parasitic infections, trichinosis, leishmaniasis, schistosomiasis, syngamus laryngeus, inhalation laryngitis, acute (thermal) injury, pollution and inhalant allergy, carcinogens, radiation injury, radiation laryngitis, radionecrosis, vocal abuse, vocal-cord hemorrhage, muscle tension dysphonias, and contact ulcer and granuloma.

Stroke

The inventive compounds according to the general formula (I) as well as pharmaceutically acceptable salts thereof are also useful for treatment of stroke.

In another aspect of the present invention, the compounds according to the general formula (I) as well as pharmaceutically acceptable salts thereof are used as an inhibitor for a protein kinase, preferably as an inhibitor for a cellular protein kinase.

In a preferred embodiment of this aspect said cellular protein kinase consists of Cyclin-dependent protein kinases (CDKs).

The cyclin-dependent protein kinase can be selected from the group comprising: CDK1, CDK2, CDK3, CDK4, CDK5, CDK6, CDK7, CDK8, CDK9, CDK10, CDK11, CrkRS (Crk7, CDC2-related protein kinase 7), CDKL1 (cyclin-dependent kinase-like 1); KKIALRE, CDKL2 (cyclin-dependent kinase-like 2), KKIAMRE, CDKL3 (cyclin-dependent kinase-like 3), NKIAMRE, CDKL4, similar to cyclin-dependent kinase-like 1, CDC2L1 (cell division cycle 2-like 1), PITSLRE B, CDC2L1 (cell division cycle 2-like 1), PITSLRE A, CDC2L5 (cell division cycle 2-like 5), PCTK1 (PCTAIRE protein kinase 1), PCTK2 (PCTAIRE protein kinase 2), PCTK3 (PCTAIRE protein kinase 3) or PFTK1 (PFTAIRE protein kinase 1).

In a further preferred embodiment said cyclin-dependent protein kinase is CDK9. Thus, the compounds according to the general formula (I) as well as pharmaceutically acceptable salts thereof are used as an inhibitor for CDK9.

Surprisingly it turned out that the compounds according to the general formula (I) as well as pharmaceutically acceptable salts thereof selectively inhibit CDK9 in comparison to other protein kinases and in comparison to other cyclin-dependent protein kinases. Thus, the compounds according to the general formula (I) as well as pharmaceutically acceptable salts thereof are used as selective inhibitors for CDK9.

As used herein, a kinase "inhibitor" refers to any compound capable of downregulating, decreasing, suppressing or otherwise regulating the amount and/or activity of a kinase. Inhibition of these kinases can be achieved by any of a variety of mechanisms known in the art, including, but not limited to binding directly to the kinase polypeptide, denaturing or otherwise inactivating the kinase, or inhibiting the expression of the gene (e.g., transcription to mRNA, translation to a nascent polypeptide, and/or final polypeptide modifications to a mature protein), which encodes the kinase. Generally, kinase inhibitors may be proteins, polypeptides, nucleic acids, small molecules, or other chemical moieties.

As used herein the term "inhibiting" or "inhibition" refers to the ability of a compound to downregulate, decrease, reduce, suppress, inactivate, or inhibit at least partially the activity of an enzyme, or the expression of an enzyme or protein and/or the virus replication.

In a further aspect of the present invention, a method for preventing and/or treating infectious diseases, including opportunistic diseases, in a mammal, especially in a human, is provided, which method comprises administering to the mammal an amount of at least one compound according to the general formula (I), effective to prevent and/or treat said infectious diseases, including opportunistic diseases. In a preferred embodiment of this method, the infectious diseases, including opportunistic diseases, are virally induced infectious diseases. The virally induced infectious diseases, including opportunistic diseases, are caused by retroviruses, hepadnaviruses, herpesviruses, flaviviridae, and/or adenoviruses. In a further preferred embodiment of this method, the retroviruses are selected from lentiviruses or oncoretroviruses, wherein the lentivirus is selected from the group comprising: HIV-1, HIV-2, FIV, BIV, SIVs, SHIV, CAEV, VMV or EIAV, preferably HIV-1 or HIV-2 and wherein the oncoretrovirus is selected from the group consisting of: HTLV-I, HTLV-II or BLV. In a further preferred embodiment of this method, the hepadnavirus is selected from HBV, GSHV or WHV, preferably HBV, the herpesivirus is selected from the group comprising: HSV I, HSV II, EBV, VZV, HCMV or HHV 8, preferably HCMV and the flaviviridae is selected from HCV, West nile or Yellow Fever.

In a further aspect of the present invention, methods for preventing and/or treating infectious diseases including opportunistic diseases, prion diseases, immunological diseases, autoimmune diseases, cardiovascular diseases, cell proliferative diseases, inflammation, erectile dysfunction and stroke in a mammal, especially in a human, are provided, which methods comprise administering to the mammal an amount of at least one compound according to the general formula (I) and/or pharmaceutically acceptable salts thereof, effective to prevent and/or treat said infectious diseases including opportunistic diseases, prion diseases, immunological diseases, autoimmune diseases, cardiovascular diseases, cell proliferative diseases, inflammation, erectile dysfunction and stroke.

In further preferred embodiments, the specific diseases addressed as infectious diseases including opportunistic diseases, prion diseases, immunological diseases, autoimmune diseases, cardiovascular diseases, cell proliferative diseases, inflammation, erectile dysfunction and stroke are selected from the groups disclosed above.

The compounds shown explicitly in Table 1 are preferred to be used within the methods or indications disclosed herein. Another aspect of the present invention is that at least one compound according to the general formula (I) used as a pharmaceutically active agent may be administered in combination with further therapeutic compounds.

For the indication HIV compounds according to the general formula (I), preferably those falling under the activity range "a" for CDK9 as shown in Table 5, may be administered in combination with anti-retroviral drugs, selected from the following five classes:

1) Nucleoside reverse transcriptase inhibitors (NRTIs),
2) Non-nucleoside reverse transcriptase inhibitors (NNRTIs),
3) Protease inhibitors (PIs),
4) Fusion inhibitors or
5) Immune stimuli.

Thus, another aspect of the present invention relates to drug combinations comprising at least one inventive compound according to general formula (I) and/or pharmaceutically acceptable salts thereof together with at least one anti-retroviral drug, especially at least one of the drugs mentioned above.

The pharmaceutical compositions according to the present invention comprise at least one compound according to the present invention as an active ingredient together with at least one pharmaceutically acceptable (i.e. non-toxic) carrier, excipient and/or diluent. The pharmaceutical compositions of the present invention can be prepared in a conventional solid or liquid carrier or diluent and a conventional pharmaceutically-made adjuvant at suitable dosage level in a known way. The preferred preparations are adapted for oral application. These administration forms include, for example, pills, tablets, film tablets, coated tablets, capsules, powders and deposits.

Furthermore, the present invention also includes pharmaceutical preparations for parenteral application, including dermal, intradermal, intragastral, intracutan, intravasal, intravenous, intramuscular, intraperitoneal, intranasal, intravaginal, intrabuccal, percutan, rectal, subcutaneous, sublingual, topical, or transdermal application, which preparations in addition to typical vehicles and/or diluents contain at least one compound according to the present invention and/or a pharmaceutical acceptable salt thereof as active ingredient.

The pharmaceutical compositions according to the present invention containing at least one compound according to the present invention and/or a pharmaceutical acceptable salt thereof as active ingredient will typically be administered together with suitable carrier materials selected with respect to the intended form of administration, i.e. for oral administration in the form of tablets, capsules (either solid filled, semi-solid filled or liquid filled), powders for constitution, gels, elixirs, dispersable granules, syrups, suspensions, and the like, and consistent with conventional pharmaceutical practices. For example, for oral administration in the form of tablets or capsules, the active drug component may be combined with any oral non-toxic pharmaceutically acceptable carrier, preferably with an inert carrier like lactose, starch, sucrose, cellulose, magnesium stearate, dicalcium phosphate, calcium sulfate, talc, mannitol, ethyl alcohol (liquid filled capsules) and the like. Moreover, suitable binders, lubricants, disintegrating agents and coloring agents may also be incorporated into the tablet or capsule.

Powders and tablets may contain about 5 to about 95-weight % of the 4,6-disubstituted pyrimdine derivative according to the general formula (I) or analogues compound thereof or the respective pharmaceutically active salt as active ingredient.

Suitable binders include starch, gelatin, natural sugars, corn sweeteners, natural and synthetic gums such as acacia, sodium alginate, carboxymethylcellulose, polyethylene glycol and waxes. Among suitable lubricants there may be mentioned boric acid, sodium benzoate, sodium acetate, sodium chloride, and the like. Suitable disintegrants include starch, methylcellulose, guar gum, and the like. Sweetening and flavoring agents as well as preservatives may also be included, where appropriate. The disintegrants, diluents, lubricants, binders etc. are discussed in more detail below.

Moreover, the pharmaceutical compositions of the present invention may be formulated in sustained release form to provide the rate controlled release of any one or more of the components or active ingredients to optimise the therapeutic effect(s), e.g. antihistaminic activity and the like. Suitable dosage forms for sustained release include tablets having layers of varying disintegration rates or controlled release polymeric matrices impregnated with the active components and shaped in tablet form or capsules containing such impregnated or encapsulated porous polymeric matrices.

Liquid form preparations include solutions, suspensions, and emulsions. As an example, there may be mentioned water or water/propylene glycol solutions for parenteral injections or addition of sweeteners and opacifiers for oral solutions, suspensions, and emulsions. Liquid form preparations may also include solutions for intranasal administration.

Aerosol preparations suitable for inhalation may include solutions and solids in powder form, which may be present in combination with a pharmaceutically acceptable carrier such as an inert, compressed gas, e.g. nitrogen.

For preparing suppositories, a low melting wax, such as a mixture of fatty acid glycerides like cocoa butter is melted first, and the active ingredient is then dispersed homogeneously therein e.g. by stirring. The molten, homogeneous mixture is then poured into conveniently sized moulds, allowed to cool, and thereby solidified.

Also included are solid form preparations, which are intended to be converted, shortly before use, to liquid form preparations for either oral or parenteral administration. Such liquid forms include solutions, suspensions, and emulsions.

The compounds according to the present invention may also be delivered transdermally. The transdermal compositions may have the form of a cream, a lotion, an aerosol and/or an emulsion and may be included in a transdermal patch of the matrix or reservoir type as is known in the art for this purpose.

The term capsule as recited herein refers to a specific container or enclosure made e.g. of methylcellulose, polyvinyl alcohols, or denatured gelatins or starch for holding or containing compositions comprising the active ingredient(s). Capsules with hard shells are typically made of blended of relatively high gel strength gelatins from bones or pork skin. The capsule itself may contain small amounts of dyes, opaquing agents, plasticisers and/or preservatives.

Under tablet a compressed or moulded solid dosage form is understood which comprises the active ingredients with suitable diluents. The tablet may be prepared by compression of mixtures or granulations obtained by wet granulation, dry granulation, or by compaction well known to a person of ordinary skill in the art.

Oral gels refer to the active ingredients dispersed or solubilised in a hydrophilic semi-solid matrix.

Powders for constitution refers to powder blends containing the active ingredients and suitable diluents which can be suspended e.g. in water or in juice.

Suitable diluents are substances that usually make up the major portion of the composition or dosage form. Suitable diluents include sugars such as lactose, sucrose, mannitol, and sorbitol, starches derived from wheat, corn rice, and potato, and celluloses such as microcrystalline cellulose. The amount of diluent in the composition can range from about 5 to about 95% by weight of the total composition, preferably from about 25 to about 75 weight %, and more preferably from about 30 to about 60 weight %.

The term disintegrants refers to materials added to the composition to support break apart (disintegrate) and release the pharmaceutically active ingredients of a medicament. Suitable disintegrants include starches, "cold water soluble" modified starches such as sodium carboxymethyl starch, natural and synthetic gums such as locust bean, karaya, guar, tragacanth and agar, cellulose derivatives such as methylcellulose and sodium carboxymethylcellulose, microcrystalline celluloses, and cross-linked microcrystalline celluloses such as sodium croscaramellose, alginates such as alginic acid and sodium alginate, clays such as bentonites, and effervescent mixtures. The amount of disintegrant in the composition may range from about 2 to about 20 weight % of the composition, more preferably from about 5 to about 10 weight %.

Binders are substances which bind or "glue" together powder particles and make them cohesive by forming granules, thus serving as the "adhesive" in the formulation. Binders add cohesive strength already available in the diluent or bulking agent. Suitable binders include sugars such as sucrose, starches derived from wheat corn rice and potato, natural gums such as acacia, gelatin and tragacanth, derivatives of seaweed such as alginic acid, sodium alginate and ammonium calcium alginate, cellulose materials such as methylcellulose, sodium carboxymethylcellulose and hydroxypropylmethylcellulose, polyvinylpyrrolidone, and inorganic compounds such as magnesium aluminum silicate. The amount of binder in the composition may range from about 2 to about 20 weight % of the composition, preferably from about 3 to about 10 weight %, and more preferably from about 3 to about 6 weight %.

Lubricants refer to a class of substances which are added to the dosage form to enable the tablet granules etc. after being compressed to release from the mould or die by reducing friction or wear. Suitable lubricants include metallic stearates such as magnesium stearate, calcium stearate, or potassium stearate, stearic acid, high melting point waxes, and other water soluble lubricants such as sodium chloride, sodium benzoate, sodium acetate, sodium oleate, polyethylene glycols and D,L-leucine. Lubricants are usually added at the very last step before compression, since they must be present at the surface of the granules. The amount of lubricant in the composition may range from about 0.2 to about 5 weight % of the composition, preferably from about 0.5 to about 2 weight %, and more preferably from about 0.3 to about 1.5 weight % of the composition.

Glidents are materials that prevent caking of the components of the pharmaceutical composition and improve the flow characteristics of granulate so that flow is smooth and uniform. Suitable glidents include silicon dioxide and talc. The amount of glident in the composition may range from about 0.1 to about 5 weight % of the final composition, preferably from about 0.5 to about 2 weight %.

Coloring agents are excipients that provide coloration to the composition or the dosage form. Such excipients can include food grade dyes adsorbed onto a suitable adsorbent such as clay or aluminum oxide. The amount of the coloring agent may vary from about 0.1 to about 5 weight % of the composition, preferably from about 0.1 to about 1 weight %.

EXAMPLES

Preparation of Compounds

Abbreviations Used in the Description of the Chemistry and in the Examples that Follow are ACN (acetonitrile); $CDCl_3$ (deuterated chloroform); cHex (cyclohexane); DCM (dichloromethane); DIPEA (di-isopropylethylamine); DME (1,2-dimethoxyethane); DMF (dimethylformamide); DMSO (dimethyl sulfoxide); eq (equivalent); ES (electrospray); EtOAc (ethyl acetate); EtOH (ethanol); MeOH (methanol); MS (mass spectrometry); NMR (nuclear magnetic resonance); Pd(dppf)Cl$_2$ ([1,1'-bis(diphenylphosphino)ferrocene]dichloro palladium(II) complex with dichloromethane); Pd(PPh$_3$)$_2$Cl$_2$ (dichlorobis(triphenylphosphine) palladium(II)); iPrOH (iso-propanol); RT (room temperature); sat. aq. (saturated aqueous); SiO$_2$ (silica gel); TFA (trifluoroacetic acid); THF (tetrahydrofuran).

Preparative Examples

Intermediates

Intermediate 1:
2-Chloro-4-(2-methoxyphenyl)pyridine (A1)

Method A:

To a solution of 4-bromo-2-chloro-pyridine (1.0 g, 5.2 mmol) in DME/water 10:1 (15 mL) was added (2-methoxyphenyl)boronic acid (0.79 g, 5.2 mmol), Pd(PPh$_3$)$_2$Cl$_2$ (240 mg, 0.34 mmol), and K$_2$CO$_3$ (1.8 g, 13.0 mmol). The mixture was heated with reflux for 6 hours. It was diluted with DCM, washed three times with water, dried over MgSO$_4$, and concentrated under reduced pressure. The residue was purified by flash chromatography (silica gel, DCM/MeOH 100:0 to 90:10) to give the title compound A1 (0.6 g, 52%). MS (ES) C$_{12}$H$_{10}$ClNO requires: 219. found: 220 (M+H)$^+$.

Method B:

To a solution of 4-bromo-2-chloro-pyridine (1.5 g, 7.8 mmol) in DME/water/EtOH 5:1:1 (20 mL) was added (2-methoxyphenyl)boronic acid (1.49 g, 9.8 mmol), Pd(PPh$_3$)$_2$Cl$_2$ (112 mg, 0.16 mmol), and Na$_2$CO$_3$ (1.65 g, 15.6 mmol). The mixture was heated at 125° C. for 90 minutes in a microwave oven. It was concentrated under reduced pressure, and the residue was purified by flash chromatography (silica gel, cHex/EtOAc 100:0 to 80:20) to give the title compound A1 (1.07 g, 62%). MS (ES) C$_{12}$H$_{10}$ClNO requires: 219. found: 220 (M+H)$^+$.

Intermediate 2:
2-Chloro-4-(4-fluoro-2-methoxyphenyl)pyridine (A2)

A mixture of 4-bromo-2-chloropyridine (1.92 g, 10 mmol), (4-fluoro-2-methoxyphenyl)boronic acid (1.70 g, 10 mmol) and K$_3$PO$_4$ (4.24 g, 20 mmol) in dioxane/water 10:1 (20 mL) was degassed with a stream of nitrogen for 10 min. After addition of Pd(dppf)Cl$_2$ (816 mg, 1 mmol) the reaction mixture was heated at 145° C. for 90 minutes in a microwave oven. It was diluted with EtOAc and washed twice with sat. aq. NaHCO$_3$ solution and once with brine. The organic layer was dried over MgSO$_4$ and concentrated under reduced pressure. The residue was purified by flash chromatography on silica gel (cHex/EtOAc 100:0 to 60:40) to yield the desired product A2 as a white solid (1.07 g, 45%). $^1$H NMR (400 MHz, d$_6$-DMSO, 300K) δ 3.81 (s, 3H), 6.87 (dt, J=8.5 Hz, J=3.5 Hz, 1H), 7.05 (dd, J=11.4 Hz, J=2.5 Hz, 1H), 7.44 (dd, J=8.5 Hz, J=6.8 Hz, 1H), 7.48 (dd, J=5.3 Hz, J=1.5 Hz, 1H), 7.55 (m, 1H), 8.38 (d, J=5.3 Hz, 1H). MS (ES) C$_{12}$H$_9$ClFNO requires: 237. found: 238 (M+H)$^+$.

Intermediate 3:
2-Fluoro-4-(2-methoxyphenyl)pyridine (A3)

To a solution of 2-fluoro-4-iodo-pyridine (0.5 g, 2.24 mmol) and (2-methoxyphenyl)boronic acid (0.34 g, 2.24 mmol) in DME/water 2:1 (15 mL) was added Pd(PPh$_3$)$_2$Cl$_2$ (20 mg, 0.028 mmol) and K$_2$CO$_3$ (20 mg, 0.15 mmol). The mixture was heated at 80° C. for 6 hours. It was diluted with DCM, washed with water, dried over MgSO$_4$, and concentrated under reduced pressure. The residue was purified by flash chromatography (silica gel, DCM/MeOH 100:0 to 90:10) to give the title compound A3 (0.25 g, 55%). MS (ES) C$_{12}$H$_{10}$FNO requires: 203. found: 204 (M+H)$^+$.

Intermediate 4:
4-((4-Iodopyridin-2-yl)amino)benzenesulfonamide (A4)

A mixture of 2-fluoro-4-iodopyridine (1.0 g, 4.48 mmol) and 4-aminobenzenesulfonamide (772 mg, 4.48 mmol) was heated with an oil bath for 3 hours at 150° C. The title compound A4 was obtained from the residue by preparative HPLC (water/ACN gradient). Yield: 135 mg (8%). MS (ES) C$_{11}$H$_{10}$IN$_3$O$_2$S requires: 375. found: 376 (M+H)$^+$.

Intermediate 5:
4-Iodo-N-(3-nitrophenyl)pyridine-2-amine (A5)

A mixture of 2-fluoro-4-iodopyridine (500 mg, 2.24 mmol), 3-nitroaniline (620 mg, 4.49 mmol), and Cs$_2$CO$_3$ (1460 mg, 4.48 mmol) in dry DMF (12.5 mL) was heated for 1 h at 130° C. in a microwave oven. The mixture was diluted with EtOAc and washed twice with brine. The organic layer was dried over MgSO$_4$ and concentrated under reduced pressure, and the residue was purified by flash chromatography on silica gel (DCM/MeOH 100:0 to 95:5) to yield the desired product A5 as a white solid (122 mg, 16%). $^1$H NMR (400 MHz, d$_6$-DMSO, 300K) δ 7.21 (d, J=5.4 Hz, 1H), 7.29 (s, 1H), 7.52 (t, J=8.1 Hz, 1H), 7.71 (d, J=8.1 Hz, 1H), 7.93 (m, 2H), 8.74 (t, J=2.1 Hz, 1H), 9.62 (s, 1H). MS (ES) C$_{11}$H$_8$IN$_3$O$_2$ requires: 341. found: 342 (M+H)$^+$.

Intermediate 6:
2-(3-Aminophenyl)ethanesulfonamide (A6)

The compound A6 has been obtained by reduction of 2-(3-nitrophenyl)-ethanesulfonamide according to the procedure described in WO2009/076140, and the nitro compound from 2-(3-nitrophenyl)ethanol according to J. Med. Chem. 45 (2002), 567-583.

Example Compounds

Example 1

4-(2-Methoxyphenyl)-N-phenylpyridin-2-amine (B1)

A mixture of A3 (80 mg, 0.39 mmol) and aniline (102 mg, 1.1 mmol) was heated for 20 minutes at 150° C. in a microwave oven. The title compound B1 was obtained from the residue by preparative HPLC (water/ACN gradient) as an amorphous solid (20 mg, 19%). MS (ES) C$_{18}$H$_{16}$N$_2$O requires: 276. found: 277 (M+H)$^+$.

Example 2

4-(2-Methoxyphenyl)-N-(3-nitrophenyl)pyridin-2-amine (C1)

A mixture of A1 (200 mg, 0.91 mmol) and 3-nitroaniline (126 mg, 0.91 mmol) was heated with an oil bath for 2 hours at 150° C. After addition of water and MeOH the precipitate of the title compound C1 was collected by filtration, washed with MeOH, and dried in vacuo. Yield: 10 mg (3.4%). MS (ES) $C_{18}H_{15}N_3O_3$ requires: 321. found: 322 (M+H)$^+$.

Example 3

4-(4-Fluoro-2-methoxyphenyl)-N-(3-nitrophenyl) pyridin-2-amine (C2)

The title compound C2 was prepared from A5 (122 mg, 0.36 mmol) and (4-fluoro-2-methoxyphenyl)boronic acid (112 mg, 0.66 mmol) following the procedure reported for the intermediate A2. The residue was purified by flash chromatography on silica gel (cHex/EtOAc 100:0 to 50:50) to yield the desired product C2 as an orange solid (98 mg, 80%). MS (ES) $C_{18}H_{14}FN_3O_3$ requires: 339. found: 340 (M+H)$^+$.

Example 4

3-[(4-(2-Methoxyphenyl)pyridin-2-yl)amino]benzenesulfonamide (D1)

A mixture of A1 (230 mg, 1.05 mmol) and 3-aminobenzenesulfonamide (180 mg, 1.05 mmol) was heated with an oil bath for 3 hours at 150° C. After addition of water and MeOH the precipitate of the title compound D1 was collected by filtration, washed with MeOH, and dried in vacuo. Yield: 147.6 mg (40%); colorless amorphous solid. $^1$H NMR (400 MHz, d$_6$-DMSO, 300K) δ 3.81 (s, 3H), 7.03-7.10 (m, 2H), 7.14-7.19 (m, 2H), 7.32-7.37 (m, 2H), 7.37-7.42 (m, 1H), 7.42-7.49 (m, 2H), 7.49-7.58 (m, 1H), 7.82 (bd, J=7.6 Hz, 1H), 8.06 (bs, 1H), 8.15 (d, J=5.8 Hz, 1H), 9.96 (bs, 1H). MS (ES) $C_{18}H_{17}N_3O_3S$ requires: 355. found: 356 (M+H)$^+$.

Example 5

N-(tert-Butyl)-3-[(4-(4-fluoro-2-methoxyphenyl) pyridin-2-yl)amino]-benzenesulfonamide (D2)

A mixture of 2-fluoro-4-iodopyridine (100 mg, 0.45 mmol), 3-amino-N-(tert-butyl)benzenesulfonamide (153 mg, 0.67 mmol), and Cs$_2$CO$_3$ (291 mg, 0.89 mmol) in dry DMF (3 mL) was heated at 150° C. for 1.5 h in a microwave oven. After addition of (4-fluoro-2-methoxyphenyl)boronic acid (152 mg, 0.89 mmol) the mixture was degassed with a stream of nitrogen for 5 minutes. Pd(dppf)Cl$_2$ (73 mg, 0.09 mmol) was added and the reaction mixture was heated to 140° C. for 90 minutes in a microwave oven. The mixture was diluted with EtOAc and washed twice with sat. aq. NaHCO$_3$-solution and once with brine. The organic layer was dried over MgSO$_4$ and concentrated under reduced pressure, and the residue was purified by preparative HPLC (water/ACN 95:5 to 0:100) to yield the desired product D2 as a yellow solid (9 mg, 5%). $^1$H NMR (400 MHz, d$_6$-DMSO, 300K) δ 1.12 (s, 9H), 3.82 (s, 3H), 6.89 (m, 2H), 6.97 (s, 1H), 7.06 (dd, J=11.5 Hz, J=2.4 Hz, 1H), 7.30 (d, J=8.0 Hz, 1H), 7.39 (m, 2H), 7.44 (s, 1H), 7.87 (d, J=8.0 Hz, 1H), 8.18 (d, J=5.4 Hz, 1H), 8.24 (m, 1H), 9.39 (s, 1H). MS (ES) $C_{22}H_{24}FN_3O_3S$ requires: 429. found: 430 (M+H)$^+$.

Example 6

4-[(4-(2-Methoxyphenyl)pyridin-2-yl)amino]benzenesulfonamide (E1)

Method A:
A mixture of A1 (230 mg, 1.05 mmol) and 4-aminobenzenesulfonamide (180 mg, 1.05 mmol) was heated with an oil bath for 1 hour at 150° C. The title compound E1 was obtained from the residue by preparative HPLC (water (0.1% TFA)/MeOH (0.1% TFA) gradient) as a colorless amorphous solid (82.5 mg, 22%). MS (ES) $C_{18}H_{17}N_3O_3S$ requires: 355. found: 356 (M+H)$^+$.

Method B:
To a solution of A4 (135 g, 0.36 mmol) in DME/water 9:1 (10 mL) was added (2-methoxyphenyl)boronic acid (55 mg, 0.36 mmol), Pd(PPh$_3$)$_2$Cl$_2$ (10 mg, 0.014 mmol), and K$_2$CO$_3$ (100 mg, 0.72 mmol). The mixture was heated at 80° C. for 45 minutes in a microwave oven. It was concentrated under reduced pressure, and the residue was purified by preparative HPLC (water (0.1% TFA)/MeOH (0.1% TFA) gradient) to give the title compound E1 (38.7 g, 30%). $^1$H NMR (400 MHz, d$_6$-DMSO, 300K) δ 3.80 (s, 3H), 6.95 (dd, J=5.3 Hz, J=1.5 Hz, 1H), 7.03-7.08 (m, 2H), 7.10 (bs, 2H), 7.15 (d, J=8.3 Hz, 1H), 7.35 (dd, J=7.6 Hz, J=1.7 Hz, 1H), 7.38-7.43 (m, 1H), 7.69 (d, J=8.9 Hz, 2H), 7.84 (d, J=8.8 Hz, 2H), 8.22 (d, J=5.3 Hz, 1H), 9.48 (s, 1H). MS (ES) $C_{18}H_{17}N_3O_3S$ requires: 355. found: 356 (M+H)$^+$.

Example 7

4-(2-Methoxyphenyl)-N-(3-(methylsulfonyl)phenyl) pyridin-2-amine (F1)

F1 was prepared from A1 (281 mg, 1.28 mmol) and 3-(methylsulfonyl)aniline hydrochloride (267 mg, 1.28 mmol) following the procedure reported for C1. Yield: 210 mg (46%). $^1$H NMR (400 MHz, d$_6$-DMSO, 300K) δ 3.18 (s, 3H), 3.80 (s, 3H), 7.02-7.08 (m, 2H), 7.12-7.18 (m, 2H), 7.35-7.45 (m, 2H), 7.50-7.53 (m, 1H), 7.53-7.62 (m, 1H), 7.92 (d, J=8.0 Hz, 1H), 8.12-8.19 (m, 2H), 10.05 (bs, 1H). MS (ES) $C_{19}H_{18}N_2O_3S$ requires: 354. found: 355 (M+H)$^+$.

Example 8

[3-((4-(4-Fluoro-2-methoxyphenyl)pyridin-2-yl) amino)phenyl]-methanesulfonamide (G1)

Intermediate A2 (119 mg, 0.5 mmol), (3-aminophenyl) methanesulfonamide (112 mg, 0.6 mmol), NaOC(CH$_3$)$_3$ (67 mg, 0.7 mmol), PdCl$_2$(CH$_3$CN)$_2$ (6.5 mg, 0.025 mmol, 5 mol %), and (9,9-dimethyl-9H-xanthene-4,5-diyl)bis(diphenylphosphine) [Xantphos] (23 mg, 0.04 mmol, 8 mol %) were dissolved in dry DMF (4 mL) and purged for 10 minutes with nitrogen. After heating at 110° C. for 18 hours the reaction mixture was filtered and the residue washed with toluene. The filtrate was concentrated under reduced pressure and purified by automated column chromatography (ISCO, gradient MeOH/DCM). The collected fractions which contained the title compound were further purified by preparative HPLC to yield 24 mg (12%) of G1 as an off-white solid. $^1$H NMR (300 MHz, d$_6$-DMSO, 298K) δ 3.84 (s, 3H), 4.22 (s, 2H), 6.81-6.94 (m, 5H), 6.98 (s, 1H), 7.07 (dd, J=11.7 Hz, J=4.2 Hz, 1H), 7.26 (t, J=6.6 Hz, 1H), 7.39 (dd, J=6.9 Hz, J=6.0 Hz, 1H), 7.56-7.61 (m, 1H), 7.79 (d, J=7.5 Hz, 1H), 8.16 (d, J=6.0 Hz, 1H), 9.12 (s, 1H).

MS (ES) $C_{19}H_{18}FN_3O_3S$ requires: 387. found: 388 (M+H)$^+$.

Example 9

[3-((4-(2-Methoxyphenyl)pyridin-2-yl)amino)phenyl]-methanesulfonamide (G2)

G2 was prepared from (3-aminophenyl)methanesulfonamide (85 mg, 0.46 mmol) and A1 (100 mg, 0.46 mmol)

following the procedure reported for G1 by heating in DMF for 3 hours, and it was obtained as a colorless amorphous solid (3.1 mg, 2%). $^1$H NMR (400 MHz, d$_6$-DMSO, 300K) δ 3.79 (s, 3H), 4.15 (s, 2H), 6.73 (bs, 2H), 6.84 (dd, J=5.3 Hz, J=1.5 Hz, 1H), 6.96-6.98 (m, 1H), 7.04 (dt, J=1.0 Hz, J=8.0 Hz, 1H), 7.13 (d, J=8.2 Hz, 1H), 7.21-7.25 (m, 2H), 7.33 (dd, J=7.6 Hz, J=1.8 Hz, 1H), 7.36-7.42 (m, 1H), 7.64-7.68 (m, 2H), 8.14 (d, J=5.3 Hz, 1H), 9.08 (s, 1H). MS (ES) C$_{19}$H$_{19}$N$_3$O$_3$S requires: 369. found: 370 (M+H)$^+$.

Example 10

1-[3-((4-(4-Fluoro-2-methoxyphenyl)pyridin-2-yl)amino)phenyl]-N,N-dimethylmethanesulfonamide (G3)

The title compound G3 was prepared from 1-(3-aminophenyl)-N,N-dimethylmethanesulfonamide (400 mg, 1.87 mmol) and intermediate A2 (532 mg, 2.24 mmol) following the procedure reported for G1 by heating the reaction mixture for 2 h at 140° C. in a microwave oven. The desired product G3 was obtained by flash chromatography on silica gel (cHex/EtOAc 80:20 to 20:80) as a white solid (274 mg, 35%). $^1$H NMR (400 MHz, d$_6$-DMSO, 300K) δ 2.71 (s, 6H), 3.81 (s, 3H), 4.34 (s, 2H), 6.82 (dd, J=5.3 Hz, J=1.5 Hz, 1H), 6.88 (dt, J=8.3 Hz, J=1.5 Hz, 1H), 6.91 (d, J=8.0 Hz, 1H), 6.95 (s, 1H), 7.05 (dd, J=11.4 Hz, J=2.4 Hz, 1H), 7.25 (t, J=7.8 Hz, 1H), 7.38 (dd, J=8.3 Hz, J=7.0 Hz, 1H), 7.67 (s, 1H), 7.72 (d, J=8.3 Hz, 1H), 8.14 (d, J=5.3 Hz, 1H), 9.11 (s, 1H). MS (ES) C$_{21}$H$_{22}$FN$_3$O$_3$S requires: 415. found: 416 (M+H)$^+$.

Example 11

2-[3-((4-(2-Methoxyphenyl)pyridin-2-yl)amino)phenyl]-ethanesulfonamide (H1)

H1 was prepared from A6 (92 mg, 0.46 mmol) and A1 (100 mg, 0.46 mmol) following the procedure reported for G1 and obtained as a pale yellow amorphous solid (4 mg, 2%). $^1$H NMR (400 MHz, d$_6$-DMSO, 300K) δ 2.95-3.03 (m, 2H), 3.21-3.29 (m, 2H), 3.81 (s, 3H), 6.87 (bs, 2H), 6.93-7.01 (m, 2H), 7.07 (t, J=7.5 Hz, 1H), 7.10-7.14 (m, 1H), 7.16 (d, J=8.5 Hz, 1H), 7.29 (t, J=8.0 Hz, 1H), 7.36-7.47 (m, 4H), 8.07 (d, J=5.4 Hz, 1H), 9.67 (bs, 1H). MS (ES) C$_{20}$H$_{21}$N$_3$O$_3$S requires: 383. found: 384 (M+H)$^+$.

Example 12

N$^1$-(4-(4-Fluoro-2-methoxyphenyl)pyridin-2-yl)benzene-1,3-diamine (I1)

To a solution of C2 (98 mg, 0.29 mmol) in THF/MeOH 1:1 (20 mL) was added Pd/C (10% w/w, 46 mg). The reaction mixture was stirred under hydrogen atmosphere (1 atm) at RT for 15 hours. The suspension was filtered through a pad of Celite® and the solvent was removed in vacuo to leave the desired product I1 as a brown solid (89 mg, 99%). MS (ES) C$_{18}$H$_{16}$FN$_3$O requires: 309. found: 310 (M+H)$^+$.

Example 13

N-[3-((4-(4-Fluoro-2-methoxyphenyl)pyridin-2-yl)amino)phenyl]-methanesulfonamide (J1)

To a solution of I1 (44 mg, 0.14 mmol) in dry pyridine (1 mL) was added methanesulfonyl chloride (24 mg, 0.21 mmol). After 2 h stirring at RT MeOH (0.1 mL) was added and the solvents were removed in vacuo. The residue was purified by flash chromatography on silica gel (EtOAc/MeOH 100:0 to 90:10) to yield the desired product J1 as a beige solid (36 mg, 66%). $^1$H NMR (400 MHz, d$_6$-DMSO, 300K) δ 3.01 (s, 3H), 3.82 (s, 3H), 6.91 (t, J=7.7 Hz, 1H), 6.97 (d, J=7.0 Hz, 1H), 7.08 (m, 2H), 7.20-7.37 (m, 4H), 7.47 (t, J=7.0 Hz, 1H), 8.04 (d, J=5.3 Hz, 1H), 9.86 (s, 1H), 10.23 (bs, 1H).

MS (ES) C$_{19}$H$_{18}$FN$_3$O$_3$S requires: 387. found: 388 (M+H)$^+$.

Example 14

N-[3-((4-(4-Fluoro-2-methoxyphenyl)pyridin-2-yl)amino)phenyl]-acetamide (J2)

The title compound J2 was prepared from I1 (44 mg, 0.14 mmol) and acetyl chloride (17 mg, 0.22 mmol) following the procedure described for J1 and obtained as a yellow solid (25 mg, 51%). $^1$H NMR (400 MHz, d$_6$-DMSO, 300K) δ 2.03 (s, 3H), 3.82 (s, 3H), 6.90 (t, J=7.8 Hz, 1H), 7.01 (d, J=5.2 Hz, 1H), 7.08 (d, J=11.1 Hz, 1H), 7.16-7.30 (m, 5H), 7.46 (t, J=7.3 Hz, 1H), 7.80 (s, 1H), 8.05 (d, J=5.5 Hz, 1H), 10.06 (s, 1H). MS (ES) C$_{20}$H$_{18}$FN$_3$O$_2$ requires: 351. found: 352 (M+H)$^+$.

Example 15

1-[3-((4-(4-Fluoro-2-methoxyphenyl)pyridin-2-yl)amino)phenyl]-N-propylmethanesulfonamide (K1)

A mixture of G3 (60 mg, 0.14 mmol), Cs$_2$CO$_3$ (94 mg, 0.29 mmol) and propylamine (0.2 mL, 2.43 mmol) in dioxane/water 10:1 (3.3 mL) was heated in a microwave oven for 8 h at 180° C. The mixture was purified by preparative HPLC (water/ACN 60:40 to 40:60) to yield the desired product K1 as a white solid (20 mg, 33%). $^1$H NMR (400 MHz, d$_6$-DMSO, 300K) δ 0.81 (t, J=7.3 Hz, 3H), 1.41 (sext, J=7.3 Hz, 2H), 2.85 (t, J=7.3 Hz, 2H), 3.81 (s, 3H), 4.22 (s, 2H), 6.83 (dd, J=5.3 Hz, J=1.4 Hz, 1H), 6.87 (m, 3H), 6.96 (s, 1H), 7.04 (dd, J=11.5 Hz, J=2.4 Hz, 1H), 7.23 (t, J=7.8 Hz, 1H), 7.37 (dd, J=8.5 Hz, J=6.9 Hz, 1H), 7.61 (s, 1H), 7.73 (dd, J=7.8 Hz, J=1.4 Hz, 1H), 8.13 (d, J=5.3 Hz, 1H), 9.09 (s, 1H). MS (ES) C$_{22}$H$_{24}$FN$_3$O$_3$S requires: 429. found: 430 (M+H)$^+$.

Materials and Methods:

1. Measurement of Binding Affinities to CDKs

This protocol describes how the LanthaScreen Eu Kinase Binding Assay was performed to determine dissociation constants (K$_d$) of compounds of general formula (I) and CDK/Cyclin complexes. The principle behind this assay is based upon the binding and displacement of an Alexa Fluor 647-labeled tracer, which binds to the active site of kinases. Binding of the tracer to the kinase is detected using a Eu-labeled antibody. Simultaneous binding of both the tracer and antibody to the kinase gives rise to a FRET-signal. Binding of an inhibitor to the kinase competes for binding with the tracer, resulting in a loss of FRET.

TABLE 2

Reagents, stock concentrations and final assay concentrations

| Kinase | Supplier | Kinase-conc. [nM] | Tracer | Supplier | Tracer-conc.[nM] | Antibody | Supplier | Antibody-conc. |
|---|---|---|---|---|---|---|---|---|
| CDK2/Cyclin A (135 kDa) | Proqinase | 5 | 236 | Invitrogen | 20 | Eu-Anti-GST | Cisbio | 1:750 |
| CDK7/CyclinH/MAT1 (126 kDa) | Carna Biosciences | 5 | 236 | Invitrogen | 60 | Eu-Anti-His | Invitrogen | 2 nM |
| CDK8/Cyclin C (97 kDa) | Invitrogen | 5 | 236 | Invitrogen | 20 | Eu-Anti-His | Invitrogen | 2 nM |
| CDK9/Cyclin T1 (132 kDa) | Invitrogen | 5 | 236 | Invitrogen | 30 | Eu-Anti-His | Cisbio | 1:250 |
| CDK9/Cyclin K (92 kDa) | Invitrogen | 10 | 236 | Invitrogen | 35 | Eu-Anti-His | Invitrogen | 4 nM |

The compounds of general formula (I) summarized in Table 1 were diluted from a 10 mM DMSO stock solution 1:10 in a total volume of 15 µL DMSO. This compound predilution was then serial diluted 1:3 over 8 steps in DMSO and briefly spun down. Each compound solution was now diluted 1:33.33 in kinase buffer (HEPES: 20 mM, pH: 8.0; $MgCl_2$: 10 mM; DTT: 1 mM; Brij-35: 0.01%), mixed thoroughly and spun down. For every sample, 5 µL of the diluted compound were mixed with 5 µL tracer working solution (e.g. 60 nM tracer 236 in kinase buffer for CDK2/Cyclin A) and 5 µL CDK/Cyclin/Anti-GST-AB-working solution (e.g. 15 nM CDK2/Cyclin A, 1:250 dilution of Anti-GST-AB in kinase buffer) in a well of a small volume 384 well plate (Corning Incorporated, Corning, N.Y., USA; order no. 3673). The tracer concentration was adjusted to its dissociation constant ($K_d$) for the CDK/Cyclin, which was 30 nM for CDK2/Cyclin A, CDK7/Cyclin H and CDK9/Cyclin T1, 20 nM for CDK8/Cyclin C, and 35 nM for CDK9/Cyclin K. For negative controls, in each well 5 µL of DMSO working solution (3% DMSO diluted in kinase buffer) was mixed with 5 µL Anti-GST-AB working solution (e.g. 1:250 dilution of Anti-GST-AB in kinase buffer for CDK2/Cyclin A) and 5 µL Tracer working solution (e.g. 60 nM Tracer 236 in kinase buffer for CDK2/Cyclin A). For positive controls, in each well 5 µL of DMSO working solution (3% DMSO diluted in kinase buffer) was mixed with 5 µL CDK/Cyclin/Anti-GST-AB-working solution: (e.g. 15 nM CDK2/Cyclin A, 1:250 dilution of Anti-GST-AB in kinase buffer) and 5 µL Tracer working solution (e.g. 60 nM Tracer 236 in kinase buffer for CDK2/Cyclin A). Positive and negative controls were calculated from at least 8 different sample wells. The 384 well plates were mixed in a Teleshaker plate mixer (Beckman Coulter, Brea, Calif., USA) at 2000 rpm for 40 sec, and incubated for 1 h at room temperature before reading. The FRET signal was measured at 340 nm excitation, 665 nm and 615 nm emission (for the kinase tracer and LanthaScreen Eu-AB, respectively) with an Envision spectrophotometer (Perkin Elmer, Waltham, Mass., USA) with 50 µs delay and 300 µs integration time. $K_d$ values were determined from the sigmoidal dose response curves with the software Quattro Workflow (Quattro GmbH, Munich, Germany). Results are presented in Table 4.

2. Measurement of Half Maximal Inhibitory Concentration to CDKs

This protocol describes how the Lance Ultra KinaSelect Assay was performed to determine half maximal inhibitory concentration ($IC_{50}$) of compounds of general formula (I) and CDK/Cyclin complexes. The principle behind this enzymatic assay is based upon the phosphorylation of the ULight-Peptide Substrat. It is detected by using a specific EU-labeled anti-phospho peptide antibody. The binding of the Eu-labeled anti-phospho peptide antibody to the phosphorylated ULight labeled peptide gives rise to a FRET-signal. Binding of an inhibitor to the kinase prevents phosphorylation of the ULight-MBP Substrat, resulting in a loss of FRET.

TABLE 3

Reagents, stock concentrations and final assay concentrations

| Kinase | Supplier | Kinase-conc. [nM] | ATP-conc. [µM] | Substrat | Supplier | Substrat-conc. [nM] | Antibody | Supplier | Antibody conc. [nM] |
|---|---|---|---|---|---|---|---|---|---|
| CDK1/CyclinB1 (91 kDa) | Carna | 2 | 20 | Ulight MBP | Perkin Elmer | 50 | Eu-anti-P-MBP | Perkin Elmer | 0.25 |
| CDK2/CyclinA (135 kDa) | Proqinase | 5 | 3 | Ulight MBP | Perkin Elmer | 50 | Eu-anti-P-MBP | Perkin Elmer | 0.25 |
| CDK4/CyclinD1 (123 kDa) | Invitrogen | 10 | 90 | Ulight MBP | Perkin Elmer | 50 | Eu-anti-P-MBP | Perkin Elmer | 0.25 |
| CDK6/CyclinD3 (123 kDa) | Carna | 5 | 55 | Ulight MBP | Perkin Elmer | 50 | Eu-anti-P-MBP | Perkin Elmer | 0.025 |
| CDK7/CyclinH/ MAT1 (126 kDa) | Invitrogen | 10 | 25 | Ulight MBP | Perkin Elmer | 50 | Eu-anti-P-MBP | Perkin Elmer | 0.25 |
| CDK9/CyclinT1 (132 kDa) | Invitrogen | 10 | 25 | Ulight MBP | Perkin Elmer | 50 | Eu-anti-P-MBP | Perkin Elmer | 0.,25 |
| CDK9/CyclinK (92 kDa) | Invitrogen | 10 | 125 | Ulight MBP | Perkin Elmer | 50 | Eu-anti-P-MBP | Perkin Elmer | 0.25 |

The compounds of general formula (I) summarized in Table 5 were diluted from a 10 mM DMSO stock solution 1:10 in a total volume of 15 µL DMSO. This compound predilution was then serial diluted 1:3 over 8 steps in DMSO and briefly spun down. Each compound solution was now diluted 1:20 in Enzymatic Buffer (HEPES: 50 mM, pH: 7.5; $MgCl_2$: 10 mM; EGTA: 1 mM; DTT: 2 mM; Tween-20: 0.01%), mixed thoroughly and spun down. For every sample, 2 µL of the diluted compound were mixed with 6 µL CDK/Cyclin/Substrat solution and 2 µL ATP solution in a well of a small volume 384 well plate (Corning Incorporated, Corning, N.Y., USA; order no. 3673). The CDK/Cyclin was diluted to the appropriate concentration (see Table 3) and the ATP concentration was adjusted to its $IC_{50}$ concentration for the CDK/Cyclin, which was 3 µM for CDK2/Cyclin A, 20 µM for CDK1/Cyclin B1, 25 µM for CDK7/Cyclin H and CDK9/Cyclin T1, 55 µM for CDK6/Cyclin D3, 90 µM for CDK4/Cyclin D1 and 125 µM for CDK9/Cyclin K. For negative controls, in each well 2 µL of DMSO solution (1% final DMSO assay concentration) was mixed with 6 µL substrate solution (50 nM ULight MBP final assay concentration) and 2 µL ATP solution (appropriate final concentration see Table 3). For positive controls, in each well 2 µL of DMSO solution (1% final DMSO assay concentration) was mixed with 6 µL CDK/Cyclin/Substrat (appropriate final concentration see Table 3) and 2 µL Tracer ATP solution (appropriate final concentration see Table 3). Positive and negative controls were calculated from at least 8 different sample wells. The 384 well plates were mixed in a Teleshaker plate mixer (Beckman Coulter, Brea, Calif., USA) at 2000 rpm for 40 sec, and incubated for 1 h at room temperature. Before reading, 10 µL the detection buffer (Lance Detection Buffer 1×; EDTA: 20 nM; Eu-Anti-P-MBP: see Table 3) was added. The FRET signal was measured at 340 nm excitation, 665 nm and 615 nm emission (for the kinase tracer and LanthaScreen Eu-AB, respectively) with an Envision spectrophotometer (Perkin Elmer, Waltham, Mass., USA) with 50 µs delay and 300 µs integration time. $IC_{50}$ values were determined from the sigmoidal dose response curves with the software Quattro Workflow (Quattro GmbH, Munich, Germany). Results are presented in Table 5.

3. Cellular Assays 3.1 RNA-Polymerase II Ser2 Cellular Phosphorylation Assay:

HCT-116 cells (DSMZ, Braunschweig, Germany) were maintained in Mc Coy's cell culture medium+glutamine (PAN Biotech GmbH, Aidenbach, Germany) supplemented with 10% fetal calf serum (PAA Laboratories GmbH, Pasching, Austria) and grown at 37° C., 5% $CO_2$. For the cellular phosphorylation assay, cells were seeded with 2×105 cells/well/1 ml in 24-well plates (Greiner Bio One, Frickenhausen, Germany; catalog #662160). The compounds of general formula (I) summarized in Table 6 were diluted from a 10 mM DMSO stock solution 1:10 in a total volume of 15 µL DMSO. After overnight incubation at 37° C./5% $CO_2$, 1.5 µL of a compound diluted in DMSO was added to each sample well. Wells with cells and 0.15% DMSO in culture medium were used as positive controls, wells without cells and 0.15% DMSO in culture medium were used as negative controls. The cells were incubated with the compounds for 72 h at 37° C./5% $CO_2$. Before lysis, cells were washed with phosphate buffered saline. Phosphorylation of RNA Polymerase II Ser2 and tubulin levels for normalization were analyzed afterwards with the Multi-Array technology (Meso Scale Discovery, Gaithersburg, Md., USA), a combination of antibody coupled electrochemiluminescence detection and patterned arrays. Manufacturer's instructions were followed and all solutions were purchased from Meso Scale Discovery. In brief, cells were lysed by 30 min incubation in CLB1 lysis buffer (Zeptosens, Witterswil, Switzerland; 60 µL per well), and supernatants were cleared by centrifugation. For analysis of RNA Polymerase II Ser2-phosphorylation, lysates were diluted 1:50 with Meso Scale Lysis Buffer supplemented with phosphatase- and protease-inhibitors, and 25 µL of each sample was pipetted in a well of a MSD Multi-Array 96-Well Plate Sector® Imager High Bind Plate (Meso Scale Discovery; catalog #L15XB-3/L11XB-3), and incubated for 2 h at room temperature. 150 µL Meso Scale Tris Wash Buffer supplemented with 3% w/v Meso Scale Blocker A were added per well, then plates were sealed and incubated 1 h with vigorous shaking. Plates were washed with 1× Tris Wash Buffer (10× Meso Scale Wash Buffer diluted 1:10 in destilled water), 25 µL of antibody solution was added (CTD7 3E10 antibody from Helmholtz Zentrum Munich, Germany, diluted 1:100 in Meso Scale Tris Wash Buffer supplemented with 1% w/v Meso Scale Blocker A), and plates were washed three times in 1× Tris Wash Buffer. 25 µL of MSD® SULFO-TAG™ Goat-Anti-Rat-Antibody (Meso Scale Discovery, atalog # R32AH-1, diluted 1:125 in Tris Wash Buffer with 1% (w/v) blocker A) were added per well, plates were sealed and incubated with vigorous shaking for 1 h at room temperature. Finally, plates were washed three times with Tris Wash Buffer, 150 µl 2× Read Buffer (Meso Scale Discovery) were added per well and plates were analyzed immediately in a Sector Imager from Meso Scale Discovery. For determination of tubulin protein levels, samples were analyzed with the protocol for RNA Polymerase II Ser2-phosphorylation, with an anti-tubulin antibody (rabbit; BIODESIGN International, catalog #T59840R, diluted 1:100) and a MSD® SULFO-TAG™ Goat-Anti-Rat-Antibody (Meso Scale Discovery, catalog #R32AH-1, diluted 1:125). RNA Polymerase II Ser2 phosphorylation was normalized with tubulin protein levels, and $IC_{50}$ values were calculated with the software XLFit (IDBS, Guildford, UK) from 2-fold dilution series comprising 6 concentrations in duplicates. Results are presented in Table 6.

3.2 NF-kappaB Reporter Assay

Cells were maintained in RPMI cell culture medium+glutamine (PAN Biotech GmbH, Aidenbach, Germany) supplemented with 10% fetal calf serum (PAA Laboratories GmbH, Pasching, Austria) and grown at 37° C., 5% $CO_2$. HEK293 cells grown to 50% confluence were transfected with the Amaxa® Cell Line Nucleofector® Kit V (Lonza, Basel, Switzerland, catalog # VCA-1003). Transfections were performed according to manufacturer's optimized protocol for transfection of HEK293 cells. In brief, 2×10⁵ cells were transfected with 5 µg highly purified plasmid DNA. Cells were transfected with a NF-kappa B reporter plasmid (pNFkBluc), pTALluc for control, or pMAXGFP for transfection control. After transfection, cells were taken up in 500 µL RPMI1640 cell culture medium, incubated for 1 h at 37° C., and 4.5 ml DMEM without phenol red were added per transfection. Transfected cells were seeded in 96 well plates (Greiner Bio-One, Frickenhausen, Germany, catalog #655098) with 100 µL cell suspension per well and incubated for 48 h. To each well, 100 µL DMEM with 2× concentrated compound diluted from 10 mM DMSO stocks, or 100 µL DMEM with 0.4% DMSO for control wells, was added. The compounds of general formula (I) summarized in Table 6 were used in this assay. Cells were stimulated with 20 ng/ml TNF alpha, and plates were incubated for 5 h at 37° C./5% $CO_2$. Cell culture supernatants were removed to leave 100 µl medium per well, followed by addition of 100 µl Bright Glo luciferase assay reagent (Promega, Madison, Wis., USA, catalog # E2620), and shaking for 5 minutes in the dark. Luminescence was measured with a Victor Photospectrometer (Perkin Elmer, Waltham, Mass., USA). $IC_{50}$ values were calculated with the software Excel Fit (IDBS, Guildford, UK)

from 2-fold dilution series comprising at least 10 concentrations in duplicates. Results are presented in Table 6.

3.3 TNF Alpha Release Assay

Freshly isolated peripheral blood mononuclear cells (PBMCs) were seeded in 96-well cell culture plates with 200,000 cells in 100 μl cell culture medium (DMEM cell culture medium+glutamine from PAN Biotech GmbH, Aidenbach, Germany) supplemented with 10% fetal calf serum (PAA Laboratories GmbH, Pasching, Austria) per well and incubated overnight at 37° C., 5% $CO_2$. To each well, 100 μL cell culture medium with 2× concentrated test compounds diluted from 10 mM DMSO stocks, or 100 μL DMEM with 0.4% DMSO for control wells, was added. The compounds of general formula (I) summarized in Table 6 were used in this assay. After incubation for 1 h at 37° C., 5% $CO_2$, cells were stimulated with 1 μg/mL LPS (Lipopolysaccharides, Sigma, catalog #L4391-1 MG; 1 mg/ml stock solution), or left untreated for negative controls, and plates were incubated for 6 h at 37° C./5% $CO_2$. The cell culture plates were centrifuged at 2000 rpm for 5 minutes, and supernatants were transferred to fresh 96-well polypropylene plates. 25 μL of supernatants were transferred into 96-well-plates of the human TNF alpha-tissue culture kit (Meso Scale Discovery, Gaithersburg, Md., USA), and manufacturer's instructions were followed for analysis of TNF alpha levels. Chemoluminescence was measured in the Mesoscale Sector Imager, and $IC_{50}$ values were calculated with the software Excel Fit (IDBS, Guildford, UK) from 2-fold dilution series comprising at least 6 concentrations in duplicates. Results are presented in Table 6.

3.4 Cell Viability Assays

Hela- or MDAMB468-Cells were maintained in RPMI 1640 or McCoy's 5A cell culture medium+glutamine (PAN Biotech GmbH, Aidenbach, Germany; order no. P04-22100; P04-05500) supplemented with 10% fetal calf serum "Gold" (PAA Laboratories GmbH, Pasching, Austria; order no. A15-151) and grown at 37° C., 5% $CO_2$. For the cell viability assay, cells were seeded with a density of 400 (Hela cells, DSMZ Braunschweig order no. ACC57) or 800 (MDAMB468 cells, ATCC order no. HTB-132) per well in 25 μL in 384-well plates (Greiner Bio-One, Frickenhausen, Germany; order no. 781080). After overnight incubation at 37° C./5% $CO_2$, 25 nL or 75 nL compound were added to each sample well by using BIOMEK FXP Laboratory Automation Workstation (Beckman Coulter, USA). Wells with cells and 0.1% or 0.3% DMSO in culture medium were used as positive controls, wells with cells and 10 μM staurosporine in culture medium were used as negative controls. The cells were incubated with the compounds for 72 h at 37° C./5% $CO_2$. For measurement of cell viability 25 μL Cell Titer Glo reagent (Promega, Madison, USA; order no. G7573), 1:2 diluted with cell culture medium, was added to each well. The 384 well-plates were placed for 2 min on a orbital microplate shaker and incubated for further 10 min at room temperature to stabilize the luminescence signal. Luminescence was measured by Envision Plate Reader (Perkin Elmer, USA). $IC_{50}$ values were calculated with the software Excel Fit (IDBS, Guildford, UK) from 3-fold dilution series comprising at least 8 concentrations in duplicates. Results are presented in Table 6.

Results:

1. Measurement of Binding Affinities to CDKs

The dissociation constants $K_d$ of the compounds according to the present invention for binding to CDK9, CDK7, and CDK2, respectively, are summarized in Table 4. Comparison of binding constants of a special compound of formula (I) for a number of different CDKs shows that binding of a compound to CKD9 is always stronger than binding to other CDKs. Thus, a compound of formula (I) binds or interacts specifically with CKD9 and at least selectively with CDK9.

TABLE 4

Affinity for CDK9, CDK7, and CDK2 of compounds according to the present invention

| ① Nomenclature | | ② | ③ | ④ | ⑤ |
|---|---|---|---|---|---|
| B1 | 4-(2-Methoxyphenyl)-N-phenylpyridin-2-amine | c | n.t. | n.t. | n.t. |
| C1 | 4-(2-Methoxyphenyl)-N-(3-nitrophenyl)pyridin-2-amine | b | b | n.t. | n.t. |
| D1 | 3-[(4-(2-Methoxyphenyl)pyridin-2-yl)amino]benzenesulfonamide | a | a | d | a |
| D2 | N-(tert-Butyl)-3-[(4-(4-fluoro-2-methoxyphenyl)pyridin-2-yl)amino]benzenesulfonamide | c | n.t. | d | n.t. |
| E1 | 4-[(4-(2-Methoxyphenyl)pyridin-2-yl)amino]benzenesulfonamide | b | a | d | a |
| F1 | 4-(2-Methoxyphenyl)-N-(3-(methylsulfonyl)phenyl)pyridin-2-amine | a | a | n.t. | b |
| G1 | [3-((4-(4-Fluoro-2-methoxyphenyl)pyridin-2-yl)amino)phenyl]methanesulfonamide | a | a | d | b |
| G2 | [3-((4-(2-Methoxyphenyl)pyridin-2-yl)amino)phenyl]methanesulfonamide | a | n.t. | d | a |
| G3 | 1-[3-((4-(4-Fluoro-2-methoxyphenyl)pyridin-2-yl)amino)phenyl]-N,N-dimethylmethanesulfonamide | a | n.t. | d | b |
| H1 | 2-[3-((4-(2-Methoxyphenyl)pyridin-2-yl)amino)phenyl]ethanesulfonamide | a | n.t. | d | b |
| J1 | N-[3-((4-(4-Fluoro-2-methoxyphenyl)pyridin-2-yl)amino)phenyl]methanesulfonamide | a | n.t. | c | a |
| J2 | N-[3-((4-(4-Fluoro-2-methoxyphenyl)pyridin-2-yl)amino)phenyl]acetamide | a | n.t. | d | b |
| K1 | 1-[3-((4-(4-Fluoro-2-methoxyphenyl)pyridin-2-yl)amino)phenyl]-N-propylmethanesulfonamide | a | n.t. | d | b |

Activity range "a" means, that the compounds do have a $K_d$ (dissociation constant) <100 nM, activity range "b" means, that the compounds do have a $K_d$ between 100 and 1000 nM, activity range "c" means that the compounds do have an $K_d$ between 1000 and 10000 nM, activity range "d" means that the compounds do have an $K_d$ > 10000 nM;

"n.t." means that the compounds have not been tested in this assay.

① Compound Number
② CDK9/Cyclin T1 (activity range)
③ CDK9/Cyclin K (activity range)
④ CDK7 (activity range)
⑤ CDK2 (activity range)

2. Measurement of Half Maximal Inhibitory Concentration to CDKs in Enzymatic Assays The inhibitory activities of the compounds according to the present invention are shown in Table 5 as half-maximal inhibition constant ($IC_{50}$) values for inhibition of CDK9, CDK1, CDK2, CDK4, CDK6, and CDK7, respectively.

TABLE 5

Inhibition for CDK9, CDK1, CDK2, CDK4, CDK6, and CDK7 of compounds according to the present invention

| ① Nomenclature | | ② | ③ | ④ | ⑤ | ⑥ | ⑦ |
|---|---|---|---|---|---|---|---|
| B1 | 4-(2-Methoxyphenyl)-N-phenylpyridin-2-amine | c | n.t. | n.t. | n.t. | n.t. | n.t. |
| C1 | 4-(2-Methoxyphenyl)-N-(3-nitrophenyl)pyridin-2-amine | c | n.t. | n.t. | n.t. | n.t. | n.t. |
| D1 | 3-[(4-(2-Methoxyphenyl)pyridin-2-yl)amino]benzenesulfonamide | a | c | b | d | d | d |
| E1 | 4-[(4-(2-Methoxyphenyl)pyridin-2-yl)amino]benzenesulfonamide | b | n.t. | a | n.t. | n.t. | d |
| F1 | 4-(2-Methoxyphenyl)-N-(3-(methylsulfonyl)phenyl)pyridin-2-amine | a | n.t. | n.t. | n.t. | n.t. | n.t. |
| G1 | [3-((4-(4-Fluoro-2-methoxyphenyl)pyridin-2-yl)amino)phenyl]methanesulfonamide | a | c | c | c | d | d |
| G2 | [3-((4-(2-Methoxyphenyl)pyridin-2-yl)amino)phenyl]methanesulfonamide | a | n.t. | b | n.t. | n.t. | d |
| G3 | 1-[3-((4-(4-Fluoro-2-methoxyphenyl)pyridin-2-yl)amino)phenyl]-N,N-dimethylmethanesulfonamide | a | n.t. | c | n.t. | n.t. | d |
| H1 | 2-[3-((4-(2-Methoxyphenyl)pyridin-2-yl)amino)phenyl]ethanesulfonamide | a | n.t. | c | n.t. | n.t. | d |
| J1 | N-[3-((4-(4-Fluoro-2-methoxyphenyl)pyridin-2-yl)amino)phenyl]methanesulfonamide | a | n.t. | b | n.t. | n.t. | d |
| J2 | N-[3-((4-(4-Fluoro-2-methoxyphenyl)pyridin-2-yl)amino)phenyl]acetamide | a | n.t. | b | n.t. | n.t. | d |
| K1 | 1-[3-((4-(4-Fluoro-2-methoxyphenyl)pyridin-2-yl)amino)phenyl]-N-propylmethanesulfonamide | b | n.t. | c | n.t. | n.t. | d |

Activity range "a" means, that the compounds do have a $IC_{50}$ (inhibitory concentration at 50% of maximal effect) <100 nM,
activity range "b" means, that the compounds do have a $IC_{50}$ between 100 and 1000 nM,
activity range "c" means that the compounds do have an $IC_{50}$ between 1000 and 10000 nM,
activity range "d" means that the compounds do have an $IC_{50}$ > 10000 nM;
"n.t." means that the compounds have not been tested in this assay.
①: Compound Number
②: CDK9 LANCE assay (activity range)
③: CDK1 LANCE assay (activity range)
④: CDK2 LANCE assay (activity range)
⑤: CDK4 LANCE assay (activity range)
⑥: CDK6 LANCE assay (activity range)
⑦: CDK7 LANCE assay (activity range)

3. Cellular Assays

The cellular activity of the compounds according to the present invention are shown in Table 6 as half-maximal inhibition constant ($IC_{50}$) values on LPS-induced TNF alpha release in PBMCs, NF-kappaB reporter gene activation, cellular CDK9 activity (RNA Polymerase II Ser2 phosphorylation), and cell viability in Hela- or MDAMB468-Cells, respectively.

TABLE 6

Inhibition of LPS-induced TNF alpha release in PBMCs, NF-kappaB reporter gene activation, cellular CDK9 activity (RNA Polymerase II Ser2 phosphorylation), and cell viability in Hela- or MDAMB468-Cells by compounds according to the present invention.

| ① Nomenclature | | ② | ③ | ④ | ⑤ | ⑥ |
|---|---|---|---|---|---|---|
| B1 | 4-(2-Methoxyphenyl)-N-phenylpyridin-2-amine | d | d | n.t. | n.t. | d |
| C1 | 4-(2-Methoxyphenyl)-N-(3-nitrophenyl)pyridin-2-amine | c | c | n.t. | n.t. | d |
| D1 | 3-[(4-(2-Methoxyphenyl)pyridin-2-yl)amino]benzenesulfonamide | b | b | c | b | b |
| E1 | 4-[(4-(2-Methoxyphenyl)pyridin-2-yl)amino]benzenesulfonamide | c | c | n.t. | d | c |
| F1 | 4-(2-Methoxyphenyl)-N-(3-(methylsulfonyl)phenyl)pyridin-2-amine | c | c | n.t. | c | c |
| G1 | [3-((4-(4-Fluoro-2-methoxyphenyl)pyridin-2-yl)amino)phenyl]methanesulfonamide | b | b | n.t. | c | c |
| G3 | 1-[3-((4-(4-Fluoro-2-methoxyphenyl)pyridin-2-yl)amino)phenyl]-N,N-dimethylmethanesulfonamide | n.t. | n.t. | n.t. | d | c |
| J1 | N-[3-((4-(4-Fluoro-2-methoxyphenyl)pyridin-2-yl)amino)phenyl]methanesulfonamide | n.t. | n.t. | n.t. | c | c |

TABLE 6-continued

Inhibition of LPS-induced TNF alpha release in PBMCs, NF-kappaB reporter gene activation, cellular CDK9 activity (RNA Polymerase II Ser2 phosphorylation), and cell viability in Hela- or MDAMB468-Cells by compounds according to the present invention.

| ① Nomenclature | ② | ③ | ④ | ⑤ | ⑥ |
|---|---|---|---|---|---|
| J2 N-[3-((4-(4-Fluoro-2-methoxyphenyl)pyridin-2-yl)amino)phenyl] acetamide | n.t. | n.t. | n.t. | d | c |
| K1 1-[3-((4-(4-Fluoro-2-methoxyphenyl)pyridin-2-yl)amino)phenyl]-N-propylmethanesulfonamide | n.t. | n.t. | n.t. | d | d |

Activity range "a" means, that the compounds do have a $IC_{50} < 100$ nM,
activity range "b" means, that the compounds do have a $IC_{50}$ between 100 and 1000 nM,
activity range "c" means that the compounds do have an $IC_{50}$ between 1000 and 10000 nM,
activity range "d" means that the compounds do have an $IC_{50} > 10000$ nM;
"n.t." means that the compounds have not been tested in this assay.
①: Compound Number
②: TNF alpha release (activity range)
③: NF-kappaB activation (activity range)
④: RNA Polymerase II Ser2 Phosphorylation (activity range)
⑤: Cell Viability - Hela cells (activity range)
⑥: Cell Viability - MDAMB468 cells (activity range)

The invention claimed is:
1. Compounds having the general formula (III)

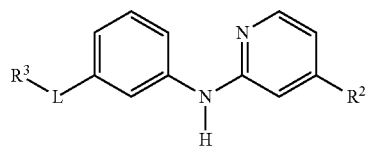

Formula (III)

wherein

L is a bond or —$CR^5R^6$—, —$CR^5R^6$—$CR^7R^8$—, —$CR^5R^6$—$CR^7R^8$—$CR^9R^{10}$—, —$CR^5R^6$—$CR^7R^8$—$CR^9R^{10}$—$CR^{11}R^{12}$—;

$R^5$—$R^{12}$ represent independently of each other —H, —$CH_3$, —$C_2H_5$, —$C_3H_7$, —F, —Cl, —Br, —I;

$R^3$ is selected from —H, —$NO_2$, —$NH_2$, —CN, —F, —Cl, —Br, —I, —$CH_3$, —$C_2H_5$, —$C_3H_7$, —$CH(CH_3)_2$, —$C_4H_9$, —$CH_2$—$CH(CH_3)_2$, —$CH(CH_3)$—$C_2H_5$, —$C(CH_3)_3$, —O—$CH_3$, —O—$C_2H_5$, —O—$C_3H_7$, —O—$CH(CH_3)_2$, —O—$C_4H_9$, —O—$CH_2$—$CH(CH_3)_2$, —O—$CH(CH_3)$—$C_2H_5$, —O—$C(CH_3)_3$, —$CR^{13}R^{14}R^{21}$, —$CR^{13}R^{14}$—$CR^{15}R^{16}R^{21}$, —O—$CR^{13}R^{14}R^{21}$, —$CR^{13}R^{14}$—$CR^{15}R^{16}$—$CR^{17}R^{18}R^{21}$, —$CR^{13}R^{14}$—$CR^{15}R^{16}$—$CR^{17}R^{18}$—$CR^{19}R^{20}R^{21}$, —O—$CR^{13}R^{14}$—$CR^{15}R^{16}R^{21}$, —O—$CR^{13}R^{14}$—$CR^{15}R^{16}$—$CR^{17}R^{18}R^{21}$, —$SO_2R^{22}$, —$CONR^{23}R^{24}$, —$NR^{25}COR^{22}$, —O—$CR^{13}R^{14}$—$CR^{15}R^{16}$—$CR^{17}R^{18}$—$CR^{19}R^{20}R^{21}$, —$NR^{25}SO_2NR^{23}R^{24}$, —$NR^{25}SO_2R^{22}$, —$NR^{25}CONR^{23}R^{24}$, —$SO_2NR^{23}R^{24}$, —$SO(NR^{26})R^{22}$, —$NR^{23}R^{24}$;

$R^{13}$—$R^{21}$ and $R^{29}$—$R^{32}$ represent independently of each other —H, —$CH_3$, —$C_2H_5$, —$C_3H_7$, —$C_4H_9$, —F, —Cl, —Br, —I;

$R^{26}$ is —H, —$CH_3$, —$C_2H_5$, —$C_3H_7$, —$CH(CH_3)_2$, —$C_4H_9$, —$CH_2$—$CH(CH_3)_2$, —$CH(CH_3)$—$C_2H_5$, —$C(CH_3)_3$, —$C_5H_{11}$, —$CH(CH_3)$—$C_3H_7$, —$CH_2$—$CH(CH_3)$—$C_2H_5$, —$CH(CH_3)$—$CH(CH_3)_2$, —$C(CH_3)_2$—$C_2H_5$, —$CH_2$—$C(CH_3)_3$, —$CH(C_2H_5)_2$, —$C_2H_4$—$CH(CH_3)_2$, —$C_6H_{13}$, —$C_3H_6$—$CH(CH_3)_2$, —$C_2H_4$—$CH(CH_3)$—$C_2H_5$, —$CH(CH_3)$—$C_4H_9$, —$CH_2$—$CH(CH_3)$—$C_3H_7$, —$CH(CH_3)$—$CH_2$—$CH(CH_3)_2$, —$CH(CH_3)$—$CH(CH_3)$—$C_2H_5$, —$CH_2$—$CH(CH_3)$—$CH(CH_3)_2$, —$CH_2$—$C(CH_3)_2$—$C_2H_5$, —$C(CH_3)_2$—$C_3H_7$, —$C(CH_3)_2$—$CH(CH_3)_2$, —$C_2H_4$—$C(CH_3)_3$, —$CH(CH_3)$—$C(CH_3)_3$, —$CR^{13}R^{14}R^{21}$, —$COR^{28}$, —$CR^{13}R^{14}$—$CR^{15}R^{16}R^{21}$, —$CR^{13}R^{14}$—$CR^{15}R^{16}$—$CR^{17}R^{18}$—$CR^{19}R^{20}$—$CR^{29}R^{30}R^{21}$, —$CR^{13}R^{14}$—$CR^{15}R^{16}$—$CR^{17}R^{18}R^{21}$, —$CR^{13}R^{14}$—$CR^{15}R^{16}$—$CR^{17}R^{18}$—$CR^{19}R^{20}R^{21}$, —$CR^{13}R^{14}$—$CR^{15}R^{18}$—$CR^{17}R^{18}$—$CR^{19}R^{20}$—$CR^{29}R^{30}$—$CR^{31}R^{32}R^{21}$, —$COOR^{28}$, —$R^{27}$;

$R^{22}$, and $R^{28}$ are independently selected from —$R^{27'}$, —$CR^{13}R^{14}R^{21}$, —$CH_3$, —$C_2H_5$, —$CR^{13}R^{14}$—$CR^{15}R^{16}R^{21}$, —$CR^{13}R^{14}$—$CR^{15}R^{16}$—$CR^{17}R^{18}$—$CR^{19}R^{20}$—$CR^{29}R^{30}R^{21}$, —$CR^{13}R^{14}$—$CR^{15}R^{16}$—$CR^{17}R^{18}R^{21}$, —$CR^{13}R^{14}$—$CR^{15}R^{16}$—$CR^{17}R^{18}$—$CR^{19}R^{20}R^{21}$, —$CR^{13}R^{14}$—$CR^{15}R^{16}$—$CR^{17}R^{18}$—$CR^{19}R^{20}$—$CR^{29}R^{30}$—$CR^{31}R^{32}R^{21}$, —$C_3H_7$, —$CH_2Ph$; —$CH_2Ph$ the phenyl group of which may further be substituted by one, two, three, four or five substituents selected from the group consisting of —$CH_3$, —$C_2H_5$, —$C_3H_7$, —F, —Cl, —Br and —I;

$R^{27}$, $R^{27'}$ and $R^{27''}$ are independently selected from

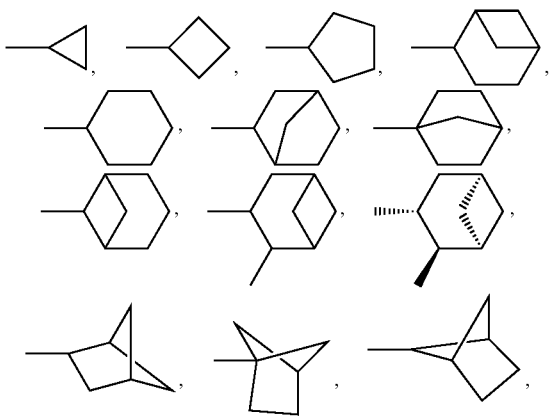

-continued

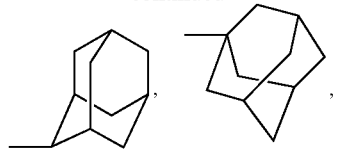

these C₃-C₁₀-cycloalkyl groups may further be substituted by one, two, three, four, five or more substituents selected from the group consisting of —F, —Cl, —Br and —I;

$R^{23}$, $R^{24}$, $R^{77}$ and $R^{78}$ are independently of each other selected from —H, —CH₃, —C₂H₅, —CR¹³R¹⁴R²¹, —C₃H₇, —CR¹³R¹⁴—CR¹⁵R¹⁶R²¹, —CR¹³R¹⁴—CR¹⁵R¹⁶—CR¹⁷R¹⁸—CR¹⁹R²⁰—CR²⁹R³⁰R²¹, —CR¹³R¹⁴—CR¹⁵R¹⁶—CR¹⁷R¹⁸R²¹, —CR¹³R¹⁴—CR¹⁵R¹⁶—CR¹⁷R¹⁸—CR¹⁹R²⁰R²¹, —CR¹³R¹⁴—CR¹⁵R¹⁶—CR¹⁷R¹⁸—CR¹⁹R²⁰—CR²⁹R³⁰—CR³¹R³²R²¹, —CR¹³R¹⁴—CR¹⁵R¹⁶—O—R³³, —CR¹³R¹⁴—CR¹⁵R¹⁶—NR³³R³⁴, —CR¹³R¹⁴—CR¹⁵R¹⁶—CR¹⁷R¹⁸—NR³³R³⁴, —CR¹³R¹⁴—CR¹⁵R¹⁶—CR¹⁷R¹⁸—CR¹⁹R²⁰—NR³³R³⁴, —CR¹³R¹⁴—CR¹⁵R¹⁶—CR¹⁷R¹⁸—O—R³³, —CR¹³R¹⁴—CR¹⁵R¹⁶—CR¹⁷R¹⁸—CR¹⁹R²⁰—CR²⁹R³⁰—NR³³R³⁴, -Ph, —CH₂PH, phenyl group which may further be substituted by one, two, three, four or five substituents selected from the group consisting of —CH₃, —C₂H₅, —C₃H₇, —F, —Cl, —Br and —I; —CH₂Ph the phenyl group of which may further be substituted by one, two, three, four or five substituents selected from the group consisting of —CH₃, —C₂H₅, —C₃H₇, —F, —Cl, —Br and —I; or both residues $R^{23}$ and $R^{24}$ together form with the nitrogen atom to which they are attached a azetidine, pyrrolidine, piperidine, piperazine, azepane, or morpholine ring;

$R^{33}$ and $R^{34}$ represent independently of each other —H, —CH₃, —C₂H₅, —C₃H₇, —C₄H₉, —CH₂Ph, —COOC(CH₃)₃, —COOCH₃, —COOCH₂CH₃, —COOCH₂CH₂CH₃, —COOCH(CH₃)₂, —COOCH₂Ph, —COCH₃;

and $R^{25}$ is selected from —H, —CH₃, —C₂H₅, —C₃H₇, —CH(CH₃)₂, —C₄H₉, —CH₂—CH(CH₃)₂, —CH(CH₃)—C₂H₅ or —C(CH₃)₃;

$R^4$ is selected from —H, —NO₂, —CN, —F, —Cl, —Br, —I, —CR³⁵R³⁶R³⁷, —CR³⁵R³⁶—CR³⁸R³⁹—CR⁴⁰R⁴¹—CR⁴²R⁴³R³⁷, —O—CR³⁵R³⁶—CR³⁸R³⁹R³⁷, —O—CR³⁵R³⁶—CR³⁸R³⁹—CR⁴⁰R⁴¹R³⁷, —CR³⁵R³⁶—CR³⁸R³⁹—CR⁴⁰R⁴¹R³⁷, —O—CR³⁵R³⁶—CR³⁸R³⁹—CR⁴⁰R⁴¹—CR⁴²R⁴³R³⁷, —CR³⁵R³⁶—CR³⁸R³⁹R³⁷, —O—CR³⁵R³⁶—CR³⁸R³⁹—CR⁴⁰R⁴¹—CR⁴²R⁴³—CR⁴⁴R⁴⁵R³⁷, —O—CR³⁵R³⁶R³⁷, —O—CR³⁵R³⁶—CR³⁸R³⁹—CR⁴⁰R⁴¹—CR⁴²R⁴³—CR⁴⁴R⁴⁵—CR⁴⁶R⁴⁷R³⁷, —CR³⁵R³⁶—CR³⁸R³⁹—CR⁴⁰R⁴¹—CR⁴²R⁴³—CR⁴⁴R⁴⁵R³⁷, —CR³⁵R³⁶—CR³⁸R³⁹—CR⁴⁰R⁴¹—CR⁴²R⁴³—CR⁴⁴R⁴⁵—CR⁴⁶R⁴⁷R³⁷, —OCH₂Ph, —R²⁷″, —O—R²⁷″;

$R^{35}$—$R^{47}$ and $R^{62}$—$R^{74}$ represent independently of each other —H, —CR⁴⁸R⁴⁹R⁵⁰, —CR⁴⁸R⁴⁹—CR⁵¹R⁵²R⁵⁰, —CR⁴⁸R⁴⁹—CR⁵¹R⁵²—CR⁵³R⁵⁴R⁵⁰, —CR⁴⁸R⁴⁹—CR⁵¹R⁵²—CR⁵³R⁵⁴—CR⁵⁵R⁵⁶R⁵⁰, —F, —Cl, —Br, —I;

$R^{48}$—$R^{56}$ represent independently of each other —H, —F, —Cl, —Br, —I;

$R^4$ together with $R^{22}$ or $R^{23}$ or $R^{24}$ or $R^{25}$ may form a group —CH₂CH₂— or —CH₂CH₂CH₂— if $R^4$ is attached ortho to -L-R³;

$R^2$ is

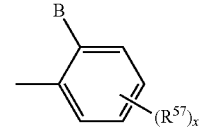

$R^{57}$ is selected from —H, —OH, —NO₂, —CN, —F, —Cl, —Br, —I, —NR⁶⁰R⁶¹, -D-R⁶⁴, -D-NR⁶⁰R⁶¹, —O-D-R⁶⁴, —CHO, —CH₂OH, —CO—R⁶⁰, —CH₂OR⁶⁰;

D, D' and D″ represent independently of each other —CR⁶²R⁶³—, —CR⁶²R⁶³—CR⁶⁵R⁶⁶—, —CR⁶²R⁶³—CR⁶⁵R⁶⁶—CR⁶⁷R⁶⁸—, —CR⁶²R⁶³—CR⁶⁵R⁶⁶—CR⁶⁷R⁶⁸—CR⁶⁹R⁷⁰—;

$R^{60}$, $R^{61}$, $R^{75}$ and $R^{76}$ represent independently of each other —H, —CH₃, —C₂H₅, —C₃H₇, —CH(CH₃)₂, —C₄H₉, —CH₂—CH(CH₃)₂, —CH(CH₃)—C₂H₅, —C(CH₃)₃, -(cyclo-C₃H₅);

x is 0, 1, 2 or 3;

B is —OCH₃, —OC₂H₅, —OC₃H₇, —O-cyclo-C₃H₅, —OCH(CH₃)₂, —OC(CH₃)₃, —OC₄H₉;

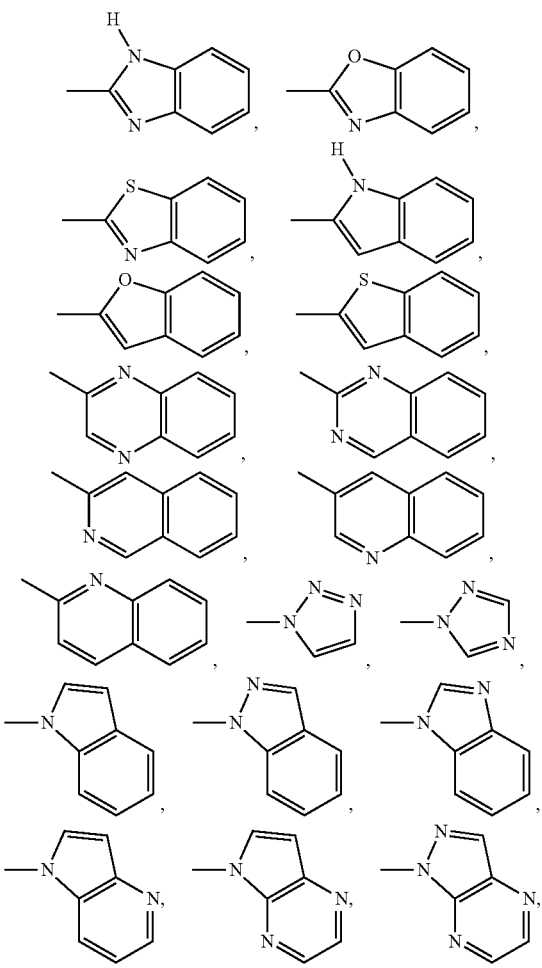

-continued

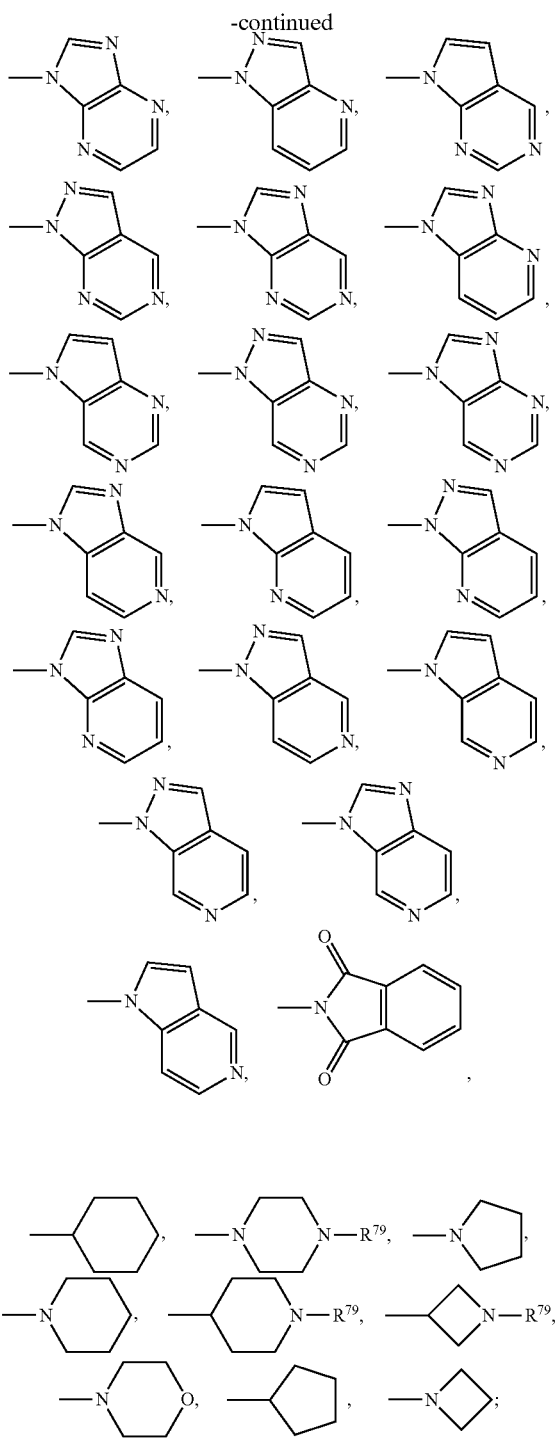

and enantiomers, stereoisomeric forms, mixtures of enantiomers, diastereomers, mixtures of diastereomers, acid salt forms, tautomers, and racemates of the above mentioned compounds and pharmaceutically acceptable salts thereof.

2. Compounds according to claim 1, wherein the substituent -L-R$^3$ represents —NO$_2$, —NH$_2$, —SO$_2$R$^{22}$, —CONR$^{23}$R$^{24}$, —NR$^{25}$COR$^{22}$, —NR$^{25}$SO$_2$NR$^{23}$R$^{24}$, —NR$^{25}$SO$_2$R$^{22}$, —NR$^{25}$CONR$^{23}$R$^{24}$, —SO$_2$NR$^{23}$R$^{24}$, —SO(NR$^{26}$)R$^{22}$, —NR$^{23}$R$^{24}$, —CH$_2$—NO$_2$, —CH$_2$—NH$_2$, —CH$_2$—SO$_2$R$^{22}$, —CH$_2$—CONR$^{23}$R$^{24}$, —CH$_2$—NR$^{25}$COR$^{22}$, —CH$_2$—NR$^{25}$SO$_2$NR$^{23}$R$^{24}$, —CH$_2$—NR$^{25}$SO$_2$R$^{22}$, —CH$_2$—NR$^{25}$CONR$^{23}$R$^{24}$, —CH$_2$—SO$_2$NR$^{23}$R$^{24}$, —CH$_2$—SO(NR$^{26}$)R$^{22}$, —CH$_2$—NR$^{23}$R$^{24}$, —CH$_2$CH$_2$—NO$_2$, —CH$_2$CH$_2$—NH$_2$, —CH$_2$CH$_2$—SO$_2$R$^{22}$, —CH$_2$CH$_2$—CONR$^{23}$R$^{24}$, —CH$_2$CH$_2$—NR$^{25}$COR$^{22}$, —CH$_2$CH$_2$—NR$^{25}$SO$_2$NR$^{23}$R$^{24}$, —CH$_2$CH$_2$—NR$^{25}$SO$_2$R$^{22}$, —CH$_2$CH$_2$—NR$^{25}$CONR$^{23}$R$^{24}$, —CH$_2$CH$_2$—SO$_2$NR$^{23}$R$^{24}$, —CH$_2$CH$_2$—SO(NR$^{26}$)R$^{22}$, or —CH$_2$CH$_2$—NR$^{23}$R$^{24}$.

3. Compounds according to claim 1 wherein
-L-R$^3$ represents —NO$_2$, —NH$_2$, —NH(CH$_3$), —NH(C$_2$H$_5$), —NH(C$_3$H$_7$), —N(CH$_3$)$_2$, —N(C$_2$H$_5$)$_2$, —N(C$_3$H$_7$)$_2$, —SO$_2$CH$_3$, —SO$_2$C$_2$H$_5$, —SO$_2$C$_3$H$_7$, —CONH$_2$, —CONH(CH$_3$), —CONH(C$_2$H$_5$), —CONH(C$_3$H$_7$), —CON(CH$_3$)$_2$, —CON(C$_2$H$_5$)$_2$, —CON(C$_3$H$_7$)$_2$, —NHCOCH$_3$, —NHCOC$_2$H$_5$, —NHCOC$_3$H$_7$, —NHSO$_2$NH$_2$, —NHSO$_2$NH(CH$_3$), —NHSO$_2$NH(C$_2$H$_5$), —NHSO$_2$NH(C$_3$H$_7$), —NHSO$_2$N(CH$_3$)$_2$, —NHSO$_2$N(C$_2$H$_5$)$_2$, —NHSO$_2$N(C$_3$H$_7$)$_2$, —NHSO$_2$CH$_3$, —NHSO$_2$C$_2$H$_5$, —NHSO$_2$C$_3$H$_7$, —NHCONH$_2$, —NHCONH(CH$_3$), —NHCONH(C$_2$H$_5$), —NHCONH(C$_3$H$_7$), —NHCON(CH$_3$)$_2$, —NHCON(C$_2$H$_5$)$_2$, —NHCON(C$_3$H$_7$)$_2$, —SO$_2$NH$_2$, —SO$_2$NH(CH$_3$), —SO$_2$NH(C$_2$H$_5$), —SO$_2$NH(C$_3$H$_7$), —SO$_2$N(CH$_3$)$_2$, —SO$_2$N(C$_2$H$_5$)$_2$, —SO$_2$N(C$_3$H$_7$)$_2$, —SO(NH)CH$_3$, —SO(NH)C$_2$H$_5$, —SO(NH)C$_3$H$_7$, —CH$_2$—NO$_2$, —CH$_2$—NH$_2$, —CH$_2$—NH(CH$_3$), —CH$_2$—NH(C$_2$H$_5$), —CH$_2$—NH(C$_3$H$_7$), —CH$_2$—N(CH$_3$)$_2$, —CH$_2$—N(C$_2$H$_5$)$_2$, —CH$_2$—N(C$_3$H$_7$)$_2$, —CH$_2$—SO$_2$CH$_3$, —CH$_2$—SO$_2$C$_2$H$_5$, —CH$_2$—SO$_2$C$_3$H$_7$, —CH$_2$—CONH$_2$, —CH$_2$—CONH(CH$_3$), —CH$_2$—CONH(C$_2$H$_5$), —CH$_2$—CONH(C$_3$H$_7$), —CH$_2$—CON(CH$_3$)$_2$, —CH$_2$—CON(C$_2$H$_5$)$_2$, —CH$_2$—CON(C$_3$H$_7$)$_2$, —CH$_2$—NHCOCH$_3$, —CH$_2$—NHCOC$_2$H$_5$, —CH$_2$—NHCOC$_3$H$_7$, —CH$_2$—NHSO$_2$NH$_2$, —CH$_2$—NHSO$_2$NH(CH$_3$), —CH$_2$—NHSO$_2$NH(C$_2$H$_5$), —CH$_2$—NHSO$_2$NH(C$_3$H$_7$), —CH$_2$—NHSO$_2$N(CH$_3$)$_2$, —CH$_2$—NHSO$_2$N(C$_2$H$_5$)$_2$, —CH$_2$—NHSO$_2$N(C$_3$H$_7$)$_2$, —CH$_2$—NHSO$_2$CH$_3$, —CH$_2$—NHSO$_2$C$_2$H$_5$, —CH$_2$—NHSO$_2$C$_3$H$_7$, —CH$_2$—NHCONH$_2$, —CH$_2$—NHCONH(CH$_3$), —CH$_2$—NHCONH(C$_2$H$_5$), —CH$_2$—NHCONH(C$_3$H$_7$), —CH$_2$—NHCON(CH$_3$)$_2$, —CH$_2$—NHCON(C$_2$H$_5$)$_2$, —CH$_2$—NHCON(C$_3$H$_7$)$_2$, —CH$_2$—SO$_2$NH$_2$, —CH$_2$—SO$_2$NH(CH$_3$), —CH$_2$—SO$_2$NH(C$_2$H$_5$), —CH$_2$—SO$_2$NH(C$_3$H$_7$), —CH$_2$—SO$_2$N(CH$_3$)$_2$, —CH$_2$—SO$_2$N(C$_2$H$_5$)$_2$, —CH$_2$—SO$_2$N(C$_3$H$_7$)$_2$, —CH$_2$—SO(NH)CH$_3$, —CH$_2$—SO(NH)C$_2$H$_5$, —CH$_2$—SO(NH)C$_3$H$_7$, —CH$_2$CH$_2$—NO$_2$, —CH$_2$CH$_2$—NH$_2$, —CH$_2$—CH$_2$—NH(CH$_3$), —CH$_2$—CH$_2$—NH(C$_2$H$_5$), —CH$_2$—CH$_2$—NH(C$_3$H$_7$), —CH$_2$—CH$_2$—N(CH$_3$)$_2$, —CH$_2$—CH$_2$—N(C$_2$H$_5$)$_2$, —CH$_2$—CH$_2$—N(C$_3$H$_7$)$_2$, —CH$_2$—CH$_2$—SO$_2$CH$_3$, —CH$_2$—CH$_2$—SO$_2$C$_2$H$_5$, —CH$_2$—CH$_2$—SO$_2$C$_3$H$_7$, —CH$_2$—CH$_2$—CONH$_2$, —CH$_2$—CH$_2$—CONH(CH$_3$), —CH$_2$—CH$_2$—CONH(C$_2$H$_5$), —CH$_2$—CH$_2$—CONH(C$_3$H$_7$), —CH$_2$—CH$_2$—CON(CH$_3$)$_2$, —CH$_2$—CH$_2$—CON(C$_2$H$_5$)$_2$, —CH$_2$—CH$_2$—CON(C$_3$H$_7$)$_2$, —CH$_2$—CH$_2$—NHCOCH$_3$, —CH$_2$—CH$_2$—NHCOC$_2$H$_5$, —CH$_2$—CH$_2$—NHCOC$_3$H$_7$, —CH$_2$—CH$_2$—NHSO$_2$NH$_2$, —CH$_2$—CH$_2$—NHSO$_2$NH(CH$_3$), —CH$_2$—CH$_2$—NHSO$_2$NH(C$_2$H$_5$), —CH$_2$—CH$_2$—NHSO$_2$NH(C$_3$H$_7$), —CH$_2$—CH$_2$—NHSO$_2$N(CH$_3$)$_2$, —CH$_2$—CH$_2$—NHSO$_2$N(C$_2$H$_5$)$_2$, —CH$_2$—CH$_2$—NHSO$_2$N(C$_3$H$_7$)$_2$, —CH$_2$—CH$_2$—NHSO$_2$CH$_3$, —CH$_2$—CH$_2$—NHSO$_2$C$_2$H$_5$, —CH$_2$—CH$_2$—NHSO$_2$C$_3$H$_7$, —CH$_2$—CH$_2$—NH- CONH$_2$, —CH$_2$—CH$_2$—NHCONH(CH$_3$), —CH$_2$—CH$_2$—NHCONH(C$_2$H$_5$), —CH$_2$—CH$_2$—NHCONH(C$_3$H$_7$), —CH$_2$—CH$_2$—NHCON(CH$_3$)$_2$, —CH$_2$—CH$_2$—NHCON(C$_2$H$_5$)$_2$, —CH$_2$—CH$_2$—NHCON(C$_3$H$_7$)$_2$, —CH$_2$—CH$_2$—SO$_2$N H$_2$, —CH$_2$—CH$_2$—SO$_2$NH(CH$_3$), —CH$_2$—CH$_2$—SO$_2$NH(C$_2$H$_5$), —CH$_2$—CH$_2$—SO$_2$NH(C$_3$H$_7$), —CH$_2$—CH$_2$—SO$_2$N (CH$_3$)$_2$, —CH$_2$—CH$_2$—SO$_2$N (C$_2$H$_5$)$_2$, —CH$_2$—CH$_2$—SO$_2$N(C$_3$H$_7$)$_2$, —CH$_2$—CH$_2$—SO(NH)CH$_3$, —CH$_2$—CH$_2$—SO(NH)C$_2$H$_5$, —CH$_2$—CH$_2$—SO(NH)C$_3$H$_7$, and R$^2$ has the meanings as defined in claim 1.

4. Compounds according to claim 1, wherein the substituent-L-R$^3$ represents —NO$_2$, —NH$_2$, —SO$_2$NH$_2$, —SO$_2$—NH—C(CH$_3$)$_3$, —SO$_2$CH$_3$, —CH$_2$—SO$_2$N H$_2$, —CH$_2$—SO$_2$—N(CH$_3$)$_2$, —CH$_2$—CH$_2$—SO$_2$N H$_2$, —NHSO$_2$CH$_3$, —NHCOCH$_3$, or —CH$_2$—SO$_2$—NH(CH$_2$CH$_2$CH$_3$).

5. A compound selected from the group consisting of:
4-(2-Methoxyphenyl)-N-phenylpyridin-2-amine,
4-(2-Methoxyphenyl)-N-(3-nitrophenyl)pyridin-2-amine,
4-(4-Fluoro-2-methoxyphenyl)-N-(3-nitrophenyl)pyridin-2-amine,
3-[(4-(2-Methoxyphenyl)pyridin-2-yl)amino]benzenesulfonamide,
4-(2-Methoxyphenyl)-N-(3-(methylsulfonyl)phenyl)pyridin-2-amine,
[3-((4-(4-Fluoro-2-methoxyphenyl)pyridin-2-yl)amino)phenyl]methanesulfonamide,
[3-((4-(2-Methoxyphenyl)pyridin-2-yl)amino)phenyl]methanesulfonamide,
2-[3-((4-(2-Methoxyphenyl)pyridin-2-yl)amino)phenyl]ethanesulfonamide,
N-(tert-Butyl)-3-[(4-(2-methoxyphenyl)pyridin-2-yl)amino]benzenesulfonamide,
1-[3-((4-(4-Fluoro-2-methoxyphenyl)pyridin-2-yl)amino)phenyl]-N,N-dimethyl-methanesulfonamide,
N1-(4-(4-Fluoro-2-methoxyphenyl)pyridin-2-yl)benzene-1,3-diamine,
N-[3-((4-(4-Fluoro-2-methoxyphenyl)pyridin-2-yl)amino)phenyl]methane-sulfonamide, and
N-[3-((4-(4-Fluoro-2-methoxyphenyl)pyridin-2-yl)amino)phenyl]acetamide.

6. Pharmaceutical composition comprising at least one compound according to claim 1 as an active ingredient, together with at least one pharmaceutically acceptable carrier, excipient and/or diluent.

7. Pharmaceutical composition according to claim 6 further comprising one or more further anti-tumor agents.

* * * * *